United States Patent
Shuttleworth et al.

(10) Patent No.: US 9,862,685 B2
(45) Date of Patent: Jan. 9, 2018

(54) HISTONE DEACETYLASE INHIBITORS

(71) Applicant: Karus Therapeutics Limited, Oxfordshire (GB)

(72) Inventors: Stephen J. Shuttleworth, Oxfordshire (GB); Cyrille D. Tomassi, Oxfordshire (GB); Alexander R. L. Cecil, Oxfordshire (GB); Somhairle MacCormick, Oxfordshire (GB); William J. Nodes, Oxfordshire (GB); Franck A. Silva, Oxfordshire (GB)

(73) Assignee: Karus Therapeutics Limited, Abingdon, Oxfordshire (GB)

( * ) Notice: Subject to any disclaimer, the term of this patent is extended or adjusted under 35 U.S.C. 154(b) by 0 days.

(21) Appl. No.: 14/890,331

(22) PCT Filed: May 12, 2014

(86) PCT No.: PCT/GB2014/051454
§ 371 (c)(1),
(2) Date: Nov. 10, 2015

(87) PCT Pub. No.: WO2014/181137
PCT Pub. Date: Nov. 13, 2014

(65) Prior Publication Data
US 2016/0096804 A1 Apr. 7, 2016

(30) Foreign Application Priority Data

May 10, 2013 (GB) .................................. 1308409.0
Aug. 28, 2013 (GB) .................................. 1315253.3

(51) Int. Cl.
| | | |
|---|---|---|
| A61K 31/497 | (2006.01) |
| C07D 401/12 | (2006.01) |
| C07D 401/14 | (2006.01) |
| C07D 403/12 | (2006.01) |
| C07D 213/72 | (2006.01) |
| C07D 213/74 | (2006.01) |
| C07D 413/12 | (2006.01) |
| C07D 417/12 | (2006.01) |
| C07D 417/14 | (2006.01) |
| C07D 495/04 | (2006.01) |
| C07D 285/08 | (2006.01) |
| A61K 45/06 | (2006.01) |
| A61K 31/433 | (2006.01) |
| A61K 31/4365 | (2006.01) |
| A61K 31/4439 | (2006.01) |
| A61K 31/444 | (2006.01) |
| A61K 31/501 | (2006.01) |
| A61K 31/506 | (2006.01) |
| A61K 31/5377 | (2006.01) |

(52) U.S. Cl.
CPC .......... *C07D 213/72* (2013.01); *A61K 31/433* (2013.01); *A61K 31/4365* (2013.01); *A61K 31/444* (2013.01); *A61K 31/4439* (2013.01); *A61K 31/497* (2013.01); *A61K 31/501* (2013.01); *A61K 31/506* (2013.01); *A61K 31/5377* (2013.01); *A61K 45/06* (2013.01); *C07D 213/74* (2013.01); *C07D 285/08* (2013.01); *C07D 401/12* (2013.01); *C07D 401/14* (2013.01); *C07D 403/12* (2013.01); *C07D 413/12* (2013.01); *C07D 417/12* (2013.01); *C07D 417/14* (2013.01); *C07D 495/04* (2013.01)

(58) Field of Classification Search
CPC ... C07D 401/12; C07D 401/14; C07D 403/12
See application file for complete search history.

(56) References Cited

U.S. PATENT DOCUMENTS

| | | |
|---|---|---|
| 4,017,500 A | 4/1977 | Mayer et al. |
| 7,022,840 B2 | 4/2006 | Kobuke et al. |
| 8,748,458 B2 | 6/2014 | Shuttleworth et al. |
| 9,200,007 B2 | 12/2015 | Shuttleworth et al. |
| 9,266,879 B2 | 2/2016 | Shuttleworth et al. |
| 9,340,503 B2 | 5/2016 | Shuttleworth et al. |
| 2002/0099210 A1 | 7/2002 | Alexander et al. |
| 2002/0151544 A1 | 10/2002 | Hayakawa et al. |

(Continued)

FOREIGN PATENT DOCUMENTS

| | | |
|---|---|---|
| CN | 101228161 A | 7/2008 |
| CN | 101663276 A | 3/2010 |

(Continued)

OTHER PUBLICATIONS

Madsen et al. The effect of various zinc binding groups on inhibition of histone deacetylases 1-11. ChemMedChem Mar. 27, 2014;9(3):614-26. Epub Dec. 27, 2013.*

(Continued)

*Primary Examiner* — Brian McDowell
(74) *Attorney, Agent, or Firm* — Goodwin Procter LLP

(57) ABSTRACT

The present invention is a compound of the formula or a pharmaceutically acceptable salt thereof. The compounds are useful as HDAC inhibitors.

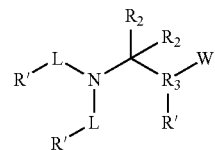

12 Claims, No Drawings

(56) References Cited

U.S. PATENT DOCUMENTS

| | | |
|---|---|---|
| 2004/0106787 A1 | 6/2004 | Kobuke et al. |
| 2004/0235888 A1 | 11/2004 | Yamamori et al. |
| 2007/0135466 A1 | 6/2007 | Ledeboer et al. |
| 2008/0125440 A1 | 5/2008 | Cai et al. |
| 2008/0207729 A1 | 8/2008 | Pisano et al. |
| 2008/0221112 A1 | 9/2008 | Yamamori et al. |
| 2011/0201608 A1 | 8/2011 | Hoffmann et al. |
| 2011/0305729 A1 | 12/2011 | Shuttleworth et al. |
| 2012/0171199 A1 | 7/2012 | Dotson et al. |
| 2012/0178737 A1 | 7/2012 | Shuttleworth et al. |
| 2013/0109688 A1 | 5/2013 | Shuttleworth et al. |
| 2014/0235671 A1 | 8/2014 | Shuttleworth et al. |
| 2015/0080395 A1 | 3/2015 | Shuttleworth et al. |
| 2015/0361074 A1 | 12/2015 | Shuttleworth et al. |
| 2016/0108057 A1 | 4/2016 | Shuttleworth et al. |

FOREIGN PATENT DOCUMENTS

| | | | |
|---|---|---|---|
| CN | 104125946 A | | 10/2014 |
| EP | 0226099 A2 | | 6/1987 |
| EP | 0509400 A1 | | 10/1992 |
| EP | 0556396 A1 | | 8/1993 |
| EP | 0887348 A1 | | 12/1998 |
| EP | 1277738 A1 | | 1/2003 |
| EP | 1724267 A1 | | 11/2006 |
| EP | 2508510 A1 | | 10/2012 |
| EP | 2813506 A1 | | 12/2014 |
| JP | H11302254 A | | 11/1999 |
| JP | 2008542428 A | | 11/2008 |
| JP | 2012508223 A | | 4/2012 |
| JP | 201139550 A | | 5/2013 |
| JP | 2014503535 A | | 2/2014 |
| WO | WO-97/40017 A2 | | 10/1997 |
| WO | WO-01/83456 A1 | | 11/2001 |
| WO | WO-02/02551 A1 | | 1/2002 |
| WO | WO-0234748 A1 | | 5/2002 |
| WO | WO-02/085400 A1 | | 10/2002 |
| WO | WO-03/075929 A1 | | 9/2003 |
| WO | WO-2004/072047 A1 | | 8/2004 |
| WO | WO-2006/037335 A2 | | 4/2006 |
| WO | WO-2006/046035 A1 | | 5/2006 |
| WO | WO-2006/088949 | | 8/2006 |
| WO | WO-2006/127587 A1 | | 11/2006 |
| WO | WO-2006/131484 | | 12/2006 |
| WO | WO-2007/050348 A2 | | 5/2007 |
| WO | WO-2007/084667 A2 | | 7/2007 |
| WO | WO-2007/085540 A1 | | 8/2007 |
| WO | WO-2007/122410 A1 | | 11/2007 |
| WO | WO-2007/127183 A1 | | 11/2007 |
| WO | WO-2008/007780 A1 | | 1/2008 |
| WO | WO-2008/033746 | | 3/2008 |
| WO | WO-2008/055068 A2 | | 5/2008 |
| WO | WO-2008/062201 A1 | | 5/2008 |
| WO | WO-2008/094992 A2 | | 8/2008 |
| WO | WO-2008/139987 A1 | | 11/2008 |
| WO | WO-2008137270 | | 11/2008 |
| WO | WO-2008/145688 A2 | | 12/2008 |
| WO | WO-2008/150827 A1 | | 12/2008 |
| WO | WO-2009/063240 A1 | | 5/2009 |
| WO | WO-2009/137462 A2 | | 11/2009 |
| WO | WO-2010/015520 A1 | | 2/2010 |
| WO | WO-2010/037765 A2 | | 4/2010 |
| WO | WO-2010/052569 A2 | | 5/2010 |
| WO | WO-2010/086646 A1 | | 8/2010 |
| WO | WO-2012/045804 A1 | | 4/2012 |
| WO | WO-2012/082997 A1 | | 6/2012 |
| WO | WO-2012/106343 A2 | | 8/2012 |
| WO | WO-2012/136722 A1 | | 10/2012 |
| WO | WO-2013/052110 A1 | | 4/2013 |
| WO | WO-2013052613 A1 | | 4/2013 |
| WO | WO-2013/088404 A1 | | 6/2013 |
| WO | WO-2013/095060 A1 | | 6/2013 |
| WO | WO-2013/132270 A1 | | 9/2013 |
| WO | WO-2014/032019 A2 | | 2/2014 |
| WO | WO-2014/072714 A1 | | 5/2014 |
| WO | WO-2014/072937 A1 | | 5/2014 |
| WO | WO-2014/100227 A1 | | 6/2014 |
| WO | WO-2014/139465 A1 | | 9/2014 |
| WO | WO-2014/153280 A1 | | 9/2014 |
| WO | WO-2014/181137 A1 | | 11/2014 |
| WO | WO-2015/121657 A1 | | 8/2015 |
| WO | WO-2016/031815 A1 | | 3/2016 |
| WO | WO-2016/067038 A1 | | 5/2016 |
| WO | WO-2016/067040 A1 | | 5/2016 |

OTHER PUBLICATIONS

U.S. Appl. No. 15/095,829, Scriptaid Isosteres and Their Use in Therapy, filed Apr. 11, 2016, Pending.

U.S. Appl. No. 13/145,250, Scriptaid Isosteres and Their Use in Therapy, filed Aug. 30, 2011, Granted.

U.S. Appl. No. 13/388,164, Tricyclic Heterocyclic Compounds as Phosphoinositide 3-Kinase Inhibitors, Mar. 27, 2012, Granted.

U.S. Appl. No. 13/643,210, Naphthridine Derivatives as PI3K Inhibitors for the Treatment of Cancer and Immune-Inflammatory, filed Jan. 7, 2013, Allowed.

U.S. Appl. No. 14/266,197, Scriptaid Isosteres and Their Use in Therapy, filed Apr. 30, 2014, Published.

U.S. Appl. No. 14/382,196, Phosphoinositide 3-Kinase Inhibitors, filed Aug. 29, 2014, Published.

U.S. Appl. No. 14/441,401, Novel Histone Deacetylase Inhibitors and Their Use in Therapy, filed May 7, 2015, Pending.

U.S. Appl. No. 14/920,410, Tricyclic Heterocyclic Compounds as Phosphoinositide 3-Kinase Inhibitors, Oct. 22, 2015, Pending.

Alvarez-Rua C et al., 'Multiple Hydrogen Bonds and Tautomerism in Naphthyridine Derivatives,' New J Chem, May 7, 2004 (May 7, 2004)(ePub), 28:700-7.

Anonymous, 'Abstract No. 2009:1018972 CAPLUS,' for 'Lett Drug Des Disc, (2009), 6(4):268-77,' STN CA Caesar Accession No. 1028, Nov. 17, 2015 (Nov. 17, 2015), CAplus Chemical Abstract Service, American Chemical Society, Columbus, OH (Publ), pp. 1-2 XP-002751577.

Anonymous, 'CAS Registration No. RN-1257852-06-4 for Glycine, N—1H-imadazol-1-yl-N-3-pyridazinyl,' Dec. 29, 2010 (Dec. 29, 2010), CAS Registry, Chemical Abstracts Service, American Chemical Society, Columbus, OG (Publ), pp. 1, XP-002751578.

Anonymous, Chemcats, Accession No. 0056415163, for '1,6-Naphthyridine, 7-(3-methylphenyl)-5-(4-morpholinyl)-' Apr. 22, 2011 (Apr. 22, 2011), CAS Registry No. 1214393-37-9, Chemical Abstracts Service, American Chemical Society, Columbus, OH (Publ), pp. 1, XP-002643660.

Anonymous, Chemcats, Accession No. 0056415178, for '1,6-Naphthyridine, 5-(4-morpholinyl)-7-(2-pyridinyl)-,' Apr. 22, 2011 (Apr. 22, 2011), CAS Registry No. 1214438-02-4, Chemical Abstracts Service, American Chemical Society, Columbus, OH (Publ), pp. 1, XP-002643660.

Assem el-SK et al., 'Effects of a Section of Histone Deacetylase Inhibitors on Mast Cell Activation and Airway and Colonic Smooth Muscles Contraction,' Int Immunopharmacol, Dec. 20, 2008 (Dec. 20, 2008) Sep. 19, 2008 (Sep. 19, 2008)(ePub), 8(13-14):1793-801.

Bouchecareilh M et al., 'Histone Deactylase Inhibitor (HDACi) Suberoylanilide Hydroxamic Acid (SAHA)-Mediated Correction of alpha1-Antitrypsin Deficiency,' J Biol Chem, Nov. 2, 2012 (Nov. 2, 2012) Sep. 20, 2012 (Sep. 20, 2012)(ePub), 287(45):38265-78.

Ciarlo E et al., 'Epigenetics in Sepsis: Targeting Histone Deacetylases,' Int J Antimicrob Agents, Jun. 2013 (Jun. 2013) May 9, 2013 (May 9, 2013)(ePub), 42(Supp):S8-12.

Clarke JD et al., 'Differential Effects of Sulforaphane on Histone Deacetylases, Cell Cycle Arrest and Apoptosis in Normal Prostate Cells Versus Hyperplastic and Cancerous Prostate Cells,' Mol Nutr Food Res, Jul. 2011 (Jul. 2011) Mar. 4, 2011 (Mar. 4, 2011)(ePub), 55(7):999-1009.

Crisanti MC et al., 'The HDAC Inhibitor Panobinostat (LBH589) Inhibits Mesothelioma and Lung Cancer Cells in vitro and in vivo with Particular Efficacy for Small Cell Lung Cancer,' Mol Cancer Ther, Aug. 2009 (Aug. 2009) Aug. 11, 2009 (Aug. 11, 2009)(ePub), 8(8):2221-31.

(56) References Cited

OTHER PUBLICATIONS

Cuadro AM et al., 'Synthesis of Highly Stabilised Ylides from N-[2-(1,3-Bensazolylmethyl)] Pyridinium Salts,' Tetrahedron, Jan. 1990 (Jan. 1990), 46(17):6033-46.
Djabali K and Christiano AM, 'Hairless Contains a Novel Nuclear Matrix Targeting Signal and Associates with Histone Deacetylase 3 in Nuclear Speckles,' Differentiation, Oct. 2004 (Oct. 2004), 72(8):410-8.
Downes JM et al., 'Biological Analogs. Spectroscopic Characteristics of Mercato- and Disulfide-Copper (II) Coordination in Relation to Type I Proteins,' Inorg Chem, Apr. 1981 (Apr. 1981), 20(4):1081-6.
Ferrara N and Alitalo K, 'Clinical Applications of Angiogenic Growth Factors and Their Inhibitors,' Nat Med, Dec. 1999 (Dec. 1999), 5(12):1359-64.
Galardon E et al., 'Modeling the Inhibition of Peptide Deformylase by Hydroxamic Acids: Influence of the Sulfur Donor,' Daltron Trans, Mar. 14, 2007 (Mar. 14, 2007) Jan. 23, 2007 (Jan. 23, 2007)(ePub), (10):1047-52.
Gillespie J et al., 'Histone Deacetylases are Dysregulated in Rheumatoid Arthritis and a Novel Histone Deacetylase 3-Selective Inhibitor Reduces Interleukin-6 Production by Peripheral Blood Mononuclear Cells from Rheumatoid Arthritis Patients,' Arthritis Rheum, Feb. 2012 (Feb. 2012), 64(2):418-22.
Govindarajan N et al., 'Reducing HDAC6 Ameliorated Cognitive Deficits in Mouse Model for Alzheimer's Disease,' EMBO Mol Med, Jan. 2013 (Jan. 2013) Nov. 26, 2012 (Nov. 26, 2013)(ePub), 5(1):52-63.
Gryder BE at al., 'Histone Deacetylase Inhibitors Equipped with Estrogen Receptor Modulation Activity,' J Med Chem, Jul. 25, 2013 (Jul. 25, 2013) Jul. 3, 2013 (Jul. 3, 2013)(ePub), 56(14):5782-96.
Hancock WW et al., 'HDAC Inhibitor Therapy in Autoimmunity and Transplantation,' Ann Rheum Dis, Apr. 2012 (Apr. 2012), 71(Supp 2):i46-54.
Haquette P et al., 'Synthesis of N-Functionalized 2,2'-dipyridylamine Ligands, Complexation to Ruthenium (II) and Anchoring of Complexes to Papain from Papaya Latex,' J Organomet Chem, Mar. 15, 2009 (Mar. 15, 2009), 694(6):937-41.
Hawtree S et al., 'The Role of Histone Deacetylases in Rheumatoid Arthritis Fibroblast-like Synoviocytes,' Biochem Soc Trans, Jun. 2013 (Jun. 2013), 41(3):783-8.
Hayakawa M et al., 'Synthesis and Biological Evaluation of pyrido[3',2':4,5]furo[3,2-d] Pyrimidine Derivatives as Novel PI3 Kinasae p110alpha Inhibitors,' Bioorg Med Chem Lett, May 1, 2007 (May 1, 2007) Feb. 15, 2007 (Feb. 15, 2007)(ePub), 17(9):2438-42.
Hebbel RP et al., 'The HDAC Inhibitors Trichostatin A and Suberoylanalide Hydroxamic Acid Exhibit Multiple Modalities of Benefit for the Vascular Pathobiology of Sickle Transgenic Mice,' Blood, Mar. 25, 2010 (Mar. 25, 2010) Jan. 6, 2010 (Jan. 6, 2010), 115(12):2483-90.
Imesch P et al., 'Romidepsin Reduces Histone Deacetylase Activity, Induces Acetylation of Histones, Inhibits Proliferation, and Activates Apoptosis in Immortalized Epithelial Endometriotic Cells,' Fertil Steril, Dec. 2010 (Dec. 2010) Jun. 3, 2010 (Jun. 3, 2010)(ePub), 94(7):2838-42.
International Searching Authority, International Preliminary Report on Patentability (Form IB/373) and Written Opinion (Form ISA/237) for International Application No. PCT/GB2010/050116 (Form ISA/210), (Beligny S), completed on Apr. 27, 2012 (Apr. 27, 2012) and dated Aug. 2, 2011 (Aug. 2, 2011), pp. 1-11.
International Searching Authority, International Preliminary Report on Patentability (Form IB/373) and Written Opinion (Form ISA/237) for International Application No. PCT/GB2010/051370 (Form ISA/210), (Helps I), completed on Oct. 28, 2010 (Oct. 28, 2010) and dated Feb. 21, 2012 (Feb. 21, 2012), pp. 1-6.
International Searching Authority, International Preliminary Report on Patentability (Form IB/373) and Written Opinion (Form ISA/237) for International Application No. PCT/GB2011/050824 (Form ISA/210), (Marzi E), completed on Jun. 27, 2011 (Jun. 27, 2011) and dated Nov. 6, 2012 (Nov. 6, 2012), pp. 1-7.
International Searching Authority, International Preliminary Report on Patentability (Form IB/373) and Written Opinion (Form ISA/237) for International Application No. PCT/GB2013/050583 (Form ISA/210), (Wolf C), completed on Apr. 11, 2013 (Apr. 11, 2013) and dated Sep. 9, 2014 (Sep. 9, 2014), pp. 1-6.
International Searching Authority, International Preliminary Report on Patentability (Form IB/373) and Written Opinion (Form ISA/237) for International Application No. PCT/GB2013/052917 (Form ISA/210), (Sotoca Usina E), completed on Jan. 8, 2014 (Aug. 1, 2014) and dated May 12, 2015 (May 12, 2015), pp. 1-11.
International Searching Authority, International Preliminary Report on Patentability (Form IB/373) and Written Opinion (Form ISA/237) for International Application No. PCT/GB2014/051454 (Form ISA/210), (Sotoca Usina E), completed on Jun. 10, 2014 (Jun. 10, 2014) and dated Nov. 10, 2015 (Nov. 10, 2015), pp. 1-7.
International Searching Authority, International Search Report for International Application No. PCT/GB2010/050116 (Form ISA/210), (Beligny S), completed on Apr. 27, 2012 (Apr. 27, 2012) and dated May 10, 2010 (May 10, 2010), pp. 1-6.
International Searching Authority, International Search Report for International Application No. PCT/GB2010/051370 (Form ISA/210), (Helps I), completed on Oct. 28, 2010 (Oct. 28, 2010) and dated Nov. 9, 2010 (Nov. 9, 2010), pp. 1-4.
International Searching Authority, International Search Report for International Application No. PCT/GB2011/050824 (Form ISA/210), (Marzi E), completed on Jun. 27, 2011 (Jun. 27, 2011) and dated Jul. 12, 2011 (Jul. 12, 2011), pp. 1-5.
International Searching Authority, International Search Report for International Application No. PCT/GB2013/050583 (Form ISA/210), (Wolf C), completed on Apr. 11, 2013 (Apr. 11, 2013) and dated May 6, 2013 (May 6, 2013), pp. 1-4.
International Searching Authority, International Search Report for International Application No. PCT/GB2013/052917 (Form ISA/210), (Sotoca Usina E), completed on Jan. 8, 2014 (Jan. 8, 2014) and dated Jan. 22, 2014 (Jan. 22, 2014), pp. 1-9.
International Searching Authority, International Search Report for International Application No. PCT/GB2014/051454 (Form ISA/210), (Sotoca Usina E), completed on Jun. 10, 2014 (Jun. 10, 2014) and dated Jun. 17, 2014 (Jun. 17, 2014), pp. 1-4.
International Searching Authority, International Search Report for International Application No. PCT/GB2015/053256 (Form ISA/210), (Ladenburger C), completed on Nov. 26, 2015 (Nov. 26, 2015) and dated Dec. 8, 2015 (Dec. 8, 2015), pp. 1-7.
International Searching Authority, International Search Report for International Application No. PCT/GB2015/053260 (Form ISA/210), (Ladenburger C), completed on 30 Nov 2015 (30.11.2015) and mailed on 9 Dec 2015 (09.12.2015), pp. 1-9.
International Searching Authority, Written Opinion (Form ISA/237) for International Application No. PCT/GB2015/053256 (Form ISA/210), (Ladenburger C), completed on Nov. 26, 2015 (Nov. 26, 2015) and dated Dec. 8, 2015 (Dec. 8, 2015), pp. 1-6.
International Searching Authority, Written Opinion (Form ISA/237) for International Application No. PCT/GB2015/053260 (Form ISA/210), (Ladenburger C), completed on Nov. 30, 2015 (Nov. 30, 2015) and dated Dec. 9, 2015 (Dec. 9, 2015), pp. 1-7.
Kato K et al., 'Thromboxane Synthetase Inhibitors (TXSI). Design, Synthesis, and Evaluation of Novel Series of Omega-Pyridylalkenoic Acids,' J Med Chem, Mar. 1985 (Mar. 1985), 28(3):287-94.
Kazantsev AG and Thompson LM, 'Therapeutic Application of Histone Deacetylase Inhibitors for Central Nervous System Disorders,' Nat Rev Drug Discov, Oct. 2008 (Oct. 2008), 7(10):854-68.
Kim MG et al., 'The Relationship Between Cisplatin Resistance and Histone Deacetylase Isoform Overexpression in Epithelial Ovarian Cancer Cell Lines,' J Gynecol Oncol, Jul. 2012 (Jul. 2012) Jul. 2, 2012 (Jul. 2, 2012)(ePub), 23(3):182-9.
Kirin SI et al., 'Synthesis and Characterization of Cull Complexes with Amino Acid Substituted di(2-pyridyl)amine Ligands,' Eur J Inorg Chem, Jun. 22, 2007 (Jun. 22, 2007)(ePub), 2007(23):3686-94.

(56) References Cited

OTHER PUBLICATIONS

Kovacs J and Mokhir A, 'Nucleic Acid Controlled Catalysts of Carboxylic Esters Hydrolysis,' Bioorg Med Chem Lett, Nov. 1, 2008 (Nov. 1, 2008) Sep. 27, 2008 (Sep. 27, 2008)(ePub), 18(21):5722-4.
Kovalskiy DA and Perevalov VP, 'Synthesis of 7-(3-piperidyl)-[1,6]naphthyridine and 7-(4-pipe-ridyl)[1,6]naphthyridine,' Chem Hetercycl Comp, Nov. 24, 2009 (Nov. 24, 2009)(ePub), 45(9):1053-7 ISSN:0009-3122.
Kuendgen A et al., 'Treatment of Poor-Risk Myelodysplastic Syndromes and Acute Myeloid Leukemia with a Combination of 5-Azacytidine and Valproic Acid,' Clin Epigenetics, Aug. 2011 (Aug. 2011) Apr. 8, 2011 (Apr. 8, 2011)(ePub), 2(2):389-99.
Lee Su et al., 'In vitro and in vivo Osteogenic Activity of Largazole,' ACS Med Chem Lett, Mar. 10, 2011 (Mar. 10, 2011), 2(3):248-51.
Lemon DD et al., 'Cardiac HDAC6 Catalytic Activity is Induced in Response to Chronic Hypertension,' J Mol Cell Cardiol, Jul. 2011 (Jul. 2011) Apr. 23, 2011 (Apr. 23, 2011)(ePub), 51(1):41-50.
Mai A et al., 'Identification of two new Synthetic Histone Deacetylase Inhibitors that Modulate Globin Gene Expression in Erythroid Cells from Healthy Donors and Patients with Thalassemia,' Mol Pharamcol, Nov. 2007 (Nov. 2007) Jul. 31, 2007 (Jul. 31, 2007)(ePub), 72(5):1111-23.
McGraw AL, 'Romidepsin for the Treatment of T-cell Lymphomas,' Am J Health Syst Pharm, Jul. 1, 2013 (Jul. 1, 2013), 70(13):1115-22.
McKinsey TA, 'The Biology and Therapeutic Implications of HDACs in the Heart,' Handb Exp Pharmacol, 2011 (2011), 206:57-78.
Meredith EL et al., 'Identification of Orally Available Naphthyridine Protein Kinase D Inhibitors,' J Med Chem, Aug. 12, 2010 (Aug. 12, 2010), 53(15):5400-21.
Moradei O et al., 'Histone Deacetylase Inhibitors in Cancer Therapy: New Compounds and Clinical Update of Benzamide-type Agents,' Curr Top Med Chem, 2008 (2008), 8(10):841-58.
Mull RP et al., 'Antihypertensively Active Amidoximes,' J Am Chem Soc, Jul. 1, 1958 (Jul. 1, 1958), 80(14):3769-72.
Nemenoff R, 'Wound Healing: A Role for HDACs in Inhibition of Fibroblast Proliferation Through Repression of PDGF Receptor-alpha. Focus on Repression of PDGF-R-alpha After Cellular Injury Involves TNF-alpha Formation of a c-Fos-YY1 Complex, and Negative Regulation by HDAC,' Am J Physiol Cell Physiol, Jun. 1, 2012 (Jun. 1, 2012) Mar. 28, 2012 (Mar. 28, 2012)(ePub), 302(11):01588-9.
Patra N et al., 'A Novel Histone Deacetylase (HDAC) Inhibitor MHY219 Induces Apoptosis via Up-Regulation of Androgen Receptor Expression in Human Prostate Cancer Cells,' Biomed Pharmacother, Jun. 2013 (Jun. 2013) Feb. 16, 2013 (Feb. 16, 2013)(ePub), 67(5):407-15.
Pham TX and Lee J, 'Dietary Regulation of Histone Acetylases and Deacetylases for the Prevention of Metabolic Diseases,' Nutrients, Nov. 28, 2012 (Nov. 28, 2012), 4(12):1868-86.
Piscopo M et al., 'H3 and H3.3 Histone mRNA Amounts and Ratio in Oral Squamous Cell Carcinoma and Leukoplakia,' Oral Dis, Mar. 2006 (Mar. 2006), 12(2):130-6.
Price S and Dyke HJ, 'Histone Deacetylase Inhibitors: An Analysis of Recent Patenting Activity,' Exp Opin Therap Patents, Aug. 7, 2007 (Aug. 7, 2007)(ePub) 17(7):745-65.
Richardson PG et al., 'Preclinical Data and Early Clinical Experience Supporting the Use of Histone Deacetylase Inhibitors in Multiple Myeloma,' Leuk Res, Jul. 2013 (Jul. 2013) Apr. 9, 2013 (Apr. 9, 2013), 37(7):829-37.
Rotili D et al., 'Non-Cancer Uses of Histone Deacetylase Inhibitors: Effects on Infectious Diseases and beta-Hemoglobinopathies,' Curr Top Med Chem, 2009 (2009), 9(3):272-91.
Saifuddin M et al., 'Water-Accelerated Cationic ?-(7-endo) Cyclisation: Application to Indole-Based Peri-Annulated Polyheterocycles,' Eur J Org Chem, Sep. 2010 (Sep. 2010) Jul. 20, 2010 (Jul. 20, 2010)(ePub), 2010(26):5108-17.

Shanmugam MK and Sethi G, 'Role of Epigenetics in Inflammation-Associated Diseases,' Subcell Biochem, 2013 (2013), 61:627-57 (PubMed ABSTRACT only).
Singh B et al., 'Novel cAMP PDE III Inhibitors: 1,6-naphthyridin-2(1H)-ones,' J Med Chem, Dec. 25, 1992 (Dec. 25, 1992), 35(26):4858-65.
Singh J et al., 'HDAC Inhibitor SAHA Normalizes the Levels of VLCFAs in Human Skin Fibroblasts from X-ALD Patients and Downregulates the Expression of Proinflammatory Cytokines in Abcd1/2-Silenced Mouse Astrocytes,' J Lipid Res, Nov. 2011 (Nov. 2011) Sep. 4, 2011 (Sep. 4, 2011)(ePub), 52(11):2056-69.
Su Gh et al., 'A Novel Histone Deacetylase Inhibitor Identified by High-Throughput Transcriptional Screening of a Compound Library,' Cancer Res, Jun. 15, 2000 (Jun. 15, 2000), 60(12):3137-42.
Suzuki T et al., 'Identification of G Protein-Coupled Receptor 120-Selective Agonists Derived from PPARgamma Agonists,' J Med Chem, Dec. 11, 2008 (Dec. 11, 2008), 51(23):7640-4.
Torrioli M et al., 'Treatment with Valproic Acid Ameliorates ADHD Symptoms in Fragile X Syndrome Boys,' Am J Med Genet A, Jun. 2010 (Jun. 2010), 152A(6):1420-7.
Usui S et al., 'Design, Synthesis, and Biological Activity of Novel PPARgamma Ligands Based on Rosiglitazone and 15d-PGJ2,' Bioorg Med Chem Lett, Mar. 15, (Mar. 15, 2005), 15(6):1547-51.
Van Damme M et al., 'HDAC Isoenzyme Expression is Deregulated in Chronic Lymphocytic Leukemia B-Cells and has a Complex Prognostic Significance,' Epigenetics, Dec. 1, 2012 (Dec. 1, 2012) Oct. 29, 2012 (Oct. 29, 2012), 7(12):1403-12.
Yamamoto T et al., 'Structure-Activity Relationship Study of 1,4-dihydropyridine Derivatives Blocking N-type Calcium Channels,' Bioorg Med Chem Lett, Feb. 15, 2006 (Feb. 15, 2006) Nov. 23, 2005 (Nov. 23, 2005)(ePub), 16(4):798-802.
Ye J, 'Improving Insulin Sensitivity with HDAC Inhibitor,' Diabetes, Mar. 2013 (Mar. 2013), 62(3):685-7.
Zakeeruddin SM et al., 'Glucose Oxidase Mediation by Soluble and Immobilized Electroactive Detergents,' Biosens Bioelectron, 1996 (1996), 11(3):305-15.
Zhang L et al., 'Inhibition of Histone Deacetylase-Induced Myocardial Repair is Mediated by c-Kit in Infarcted Hearts,' J Biol Chem, Nov. 16, 2012 (Nov. 16, 2012) Sep. 28, 2012 (Sep. 28, 2012)(ePub), 287(47):39338-48.
Elslager et al., "Synthesis of 5,5'[[[3-(dimethylamino)propyl]imino]]bis[3-(trichloromethyl)-1,2,4-thiadiazole] and related thiadiazoles as antimalarial agents." Journal of Heterocyclic Chemistry 1973, 10, 611-622.
Lee et al., "Synthesis and photophysical properties of five-membered ring π-conjugated materials based on bisthiazol-2-yl-amine and their metal complexation studies." Tertahedron. 2010, 66, 9440-9444.
Somei et al. "Boronation-thallation, a new approach to the synthesis of indoles having aryl, and/or a heteroaryl substituent at the 4-position." Chem. Pharm. Bull. 34(9), 3971-3973, (1986).
Anonymous, PubChem, '3-(1H-Indol-3-yl)-3-(pyridin-4-yl)propionic acid—Compound Summary,' CID 4715104, AC1NFWP0, MolPort-000-861-678, BBL022406, STK895679, AKOS000266205, MCULE-7014658967, 3-(1H-indol-3-yl)-3-pyridin-3-ylpropanoic acid, Sep. 17, 2005 (Sep. 17, 2005), National Center for Biotechnology Information, U.S. National Library of Medicine, Bethesda, MD (Publ), pp. 1-6 XP-002718389.
Anonymous, PubChem, '3-(1H-Indol-3-yl)-3-pyridin-4-yl-propionic acid—Compound,' CID 3157817, ST073698 3-(1H-indol-3-yl)-3-pyridin-4-ylpropanoic acid, 3-(1H-indol-3-yl)-3-(pyridin-4-yl)propanoic acid, Aug. 10, 2005 (Aug. 10, 2005), National Center for Biotechnology Information, U.S. National Library of Medicine, Bethesda, MD (Publ), pp. 1-7 XP-002718387.
Anonymous, PubChem, 'AC1LLZ4B—Compound Summary,' CID 1092973, (3S)-3-(1H-indol-3-yl)-3-pyridin-4-ylpropanoic acid, Jul. 10, 2005 (Jul. 10, 2005), National Center for Biotechnology Information, U.S. National Library of Medicine, Bethesda, MD (Publ), pp. 1-5 XP-002718385.
Anonymous, PubChem, 'AC1LLZ4D—Compound Summary, CID 1092974, (3R)-3-(1H-indol-3-yl)-3-pyridin-4-ylpropanoic acid,'

(56) References Cited

OTHER PUBLICATIONS

Jul. 10, 2005 (Jul. 10, 2005), National Center for Biotechnology Information, U.S. National Library of Medicine, Bethesda, MD (Publ), pp. 1-5 XP-002718386.

Anonymous, PubChem, 'CID 40480236—Compound Summary,' CID 40480236, (3R)-3-(1H-indol-3-yl)-3-pyridin-3-ylpropanoic acid, May 30, 2009 (May 30, 2009), National Center for Biotechnology Information, U.S. National Library of Medicine, Bethesda, MD (Publ), pp. 1-4 XP-002718391.

Anonymous, PubChem, 'ethyl 2 [pyridine-4-yl(pyrrol-1-yl)amino]acetate; hydrochloride,' CID 67857985, Nov. 30, 2012 (Nov. 30, 2012), National Center for Biotechnology Information, U.S. National Library of Medicine, Bethesda, MD (Publ), pp. 1-5 XP-002718393.

Anonymous, PubChem, 'SureCN2072816—Compound Summary,' CID 58088407, 3-(4-methoxy-1H-indol-3-yl)-3-pyridin-4-ylpropanoic acid, Aug. 19, 2012 (Aug. 19, 2012), National Center for Biotechnology Information, U.S. National Library of Medicine, Bethesda, MD (Publ), pp. 1-5 XP-002718392.

Anonymous, PubChem, 'SureCN9469183—Compound Summary,' CID 14373294, ethyl 2[pyridine-4-yl(pyrrol-1-yl)amino]acetate, Feb. 9, 2007 (Feb. 9, 2007), National Center for Biotechnology Information, U.S. National Library of Medicine, Bethesda, MD (Publ), pp. 1-5 XP-002718390.

Bruijnincx PC et al., 'Modeling the 2-His-1-carboxylate Facial Triad: Iron-catecholato Complexes as Structural and Functional Models of the Extrodiol Cleaving Dioxygenases,' J Am Chem Soc, Feb. 28, 2007 (Feb. 28, 2007) Feb. 1, 2007 (Feb. 1, 2007)(ePub), 129(8):2275-86.

Díez-Barra E et al., 'Double Michael Addition of Azoles to Methyl Propiolate: A Straightforward Entry to Ligands With Two Heterocyclic Rings,' Tetrahedron Lett, Aug. 7, 2004 (Aug. 7, 2004)(ePub), 45(2004):6937-9.

Falkenberg et al. Nature Reviews Drug Discovery, vol. 13, 673-691, 2014.

Giannini G et al., 'Exploring bis-(indolyl)methane Moiety as an Alternative and Innovative CAP Group in the Design of Histone Deacetylase (HDAC) Inhibitors,' Bioorg Med Chem Lett, May 15, 2009 (May 15, 2009) Mar. 26, 2009 (Feb. 26, 2009)(ePub), 19(10):2840-3.

Grattagliano I et al., 'Glutathione Peroxidase, Thioredoxin, and Membrane Protein Changes in Erythrocytes Predict Ribavirin-Induced Anemia,' Clin Pharmacol Ther, Oct. 2005 (Oct. 2005), 78(4):422-32.

Lobera et al., "Selective class IIa deacetylase inhibition via a nonchelating zinc-binding group." Nat. Chem. Biol. 2013, 9, 319-325.

Lu W et al., 'Pd-Catalyzed Selective Addition of Heteroaromatic C—H Bonds to C—C Triple Bonds Under Mild Conditions,' Org Lett, Sep. 21, 2000 (Sep. 21, 2000), 2(19):2927-30.

Ohashi A et al., 'Covalent Linking of Coordination-Organized Slipped Cofacial Porphyrin Dimers,' Bull Chem Soc Jpn, Feb. 10, 2004 (Feb. 10, 2004)(ePub), 77(2004):365-74.

Oyamada J and Kitamura T, 'Pt(II)-Catalyzes Hydroarylation Reaction of Alkynes with Pyrroles and Furans,' Tetrahedron, Mar. 14, 2009 (Mar. 14, 2009)(ePub), 65(2009):3842-7.

Peters L et al., 'Synthesis and Transition Metal Complexes of 3,3-bis(1-vinylimidazol-2-yl)propionic Acid, A New N,N,O Ligand Suitable for Copolymerisation,' Inorg Chim Acta, Mar. 12, 2011 (Mar. 12, 2011), 374(2011):392-40.

Peters L et al., 'The New Facial Tripod Ligand 3,3-bis(1-methylimidazol-2-yl)propionic Acid and Carbonyl Complexes Thereof Containing Manganese and Rhenium,' J Organomet Chem, Nov. 25, 2004 (Nov. 25, 2004), 690(2005):2009-16.

Safdy ME et al., 'Tryptophan Analogues. 1. Synthesis and Antihypertensive Activity of Positional Isomers,' J Med Chem, Jun. 1982 (Jun. 1982), 25(6):723-30.

* cited by examiner

HISTONE DEACETYLASE INHIBITORS

CROSS-REFERENCE TO RELATED APPLICATIONS

This application is the national phase of International Patent Application No. PCT/GB2014/051454, filed May 12, 2014, which claims priority to applications GB1308409.0, filed May 10, 2013, and GB1315253.3, filed Aug. 28, 2013, the entire disclosure of each of which is incorporated by reference herein.

FIELD OF THE INVENTION

The present invention relates to novel compounds which are inhibitors of histone deacetylase (HDAC) and therefore have therapeutic utility.

BACKGROUND OF THE INVENTION

HDACs are zinc metalloenzymes that catalyse the hydrolysis of acetylated lysine residues. In histones, this returns lysines to their protonated state and is a global mechanism of eukaryotic transcriptional control, resulting in tight packaging of DNA in the nucleosome. Additionally, reversible lysine acetylation is an important regulatory process for non-histone proteins. Thus, compounds which are able to modulate HDAC have important therapeutic potential.

WO2010/086646 discloses compounds which act as inhibitors of HDAC. The heteroaryl capping groups and the zinc-binding groups are joined via an alkylene linker.

SUMMARY OF THE INVENTION

A compound of the formula

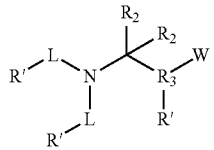

or a pharmaceutically acceptable salt thereof, wherein:
each $R'$ is independently selected from H and $QR_1$;
each Q is independently selected from a bond, CO, $CO_2$, NH, S, SO, $SO_2$ or O;
each $R_1$ is independently selected from H, $C_1$-$C_{10}$ alkyl, $C_2$-$C_{10}$ alkenyl, $C_2$-$C_{10}$ alkynyl, aryl, heteroaryl, $C_1$-$C_{10}$ cycloalkyl, halogen, $C_1$-$C_{10}$ alkylaryl, $C_1$-$C_{10}$ alkyl heteroaryl or $C_1$-$C_{10}$ heterocycloalkyl;
each L is independently selected from a 5 to 10-membered nitrogen-containing heteroaryl;
W is a zinc-binding group;
each $R_2$ is independently hydrogen or $C_1$ to $C_6$ alkyl; and
$R_3$ is an aryl or heteroaryl;
each aryl or heteroaryl may be substituted by up to three substituents selected from $C_1$-$C_6$ alkyl, hydroxy, $C_1$-$C_3$ hydroxyalkyl, $C_1$-$C_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl) amino $C_1$-$C_3$ alkyl, bis($C_1$-$C_3$ alkyl) amino $C_1$-$C_3$ alkyl, $C_1$-$C_3$-acylamino, $C_1$-$C_3$ alkyl sulfonylamino, halo, nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl and bis $C_1$-$C_3$-alkyl aminosulfonyl; and
each alkyl, alkenyl or alkynyl may be substituted with halogen, $NH_2$, $NO_2$ or hydroxyl.

These compounds have been surprisingly found to be potent HDAC inhibitors, which are highly selective for HDAC6 over HDAC1.

DESCRIPTION OF THE INVENTION

Definitions

As used herein, "alkyl" means a $C_1$-$C_{10}$ alkyl group, which can be linear or branched. Preferably, it is a $C_1$-$C_6$ alkyl moiety. More preferably, it is a $C_1$-$C_4$ alkyl moiety. Examples include methyl, ethyl, n-propyl and t-butyl. It may be divalent, e.g. propylene.

As used herein, "cycloalkyl" contains from 3 to 10 carbon atoms. It may be monovalent or divalent.

As used herein, "alkenyl" means a $C_2$-$C_{10}$ alkenyl group. Preferably, it is a $C_2$-$C_6$ alkenyl group. More preferably, it is a $C_2$-$C_4$ alkenyl group. The alkenyl radicals may be mono- or di-saturated, more preferably monosaturated. Examples include vinyl, allyl, 1-propenyl, isopropenyl and 1-butenyl. It may be divalent, e.g. propenylene As used herein, "alkynyl" is a $C_2$-$C_{10}$ alkynyl group which can be linear or branched. Preferably, it is a $C_2$-$C_4$ alkynyl group or moiety. It may be divalent.

Each of the $C_1$-$C_{10}$ alkyl, $C_2$-$C_{10}$ alkenyl and $C_2$-$C_{10}$ alkynyl groups may be optionally substituted with each other, i.e. $C_1$-$C_{10}$ alkyl optionally substituted with $C_2$-$C_{10}$ alkenyl. They may also be optionally substituted with aryl, cycloalkyl (preferably $C_3$-$C_{10}$), aryl or heteroaryl. They may also be substituted with halogen (e.g. F, Cl), $NH_2$, $NO_2$ or hydroxyl. Preferably, they may be substituted with up to 10 halogen atoms or more preferably up to 5 halogens. For example, they may be substituted by 1, 2, 3, 4 or 5 halogen atoms. Preferably, the halogen is fluorine. For example, $C_1$-$C_{10}$ alkyl may be $CF_3$, $CHF_2$, $CH_2CF_3$, $CH_2CHF_2$ or $CF_2CF_3$ or $OCF_3$, $OCHF_2$, $OCH_2CF_3$, $OCH_2CHF_2$ or $OCF_2CF_3$.

As used herein, "aryl" means a monocyclic, bicyclic, or tricyclic monovalent or divalent (as appropriate) aromatic radical, such as phenyl, biphenyl, naphthyl, anthracenyl, which can be optionally substituted with up to three substituents preferably selected from the group of $C_1$-$C_6$ alkyl, hydroxy, $C_1$-$C_3$ hydroxyalkyl, $C_1$-$C_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl) amino $C_1$-$C_3$ alkyl, bis($C_1$-$C_3$ alkyl) amino $C_1$-$C_3$ alkyl, $C_1$-$C_3$-acylamino, $C_1$-$C_3$ alkyl sulfonylamino, halo, nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl and bis $C_1$-$C_3$-alkyl aminosulfonyl.

Amino means —$NH_2$.

As used herein, heteroaryl means a monocyclic, bicyclic or tricyclic monovalent or divalent (as appropriate) aromatic radical containing up to four heteroatoms selected from oxygen, nitrogen and sulfur, such as thiazolyl, tetrazolyl, imidazolyl, oxazolyl, isoxazolyl, thienyl, pyrazolyl, pyridinyl, pyrazinyl, pyrimidinyl, indolyl, quinolyl, isoquinolyl, said radical being optionally substituted with up to three substituents preferably selected from the group of $C_1$-$C_6$ alkyl, hydroxy, $C_1$-$C_3$ hydroxyalkyl, $C_1$-$C_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl) amino $C_1$-$C_3$ alkyl, bis ($C_1$-$C_3$ alkyl) amino $C_1$-$C_3$ alkyl, $C_1$-$C_3$-acylamino, $C_1$-$C_3$ alkyl sulfonylamino, halo, nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl and bis $C_1$-$C_3$-alkyl aminosulfonyl.

In the compounds of the invention, certain heteroaryl groups (i.e. L and $R_3$) are attached to R'. However, they may still be substituted by up to three additional substituents, selected from the groups defined above. Preferably, R' is the only substituent.

As used herein, the term heterocycle or heterocycloalkyl is a mono- or di-valent carbocyclic radical containing up to 4 heteroatoms selected from oxygen, nitrogen and sulfur. It may be bicyclic or monocyclic. It is preferably saturated. The word 'linker' has been used herein to mean di-valent. If the heterocycle is a di-valent linker, the heterocycle may be attached to neighbouring groups through a carbon atom, or through on of the heteroatoms, e.g. a N. Examples of heterocycles are piperazine and morpholine.

The heterocyclic ring may be mono- or di-unsaturated. The radical may be optionally substituted with up to three substituents independently selected from $C_1$-$C_6$ alkyl, hydroxy, $C_1$-$C_3$ hydroxyalkyl, $C_1$-$C_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl) amino $C_1$-$C_3$ alkyl, bis ($C_1$-$C_3$ alkyl) amino $C_1$-$C_3$ alkyl, $C_1$-$C_3$-acylamino, $C_1$-$C_3$ alkyl sulfonylamino, halo e.g. F, nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl and bis $C_1$-$C_3$-alkyl aminosulfonyl.

As used herein, the above groups can be followed by the suffix -ene. This means that the group is divalent, i.e. a linker group.

As used herein, "thiol-protecting group" is typically:

(a) a protecting group that forms a thioether to protect a thiol group, for example a benzyl group which is optionally substituted by $C_1$-$C_6$ alkoxy (for example methoxy), $C_1$-$C_6$ acyloxy (for example acetoxy), hydroxy and nitro, picolyl, picolyl-N-oxide, anthrylmethyl, diphenylmethyl, phenyl, t-butyl, adamantyl, $C_1$-$C_6$ acyloxymethyl (for example pivaloyloxymethyl, tertiary butoxycarbonyloxymethyl);

(b) a protecting group that forms a monothio, dithio or aminothioacetal to protect a thiol group, for example $C_1$-$C_6$ alkoxymethyl (for example methoxymethyl, isobutoxymethyl), tetrahydropyranyl, benzylthiomethyl, phenylthiomethyl, thiazolidine, acetamidemethyl, benzamidomethyl;

(c) a protecting group that forms a thioester to protect a thiol group, such as tertiary-butyloxycarbonyl (BOC), acetyl and its derivatives, benzoyl and its derivatives; or (d) a protecting group that forms a carbamic acid thioester to protect a thiol group, such as carbamoyl, phenylcarbamoyl, $C_1$-$C_6$ alkylcarbamoyl (for example methylcarbamoyl and ethylcarbamoyl).

Preferred Groups of the Invention

Preferably, at least one $R_2$ is H. Preferably, both $R_2$ groups are H.

The group W is a zinc-chelating residue, i.e. a metallophile capable of binding with zinc in the active site of HDAC. Suitable metallophiles are known to those skilled in the art.

In a preferred embodiment, W is selected from:

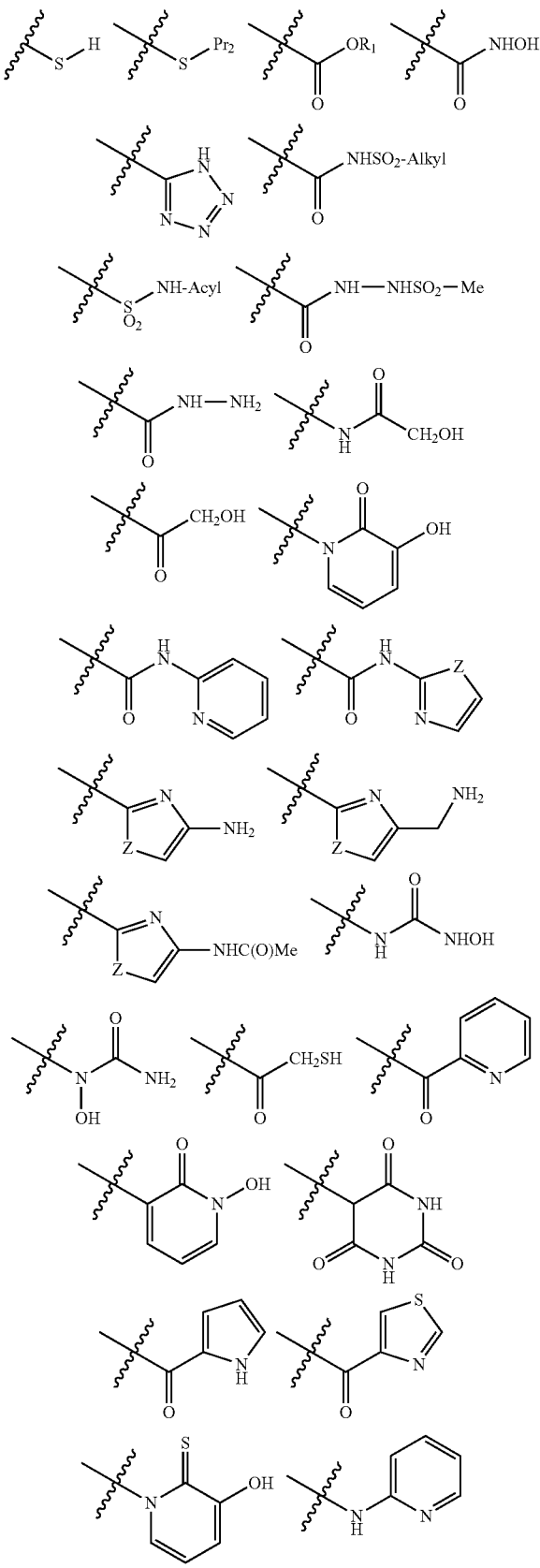

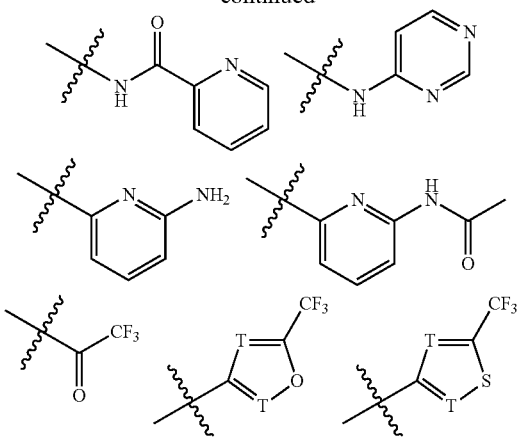

wherein R₁ is as defined in claim 1, Pr² is H or a thiol protecting group, Z is selected from O, S or NH and T is N or CH.

When W is COOR₁, preferably R₁ is not halogen. More preferably, when W is COOR₁, R₁ is H or $C_1$-$C_{10}$ alkyl.

Preferably, W is —COOH, —CONHOH, CONHSO₂CH₃, —CONHNHSO₂CH₃, —CONHNH₂, —CONH(2-pyridyl), —NHCONHOH, tetrazole, hydroxypyridin-2-thione or hydroxypyridin-2-one. Preferably W is not COOR₁. More preferably, W is COOMe, —CONHOH, CONHSO₂CH₃, —CONHNHSO₂CH₃, —CONHNH₂, —CONH(2-pyridyl)-NHCONHOH, tetrazole, hydroxypyridin-2-thione or hydroxypyridin-2-one. Even more preferably, W is —CONHOH, tetrazole, hydroxypyridin-2-thione or hydroxypyridin-2-one. Most preferably, W is —CONHOH.

In a preferred embodiment, in at least one, preferably both L groups, the atom that is directly bonded to X is a carbon, and at least one nitrogen atom is directly bonded to said carbon.

In an embodiment, at least one L group is a 5-membered heteroaryl. Preferably, at least one L group is a 6-membered heteroaryl. Even more preferably, both L groups are a 6-membered heteroaryl.

Preferably, at least one L group is pyridinyl, pyrimidinyl, pyridazinyl, oxadiazolyl, pyrazolyl, thiadiazolyl, pyrazinyl, benzofused thiazolyl, benzofused oxazolyl or benzofused imidazolyl. More preferably, at least one L group is pyridyl or pyrazinyl. Most preferably, one L is pyrazinyl and one L is pyridyl. Preferably, when L is pyridyl, it is substituted with a heteroaryl group. The heteroaryl group is preferably an optionally substituted (preferably substituted) pyridine.

Preferably, at least one L group is pyridinyl, oxadiazolyl, pyrazolyl, thiadiazolyl, pyrazinyl, benzofused thiazolyl, benzofused oxazolyl or benzofused imidazolyl.

Preferably, at least one L group is a 5 or 6-membered heteroaryl, which is optionally fused to a benzene.

Preferably, Q is a bond or O.

Preferably, R₃ is aryl. More preferably, R₃ is phenylene or phenylene substituted with a halogen.

Preferably, at least one, preferably both, R₂ is H.

In a preferred embodiment, at least one R' is H, halogen, CF₃, $C_1$-$C_6$ alkyl, aryl optionally substituted with halogen or heteroaryl optionally substituted with halogen. Preferably, the alkyl is substituted with at least one halogen, which is preferably fluorine.

In a preferred embodiment, the R' attached to R₃ is hydrogen or halogen. Preferably, R₃ is hydrogen or fluorine.

More preferably, the R' attached to R₃ is hydrogen. In a preferred embodiment, at least one R', and preferably at least one of the R' that is attached to L, is H, $C_1$-$C_{10}$ alkyl or O—($C_1$-$C_{10}$ alkyl). Preferably, at least one R' is substituted or unsubstituted aryl or O-(substituted or unsubstituted aryl). Preferably, at least one R' is aryl or O-aryl, each of which may be substituted with a halogen, amino or $C_1$-$C_{10}$ alkyl. The aryl may be substituted in any position. The aryl may be mono-, bis-, or tri-substituted.

In a preferred embodiment, at least one R', and preferably at least one of the R' that is attached to L, is H, $C_1$-$C_{10}$ alkyl or O—($C_1$-$C_{10}$ alkyl), halogen, $C_1$-$C_{10}$ heterocycloalkyl, aryl (preferably optionally substituted phenyl), trifluoromethyl or heteroaryl, preferably heteroaryl. Preferably, when R' is heteroaryl, it is optionally substituted pyridyl, preferably a substituted pyridyl.

In one embodiment, at least one R' that is attached to L is OCH₃ or CH₃. Preferably, at least one of the R' that is attached to L is heterocycloalkyl. Preferably, the heterocycloalkyl is morpholino.

In a preferred embodiment, when Q is a direct bond, R₁ is H, $C_1$-$C_{10}$ alkyl or O—($C_1$-$C_{10}$ alkyl), halogen (preferably F), $C_1$-$C_{10}$ heterocycloalkyl (preferably morpholino), aryl (preferably optionally substituted phenyl), trifluoromethyl or heteroaryl, preferably heteroaryl. Preferably, when R₁ is heteroaryl, it is optionally substituted pyridyl, preferably a substituted pyridyl.

In a preferred embodiment, R₁ is $C_1$-$C_{10}$ alkyl, $C_2$-$C_{10}$ alkenyl or $C_2$-$C_{10}$ alkynyl, preferably those groups are substituted with halogen, NH₂, NO₂ or hydroxyl. More preferably, when R' or R₁ is $C_1$-$C_{10}$ alkyl, it may be substituted with halogen which is preferably fluorine. The $C_1$-$C_{10}$ alkyl group may be substituted by up to 10 halogen atoms or preferably, by up to 5 halogen atoms, i.e., 1, 2, 3, 4 or 5 halogen atoms. For example, R' or R₁ may be CF₃, CHF₂, CH₂CF₃, CH₂CHF₂ or CF₂CF₃ or OCF₃, OCHF₂, OCH₂CF₃, OCH₂CHF₂ or OCF₂CF₃.

R' may be substituted onto any of the ring atoms of the L group or onto any of the ring atoms of the R₂ group.

Preferably, the L and R₃ groups have no other substitutions other than R'.

Preferably, Q is a direct bond.

Preferably, in addition to a N atom, L contains at least one other heteroatom in the heteroaryl ring which is selected from N, O or S.

In a preferred embodiment, L is:

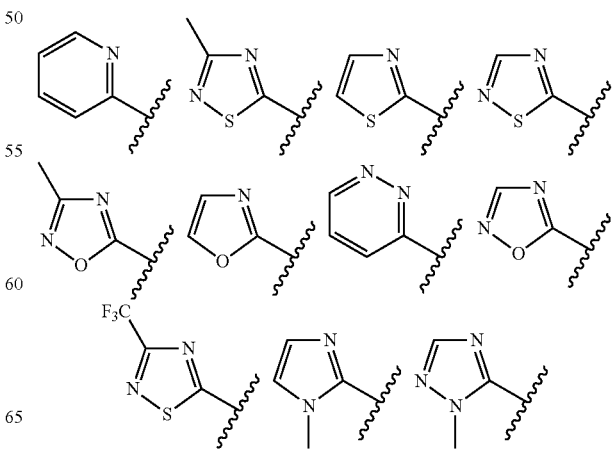

-continued

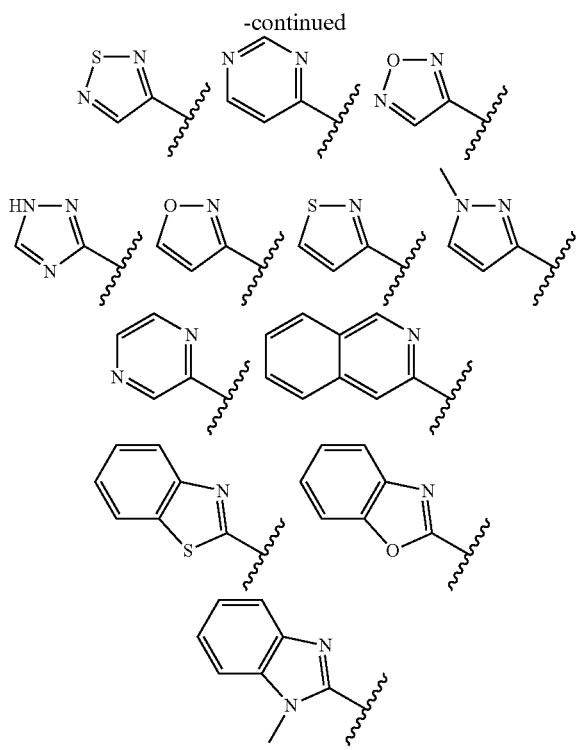

In a preferred embodiment, L is a hydrogen bond-acceptor, and preferably not also a hydrogen bond donor. Preferably, L does not have a hydrogen atom attached to an electronegative atom, such as N or O.

The definition of hydrogen bond acceptors/donors is known to those skilled in the art. For example, a hydrogen bond donor will have a hydrogen attached to an electronegative atom, such as N or O. For example, a hydrogen bond acceptor will have a N or O, which has a free lone pair.

Preferably the atom of L that is directly bonded to the N atom of the formula of claim 1 is carbon, and at least one nitrogen atom is directly bonded to said carbon (preferably via a double bond). More preferably, said nitrogen atom is a hydrogen bond acceptor.

A pharmaceutical composition of the invention comprises a compound as defined above, and a pharmaceutically acceptable carrier or diluent. A pharmaceutical composition of the invention typically contains up to 85 wt % of a compound of the invention. More typically, it contains up to 50 wt % of a compound of the invention. Preferred pharmaceutical compositions are sterile and pyrogen-free. Further, the pharmaceutical compositions provided by the invention typically contain a compound of the invention which is a substantially pure optical isomer. Preferably, the pharmaceutical composition comprises a pharmaceutically acceptable salt form of a compound of the invention.

As used herein, a pharmaceutically acceptable salt is a salt with a pharmaceutically acceptable acid or base. Pharmaceutically acceptable acids include both inorganic acids such as hydrochloric, sulfuric, phosphoric, diphosphoric, hydrobromic or nitric acid and organic acids such as citric, fumaric, maleic, malic, ascorbic, succinic, tartaric, benzoic, acetic, methanesulfonic, ethanesulfonic, ethanedisulfonic, salicylic, stearic, benzenesulfonic or p-toluenesulfonic acid. Pharmaceutically acceptable bases include alkali metal (e.g. sodium or potassium) and alkali earth metal (e.g. calcium or magnesium) hydroxides and organic bases such as alkyl amines, aryl amines or heterocyclic amines.

For the avoidance of doubt, the present invention also embraces pro-drugs which react in vivo to give a compound of the present invention.

The compounds of the present invention are found to be inhibitors of HDAC. The compounds of the present invention are therefore therapeutically useful in the treatment of conditions affected by HDAC activity.

The compounds of the invention may be prepared by synthetic routes that will be apparent to those skilled in the art, e.g. based on the Examples.

The compounds of the present invention are found to be inhibitors of HDAC. The compounds of the present invention are therefore therapeutically useful.

The compounds of the invention and compositions comprising them may be administered in a variety of dosage forms. In one embodiment, a pharmaceutical composition comprising a compound of the invention may be formulated in a format suitable for oral, rectal, parenteral, intranasal or transdermal administration or administration by inhalation or by suppository. Typical routes of administration are parenteral, intranasal or transdermal administration or administration by inhalation.

The compounds of the invention can be administered orally, for example as tablets, troches, lozenges, aqueous or oily suspensions, dispersible powders or granules. Preferred pharmaceutical compositions of the invention are compositions suitable for oral administration, for example tablets and capsules.

The compounds of the invention may also be administered parenterally, whether subcutaneously, intravenously, intramuscularly, intrasternally, transdermally or by infusion techniques. The compounds may also be administered as suppositories.

The compounds of the invention may also be administered by inhalation. An advantage of inhaled medications is their direct delivery to the area of rich blood supply in comparison to many medications taken by oral route. Thus, the absorption is very rapid as the alveoli have an enormous surface area and rich blood supply and first pass metabolism is bypassed. A further advantage may be to treat diseases of the pulmonary system, such that delivering drugs by inhalation delivers them to the proximity of the cells which are required to be treated.

The present invention also provides an inhalation device containing such a pharmaceutical composition. Typically said device is a metered dose inhaler (MDI), which contains a pharmaceutically acceptable chemical propellant to push the medication out of the inhaler.

The compounds of the invention may also be administered by intranasal administration. The nasal cavity's highly permeable tissue is very receptive to medication and absorbs it quickly and efficiently, more so than drugs in tablet form. Nasal drug delivery is less painful and invasive than injections, generating less anxiety among patients. By this method absorption is very rapid and first pass metabolism is usually bypassed, thus reducing inter-patient variability. Further, the present invention also provides an intranasal device containing such a pharmaceutical composition.

The compounds of the invention may also be administered by transdermal administration. The present invention therefore also provides a transdermal patch containing a compound of the invention.

The compounds of the invention may also be administered by sublingual administration. The present invention therefore also provides a sub-lingual tablet comprising a compound of the invention.

A compound of the invention may also be formulated with an agent which reduces degradation of the substance by processes other than the normal metabolism of the patient, such as anti-bacterial agents, or inhibitors of protease enzymes which might be the present in the patient or in commensural or parasite organisms living on or within the patient, and which are capable of degrading the compound.

Liquid dispersions for oral administration may be syrups, emulsions and suspensions.

Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for injection or infusion may contain as carrier, for example, sterile water or preferably they may be in the form of sterile, aqueous, isotonic saline solutions.

In one embodiment the compounds of the present invention may be used in combination with another known inhibitor of HDAC, such as SAHA. In this embodiment, the combination product may be formulated such that it comprises each of the medicaments for simultaneous, separate or sequential use.

The compounds of the present invention can be used in both the treatment and prevention of cancer and can be used in a monotherapy or in a combination therapy. When used in a combination therapy, the compounds of the present invention are typically used together with small chemical compounds such as platinum complexes, anti-metabolites, DNA topoisomerase inhibitors, radiation, antibody-based therapies (for example herceptin and rituximab), anti-cancer vaccination, gene therapy, cellular therapies, hormone therapies or cytokine therapy.

In one embodiment of the invention a compound of the invention is used in combination with another chemotherapeutic or antineoplastic agent in the treatment of a cancer. Examples of such other chemotherapeutic or antineoplastic agents include platinum complexes including cisplatin and carboplatin, mitoxantrone, vinca alkaloids for example vincristine and vinblastine, anthracycline antibiotics for example daunorubicin and doxorubicin, alkylating agents for example chlorambucil and melphalan, taxanes for example paclitaxel, antifolates for example methotrexate and tomudex, epipodophyllotoxins for example etoposide, camptothecins for example irinotecan and its active metabolite SN38 and DNA methylation inhibitors for example the DNA methylation inhibitors disclosed in WO02/085400.

According to the invention, therefore, products are provided which contain a compound of the invention and another chemotherapeutic or antineoplastic agent as a combined preparation for simultaneous, separate or sequential use in alleviating a cancer. Also provided according to the invention is the use of compound of the invention in the manufacture of a medicament for use in the alleviation of cancer by co-administration with another chemotherapeutic or antineoplastic agent. The compound of the invention and the said other agent may be administrated in any order. In both these cases the compound of the invention and the other agent may be administered together or, if separately, in any order as determined by a physician.

HDAC is believed to contribute to the pathology and/or symptomology of several different diseases such that reduction of the activity of HDAC in a subject through inhibition of HDAC may be used to therapeutically address these disease states. Examples of various diseases that may be treated using the HDAC inhibitors of the present invention are described herein.

One set of indications that HDAC inhibitors of the present invention may be used to treat is those involving undesirable or uncontrolled cell proliferation. Such indications include benign tumours, various types of cancers such as primary tumours and tumour metastasis, restenosis (e.g. coronary, carotid, and cerebral lesions), abnormal stimulation of endothelial cells (atherosclerosis), insults to body tissue due to surgery, abnormal wound healing, abnormal angiogenesis, diseases that produce fibrosis of tissue, repetitive motion disorders, disorders of tissues that are not highly vascularized, and proliferative responses associated with organ transplants. More specific indications for HDAC inhibitors include, but are not limited to prostate cancer, lung cancer, acute leukaemia, multiple myeloma, bladder carcinoma, renal carcinoma, breast carcinoma, colorectal carcinoma, neuroblastoma and melanoma.

In one embodiment, a method is provided for treating diseases associated with undesired and uncontrolled cell proliferation. The method comprises administering to a subject suffering from uncontrolled cell proliferation a therapeutically effective amount of a HDAC inhibitor according to the present invention, such that said uncontrolled cell proliferation is reduced. The particular dosage of the inhibitor to be used will depend on the severity of the disease state, the route of administration, and related factors that can be determined by the attending physician. Generally, acceptable and effective daily doses are amounts sufficient to effectively slow or eliminate uncontrolled cell proliferation.

HDAC inhibitors according to the present invention may also be used in conjunction with other agents to inhibit undesirable and uncontrolled cell proliferation. Examples of other anti-cell proliferation agents that may be used in conjunction with the HDAC inhibitors of the present invention include, but are not limited to, retinoid acid and derivatives thereof, 2-methoxyestradiol, Angiostatin™ protein, Endostatin™ protein, suramin, squalamine, tissue inhibitor of metalloproteinase-I, tissue inhibitor of metalloproteinase-2, plasminogen activator inhibitor-1, plasminogen activator inhibitor-2, cartilage-derived inhibitor, paclitaxel, platelet factor 4, protamine sulfate (clupeine), sulfated chitin derivatives (prepared from queen crab shells), sulfated polysaccharide peptidoglycan complex (sp-pg), staurosporine, modulators of matrix metabolism, including for example, proline analogs ((1-azetidine-2-carboxylic acid (LACA), cishydroxyproline, d,l-3,4-dehydroproline, thiaproline), beta-aminopropionitrile fumarate, 4-propyl-5-(4-pyridinyl)-2(3H)-oxazolone; methotrexate, mitoxantrone, heparin, interferons, 2 macroglobulin-serum, chimp-3, chymostatin, beta-cyclodextrin tetradecasulfate, eponemycin; fumagillin, gold sodium thiomalate, d-penicillamine (CDPT), beta-1-anticollagenase-serum, alpha-2-antiplasmin, bisantrene, lobenzarit disodium, n-(2-carboxyphenyl-4-chloroanthronilic acid disodium or "CCA", thalidomide; angiostatic steroid, carboxyaminoimidazole; metalloproteinase inhibitors such as BB94. Other anti-angiogenesis agents that may be used include antibodies, preferably monoclonal antibodies against these angiogenic growth factors: bFGF, aFGF, FGF-5, VEGF isoforms, VEGF-C, HGF/SF and Ang-1/Ang- 2. Ferrara N. and Alitalo, K. "Clinical application of angiogenic growth factors and their inhibitors" (1999) Nature Medicine 5:1359-1364.

Generally, cells in benign tumours retain their differentiated features and do not divide in a completely uncontrolled manner. A benign tumour is usually localized and nonmetastatic. Specific types of benign tumours that can be treated using HDAC inhibitors of the present invention include hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas and pyogenic granulomas.

In the case of malignant tumors, cells become undifferentiated, do not respond to the body's growth control signals, and multiply in an uncontrolled manner. Malignant tumors are invasive and capable of spreading to distant sites (metastasizing). Malignant tumors are generally divided into two categories: primary and secondary. Primary tumors arise directly from the tissue in which they are found. Secondary tumours, or metastases, are tumours that originated elsewhere in the body but have now spread to distant organs. Common routes for metastasis are direct growth into adjacent structures, spread through the vascular or lymphatic systems, and tracking along tissue planes and body spaces (peritoneal fluid, cerebrospinal fluid, etc.).

Specific types of cancers or malignant tumours, either primary or secondary, that can be treated using the HDAC inhibitors of the present invention include, but are not limited to, leukaemia, breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumour, small-cell lung tumour, gallstones, islet cell tumour, primary brain tumour, acute and chronic lymphocytic and granulocytic tumours, hairy-cell tumour, adenoma, hyperplasia, medullary carcinoma, pheochromocytoma, mucosal neuromas, intestinal ganglloneuromas, hyperplastic corneal nerve tumour, marfanoid habitus tumour, Wilms' tumour, seminoma, ovarian tumour, leiomyomater tumour, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumour, polycythermia vera, adenocarcinoma, glioblastoma multiforme, leukemias, lymphomas, malignant melanomas, epidermoid carcinomas, and other carcinomas and sarcomas.

The HDAC inhibitors of the present invention may also be used to treat abnormal cell proliferation due to insults to body tissue during surgery. These insults may arise as a result of a variety of surgical procedures such as joint surgery, bowel surgery, and cheloid scarring. Diseases that produce fibrotic tissue that may be treated using the HDAC inhibitors of the present invention include emphysema. Repetitive motion disorders that may be treated using the present invention include carpal tunnel syndrome. An example of a cell proliferative disorder that may be treated using the invention is a bone tumour.

Proliferative responses associated with organ transplantation that may be treated using HDAC inhibitors of the invention include proliferative responses contributing to potential organ rejections or associated complications. Specifically, these proliferative responses may occur during transplantation of the heart, lung, liver, kidney, and other body organs or organ systems.

Abnormal angiogenesis that may be treated using this invention include those abnormal angiogenesis accompanying rheumatoid arthritis, ischemic-reperfusion related brain edema and injury, cortical ischemia, ovarian hyperplasia and hypervascularity, polycystic ovary syndrome, endometriosis, psoriasis, diabetic retinopathy, and other ocular angiogenic diseases such as retinopathy of prematurity (retrolental fibroplastic), macular degeneration, corneal graft rejection, neuroscular glaucoma and Oster Webber syndrome.

Examples of diseases associated with uncontrolled angiogenesis that may be treated according to the present invention include, but are not limited to retinal/choroidal neovascularization and corneal neovascularization. Examples of diseases which include some component of retinal/choroidal neovascularization include, but are not limited to, Best's diseases, myopia, optic pits, Stargart's diseases, Paget's disease, vein occlusion, artery occlusion, sickle cell anemia, sarcoid, syphilis, pseudoxanthoma elasticum carotid apo structive diseases, chronic uveitis/vitritis, mycobacterial infections, Lyme's disease, systemic lupus erythematosus, retinopathy of prematurity, Eale's disease, diabetic retinopathy, macular degeneration, Bechet's diseases, infections causing a retinitis or chroiditis, presumed ocular histoplasmosis, pars planitis, chronic retinal detachment, hyperviscosity syndromes, toxoplasmosis, trauma and post-laser complications, diseases associated with rubesis (neovascularization of the angle) and diseases caused by the abnormal proliferation of fibrovascular or fibrous tissue including all forms of proliferative vitreoretinopathy. Examples of corneal neovascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, diabetic retinopathy, retinopathy of prematurity, corneal graft rejection, Mooren ulcer, Terrien's marginal degeneration, marginal keratolysis, polyarteritis, Wegener sarcoidosis, Scleritis, periphigoid radial keratotomy, neovascular glaucoma and retrolental fibroplasia, syphilis, Mycobacteria infections, lipid degeneration, chemical burns, bacterial ulcers, fungal ulcers, Herpes simplex infections, Herpes zoster infections, protozoan infections and Kaposi sarcoma.

Chronic inflammatory diseases associated with uncontrolled angiogenesis may also be treated using HDAC inhibitors of the present invention. Chronic inflammation depends on continuous formation of capillary sprouts to maintain an influx of inflammatory cells. The influx and presence of the inflammatory cells produce granulomas and thus maintains the chronic inflammatory state. Inhibition of angiogenesis using a HDAC inhibitor alone or in conjunction with other anti-inflammatory agents may prevent the formation of the granulomas and thus alleviate the disease. Examples of chronic inflammatory diseases include, but are not limited to, inflammatory bowel diseases such as Crohn's disease and ulcerative colitis, psoriasis, sarcoidosis, and rheumatoid arthritis.

Inflammatory bowel diseases such as Crohn's disease and ulcerative colitis are characterized by chronic inflammation and angiogenesis at various sites in the gastrointestinal tract. For example, Crohn's disease occurs as a chronic transmural inflammatory disease that most commonly affects the distal ileum and colon but may also occur in any part of the gastrointestinal tract from the mouth to the anus and perianal area. Patients with Crohn's disease generally have chronic diarrhoea associated with abdominal pain, fever, anorexia, weight loss and abdominal swelling. Ulcerative colitis is also a chronic, nonspecific, inflammatory and ulcerative disease arising in the colonic mucosa and is characterized by the presence of bloody diarrhoea. These inflammatory bowel diseases are generally caused by chronic granulomatous inflammation throughout the gastrointestinal tract, involving new capillary sprouts surrounded by a cylinder of inflammatory cells. Inhibition of angiogenesis by these inhibitors should inhibit the formation of the sprouts and prevent the formation of granulomas. Inflammatory bowel diseases also exhibit extra intestinal manifestations, such as skin lesions. Such lesions are characterized by inflammation and angiogenesis and can occur at many sites other the gastrointestinal tract. Inhibition of angiogenesis by HDAC inhibitors according to the present invention can reduce the influx of inflammatory cells and prevent lesion formation.

Sarcoidosis, another chronic inflammatory disease, is characterized as a multisystem granulomatous disorder. The granulomas of this disease can form anywhere in the body. Thus, the symptoms depend on the site of the granulomas and whether the disease is active. The granulomas are created by the angiogenic capillary sprouts providing a constant supply of inflammatory cells. By using HDAC inhibitors according to the present invention to inhibit angiogenesis, such granulomas formation can be inhibited. Psoriasis, also a chronic and recurrent inflammatory disease, is characterized by papules and plaques of various sizes. Treatment using these inhibitors alone or in conjunction with other anti-inflammatory agents should prevent the formation of new blood vessels necessary to maintain the characteristic lesions and provide the patient relief from the symptoms.

Rheumatoid arthritis (RA) is also a chronic inflammatory disease characterized by non-specific inflammation of the peripheral joints. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Treatment using HDAC inhibitors according to the present invention alone or in conjunction with other anti-RA agents may prevent the formation of new blood vessels necessary to maintain the chronic inflammation.

The compounds of the present invention can further be used in the treatment of cardiac/vasculature diseases such as hypertrophy, hypertension, myocardial infarction, reperfusion, ischaemic heart disease, angina, arrhythmias, hypercholesterolemia, atherosclerosis and stroke. The compounds can further be used to treat neurodegenerative disorders/CNS disorders such as acute and chronic neurological diseases, including stroke, Huntington's disease, Amyotrophic Lateral Sclerosis and Alzheimer's disease.

The compounds of the present invention can also be used as antimicrobial agents, for example antibacterial agents. The invention therefore also provides a compound for use in the treatment of a bacterial infection. The compounds of the present invention can be used as anti-infectious compounds against viral, bacterial, fungal and parasitic infections. Examples of infections include protozoal parasitic infections (including *plasmodium, cryptosporidium parvum, toxoplasma gondii, sarcocystis neurona* and *Eimeria* sp.)

The compounds of the present invention are particularly suitable for the treatment of undesirable or uncontrolled cell proliferation, preferably for the treatment of benign tumours/hyperplasias and malignant tumours, more preferably for the treatment of malignant tumours and most preferably for the treatment of chronic lymphocytic leukaemia (CLL), breast cancer, prostate cancer, ovarian cancer, mesothelioma, T-cell lymphoma.

In a preferred embodiment of the invention, the compounds of the invention are used to alleviate cancer, cardiac hypertrophy, chronic heart failure, an inflammatory condition, a cardiovascular disease, a haemoglobinopathy, a thalassemia, a sickle cell disease, a CNS disorder, an autoimmune disease, organ transplant rejection, diabetes, osteoporosis, MDS, benign prostatic hyperplasia, oral leukoplakia, a genetically related metabolic disorder, an infection, Rubens-Taybi, fragile X syndrome, or alpha-1 antitrypsin deficiency, or to accelerate wound healing, to protect hair follicles or as an immunosuppressant.

Typically, said inflammatory condition is a skin inflammatory condition (for example psoriasis, acne and eczema), asthma, chronic obstructive pulmonary disease (COPD), rheumatoid arthritis (RA), inflammatory bowel disease (IBD), Crohn's disease or colitis.

Typically, said cancer is chronic lymphocytic leukaemia, breast cancer, prostate cancer, ovarian cancer, mesothelioma or T-cell lymphoma.

Typically, said cardiovascular disease is hypertension, myocardial infarction (MI), ischemic heart disease (IHD) (reperfusion), angina pectoris, arrhythmia, hypercholesterolemia, hyperlipidaemia, atherosclerosis, stroke, myocarditis, congestive heart failure, primary and secondary i.e. dilated (congestive) cardiomyopathy, hypertrophic cardiomyopathy, restrictive cardiomyopathy, peripheral vascular disease, tachycardia, high blood pressure or thrombosis.

Typically, said genetically related metabolic disorder is cystic fibrosis (CF), peroxisome biogenesis disorder or adrenoleukodystrophy.

Typically, the compounds of the invention are used as an immunosuppressant following organ transplant.

Typically, said infection is a viral, bacterial, fungal or parasitic infection, in particular an infection by *S aureus, P acne, candida* or *aspergillus*.

Typically, said CNS disorder is Huntingdon's disease, Alzheimer's disease, multiple sclerosis or amyotrophic lateral sclerosis.

In this embodiment, the compounds of the invention may be used to alleviate cancer, cardiac hypertrophy, chronic heart failure, an inflammatory condition, a cardiovascular disease, a haemoglobinopathy, a thalassemia, a sickle cell disease, a CNS disorder, an autoimmune disease, diabetes or osteoporosis, or are used as an immunosuppressant.

The compounds of the invention may also be used to alleviate chronic lymphocytic leukaemia (CLL), breast cancer, prostate cancer, ovarian cancer, mesothelioma, T-cell lymphoma, cardiac hypertrophy, chronic heart failure or a skin inflammatory condition, in particular psoriasis, acne or eczema.

The compounds of the present invention can be used in the treatment of animals, preferably in the treatment of mammals and more preferably in the treatment of humans.

The compounds of the invention may, where appropriate, be used prophylactically to reduce the incidence of such conditions.

In use, a therapeutically effective amount of a compound of the invention is administered to a patient. A typical dose is from about 0.001 to 50 mg per kg of body weight, according to the activity of the specific compound, the age, weight and conditions of the subject to be treated, the type and severity of the disease and the frequency and route of administration.

Compounds of the invention may be tested for HDAC inhibitory activity by any suitable assay, e.g. the assay described in WO2008/062201.

The following Examples illustrate the invention.

General Methods i. General Procedure for Synthesis of Secondary Amines

Method A (Using BINAP):

4,6-Dimethylpyridin-2-amine (200 mg, 1.63 mmol), 2-bromo-5-fluoropyridine (317 mg, 1.8 mmol), potassium tert-butoxide (236 mg, 2.45 mmol) and (±)-BINAP (40 mg, 0.06 mmol) were stirred in toluene (4 mL) and degassed using Ar(g) for 30 min. Pd$_2$(dba)$_3$ (45 mg, 0.049 mmol) was then added and the reaction mixture stirred for 12 h at 90° C. under Ar(g). The reaction was monitored by TLC. Following complete consumption of starting material, the reaction mixture was diluted with CH$_2$Cl$_2$ (20 mL) and silica was added. The solvent was removed in vacuo and the resulting dry loaded material was purified by silica gel column chromatography with hexane/EtOAc (4:1-1:1), to provide N-(5-fluoropyridin-2-yl)-4,6-dimethylpyridin-2-amine.

Method B (Using SPhos):

2-Bromopyridine (200 mg, 1.26 mmol), 5-methylpyridin-2-amine (150 mg, 1.38 mmol), potassium tert-butoxide (182 mg, 1.89 mmol) and 2-dicyclohexylphosphino-2',6'-dimethoxybiphenyl (SPhos) (20 mg, 0.05 mmol) were stirred in toluene (4 mL) and the reaction mixture was degassed using Ar(g) for 30 min. Pd$_2$(dba)$_3$ (34 mg, 0.037 mmol) was then added, and the reaction mixture was stirred for 12 h at 90° C. under Ar(g). The reaction was monitored by TLC. Following complete consumption of the starting material, the reaction mixture was diluted with CH$_2$Cl$_2$ (20 mL) and silica was added. The solvent was removed in vacuo, and the resulting dry loaded material was purified by silica gel column chromatography with hexane/EtOAc, (4:1-1:1), to provide N-(pyridin-2-yl)-5-methylpyridin-2-amine.

a) 3-Methoxy-N-(5-methylpyridin-2-yl)pyridin-2-amine

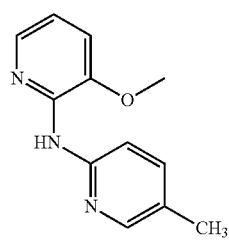

Synthesised according to the general procedure Method B (Using SPhos).

$^1$H NMR (400 MHz, Chloroform-d), δ$_H$ ppm: 8.44 (d, J=8.6 Hz, 1H), 8.02-8.13 (m, 1H), 7.73-7.93 (m, 2H), 7.48 (dd, J=8.6, 2.3 Hz, 1H), 6.99 (dd, J=7.8, 1.5 Hz, 1H), 6.83-6.71 (m, 1H), 3.89 (s, 3H), 2.27 (s, 3H).

b) 5-Methoxy-N-(5-methylpyridin-2-yl)pyridin-2-amine

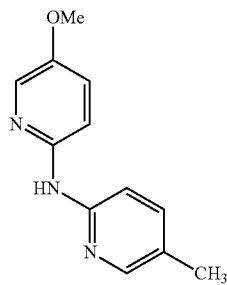 [SMILES: COc1ccc(Nc2ccc(C)cn2)nc1]

Synthesised according to the general procedure Method B (Using SPhos).

$^1$H NMR (400 MHz, Chloroform-d), δ$_H$ ppm: 8.04 (d, J=2.5 Hz, 1H), 7.95 (d, J=3.0 Hz, 1H), 7.50 (d, J=9.0 Hz, 1H), 7.40 (dd, J=8.4, 2.6 Hz, 1H), 7.31 (d, J=8.4 Hz, 1H), 7.22 (dd, J=9.0, 3.1 Hz, 1H), 3.87 (m, 3H), 2.25 (s, 3H).

c) 3-Methoxy-N-(5-morpholinopyridin-2-yl)pyridin-2-amine

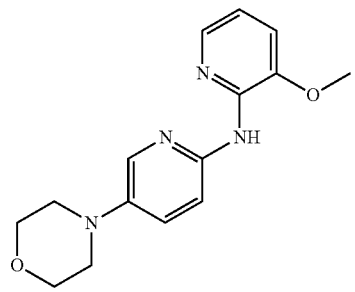 [SMILES: COc1cccnc1Nc1ccc(N2CCOCC2)cn1]

Synthesised according to the general procedure Method B (Using SPhos).

$^1$H NMR (400 MHz, Chloroform-d), δ$_H$ ppm: 8.45 (d, J=9.1 Hz, 1H), 7.94 (d, J=3.0 Hz, 1H), 7.83 (dd, J=5.1, 1.5 Hz, 1H), 7.31 (dd, J=9.1, 3.1 Hz, 1H), 6.98 (dd, J=7.9, 1.5 Hz, 1H), 6.73 (dd, J=7.8, 5.1 Hz, 1H), 3.76-3.98 (m, 7H), 3.06-3.16 (m, 4H).

d) 5-Methoxy-N-(5-morpholinopyridin-2-yl)pyridin-2-amine

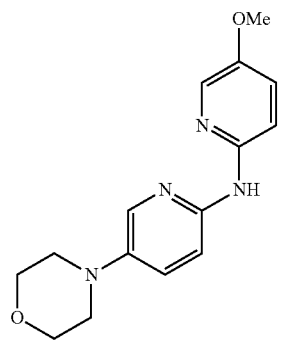 [SMILES: COc1ccc(Nc2ccc(N3CCOCC3)cn2)nc1]

Synthesised according to the general procedure Method B (Using SPhos).

¹H NMR (400 MHz, Chloroform-d), δ$_H$ ppm: 7.90 (dd, J=15.8, 3.0 Hz, 2H), 7.43 (d, J=9.0 Hz, 2H), 7.19-7.30 (m, 2H), 3.87 (t, J=4.8 Hz, 4H), 3.82 (s, 3H), 3.00-3.16 (m, 4H).

e) N-(Pyridin-2-yl)thieno[3,2-c]pyridin-4-amine

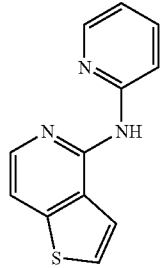 [SMILES: c1ccc(Nc2nccc3sccc23)nc1]

Synthesised according to the general procedure Method B (Using SPhos).

¹H NMR (400 MHz, Chloroform-d), δ$_H$ ppm: 8.58 (d, J=8.4 Hz, 1H), 8.26 (dd, J=5.1, 2.0 Hz, 1H), 8.12 (d, J=5.7 Hz, 1H), 7.72 (ddd, J=8.8, 7.1, 1.9 Hz, 1H), 7.51 (d, J=5.9 Hz, 1H), 7.46 (d, J=5.4 Hz, 1H), 7.38 (d, J=5.7 Hz, 1H), 6.93 (ddd, J=7.1, 4.8, 1.0 Hz, 1H).

f) 6-Methyl-N-(5-morpholinopyridin-2-yl)pyridin-2-amine

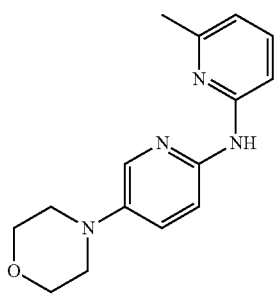 [SMILES: Cc1cccc(Nc2ccc(N3CCOCC3)cn2)n1]

Synthesised according to the general procedure Method B (Using SPhos).

¹H NMR (400 MHz, Chloroform-d), δ$_H$ ppm: 7.94 (d, J=3.0 Hz, 1H), 7.40-7.59 (m, 2H), 7.24 (d, J=8.1 Hz, 2H), 6.66 (d, J=7.3 Hz, 1H), 3.80-3.96 (m, 4H), 3.01-3.17 (m, 4H), 2.45 (s, 3H).

g) N-(6-(Trifluoromethyl)pyridin-2-yl)thieno[3,2-c]pyridin-4-amine

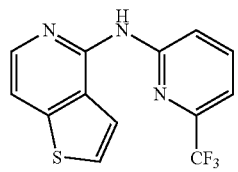 [SMILES: FC(F)(F)c1cccc(Nc2nccc3sccc23)n1]

Synthesised according to the general procedure Method A (Using BINAP).

¹H NMR (400 MHz, Chloroform-d), δ$_H$ ppm: 8.82 (d, J=8.5 Hz, 1H), 8.14 (d, J=5.7 Hz, 1H), 7.83 (dd, J=18.3, 10.3 Hz, 2H), 7.51 (s, 1H), 7.44 (d, J=5.7 Hz, 1H), 7.29 (d, J=7.4 Hz, 1H).

h) N5-(2-Methoxyethyl)-N5-methyl-N2-(4-(trifluoromethyl)pyridin-2-yl)pyridine-2,5-diamine

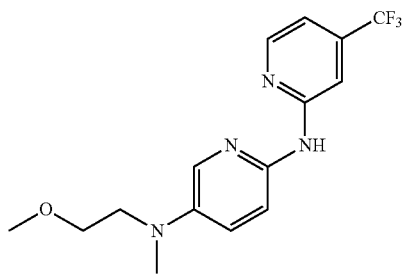 [SMILES: COCCN(C)c1ccc(Nc2cc(C(F)(F)F)ccn2)nc1]

Synthesised according to the general procedure Method A (Using BINAP).

¹H NMR (400 MHz, Chloroform-d), δ$_H$ ppm: 8.32 (d, J=5.2 Hz, 1H), 7.87 (d, J=3.1 Hz, 1H), 7.70-7.78 (m, 1H), 7.29-7.37 (m, 1H), 7.15 (dd, J=9.0, 3.1 Hz, 1H), 6.88-6.98 (m, 1H), 3.54-3.59 (m, 2H), 3.48 (t, J=5.5 Hz, 2H), 3.37 (s, 3H), 2.98 (s, 3H).

i) N5-(2-Methoxyethyl)-N2-(3-methoxypyridin-2-yl)-N5-methylpyridine-2,5-diamine

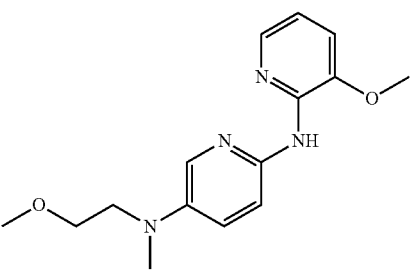

Synthesised according to the general procedure Method B (Using SPhos).

¹H NMR (400 MHz, Chloroform-d), δ$_H$ ppm: 8.37 (d, J=9.1 Hz, 1H), 7.81 (q, J=1.7 Hz, 2H), 7.19 (dd, J=9.1, 3.1 Hz, 1H), 6.96 (dd, J=7.7, 1.5 Hz, 1H), 6.70 (dd, J=7.8, 5.1 Hz, 1H), 3.88 (s, 3H), 3.56 (t, J=5.8 Hz, 2H), 3.45 (t, J=5.8 Hz, 2H), 3.36 (s, 3H), 2.96 (s, 3H).

j) N5-(2-methoxyethyl)-N2-(5-methoxypyridin-2-yl)-N5-methylpyridine-2,5-diamine

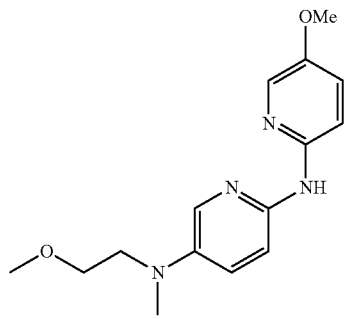 [SMILES: COCCN(C)c1ccc(Nc2ccc(OC)cn2)nc1]

Synthesised according to the general procedure Method B (Using SPhos).

$^1$H NMR (400 MHz, Chloroform-d), $\delta_H$ ppm: 7.89 (d, J=3.0 Hz, 1H), 7.74 (d, J=3.1 Hz, 1H), 7.45 (d, J=9.1 Hz, 1H), 7.37 (d, J=9.0 Hz, 1H), 7.19 (ddd, J=12.0, 9.0, 3.1 Hz, 2H), 3.82 (s, 3H), 3.55 (t, J=5.8 Hz, 2H), 3.43 (t, J=5.8 Hz, 2H), 3.36 (s, 3H), 2.94 (s, 3H).

iii. General Procedure for Alkylation and Hydroxamic Acid Formation

NaH (12 mg, 0.5 mmol, 2 eq) was added portion-wise to secondary amine (50 mg, 0.25 mmol, 1 eq) in DMF (2 mL) at 0° C. under Ar(g). Following addition, the reaction mixture was stirred for 20 min, then methyl-4-(bromomethyl)benzoate (57 mg, 0.25 mmol, 1 eq) was added. The reaction mixture was stirred at rt under Ar(g) for 2 h, and the reaction was monitored by TLC. Following complete consumption of the starting material, the reaction mixture was poured onto brine (25 mL), extracted with EtOAc (3×25 mL). The organic phases were combined, dried over Na$_2$SO$_4$, filtered and subsequently concentrated in vacuo. The resulting crude product was purified by silica gel column chromatography with hexane/EtOAc (19:1-3:1), to provide the desired methyl ester as a gummy, yellowish solid.

To a stirred solution of the methyl ester (70 mg, 0.20 mmol) in MeOH/CH$_2$Cl$_2$ (3:1, 4 mL) under an inert atmosphere was added 50% aq. hydroxylamine sol (2.5 mL) at 0° C., and the resulting reaction mixture was stirred for 20 min. Sodium hydroxide solution (54 mg in 1 mL water, 1.35 mmol) was then added to the reaction mixture; this was following by stirring for 30 min, and the mixture was then warmed to rt and stirred for 2 h. The reaction was monitored by TLC. Following complete consumption of the starting material, the volatiles were concentrated in vacuo. The residue was acidified with acetic acid to pH-6. The compound was extracted with CH$_2$Cl$_2$/MeOH (9:1) (3×20 mL); the combined organic extracts were concentrated in vacuo to obtain the crude product, which was purified by silica gel column chromatography (1-10% MeOH/CH$_2$Cl$_2$) to afford the desired product as gummy, yellowish solid.

SPECIFIC EXAMPLES

Example A

4-{[Bis(pyridin-2-yl)amino]methyl}-N-hydroxybenzamide

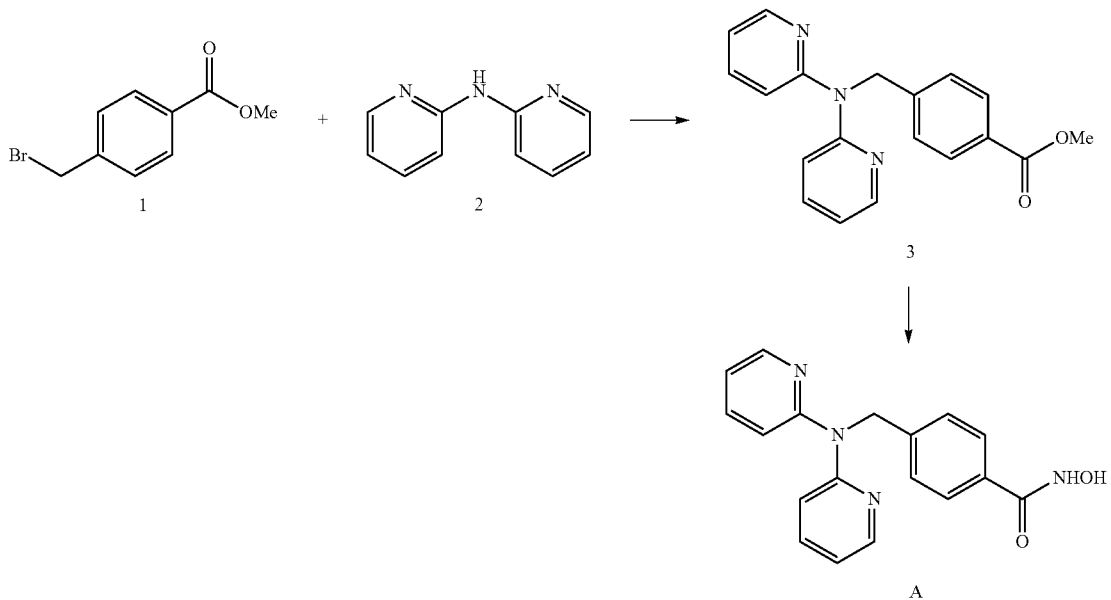

NaH (83 mg, 2.18 mmol) was added to 2,2'-bipyridylamine, 2 (373 mg, 2.18 mmol) in DMF (5 mL) at rt. After 15 min, methyl-4-(bromomethyl)benzoate (1) (500 mg, 2.18 mmol) was added, and the reaction mixture was subsequently stirred at 90° C. for 1 h under Ar(g). Once cooled to rt, the reaction mixture was poured onto brine (50 mL) and extracted twice with EtOAc (2×25 mL). The organic phases were combined, dried over MgSO$_4$, filtered, and subsequently concentrated in vacuo. The resulting residue was purified by silica gel column chromatography with hexanes/EtOAc (4:1) to furnish 3 as a white solid (429 mg, 62%).

LCMS (ES): found 319.9 [M+H]$^+$.

A freshly prepared solution of NH$_2$OH in MeOH (0.4M, 20 mL) was added to 4-{[bis(pyridin-2-yl)amino]methyl}benzoate (3) (100 mg, 0.3 mmol) at 0° C. followed by KOH solubilized in MeOH (0.8M, 4 mL). The reaction mixture was then stirred at rt for 18 h, was subsequently concentrated in vacuo (ca 5 mL) and poured onto water (50 mL). The basic aqueous phase was extracted initially with EtOAc (25 mL) and the phases were separated. The aqueous was then neutralized with 2N HCl and extracted again with EtOAc (25 mL). The resulting organic phase was dried over $MgSO_4$, filtered and subsequently concentrated in vacuo to provide Example A as a white solid (51 mg, 51%).

$^1$H NMR (400 MHz, Methanol-$d_4$), $\delta_H$ ppm: 6.69-6.76 (m, 2H), 6.07-6.15 (m, 4H), 5.91 (d, J=8.6 Hz, 2H), 5.65 (d, J=8.1 Hz, 2H), 5.44 (dd, J=6.6, 5.1 Hz, 2H), 3.97 (s, 2H).

LCMS (ES): found 321.1 [M+H]$^+$.

Example B

4-{[Bis(3-methyl-1,2,4-thiadiazol-5-yl)amino]methyl}-2-fluoro-N-hydroxybenzamide residue was slurried with MeCN (2×100 mL) and filtered. The filtrate was concentrated to afford (3) as an oil/NMP solution (700 mg).

LCMS (ES): found 214.0 [M+H]$^+$.

Potassium carbonate (360 mg) and methyl 4-(bromomethyl)-2-fluorobenzoate (4) (160 mg, 0.65 mmol) were added to a solution of 3-methyl-N-(3-methyl-1,2,4-thiadiazol-5-yl)-1,2,4-thiadiazol-5-amine (3) (<1 mmol) in MeCN (10 mL) and the reaction mixture was heated, under $N_2(g)$, with stirring, at 50° C. After 2 h, the reaction mixture was cooled, diluted with EtOAc and extracted sequentially with water, saturated bicarbonate solution and saturated brine solution, and was then dried over $Na_2SO_4$, filtered and concentrated. Purification on silica with $CH_2Cl_2$/MeOH (1:0-97:3) yielded (5) as a solid (180 mg, 73%).

LCMS (ES): found 380.0 [M+H]$^+$.

50% Hydroxylamine aqueous solution (2 mL) was added to a solution of methyl 4-{[bis(3-methyl-1,2,4-thiadiazol-5-yl)amino]methyl}-2-fluorobenzoate (5) (180 mg, 0.47

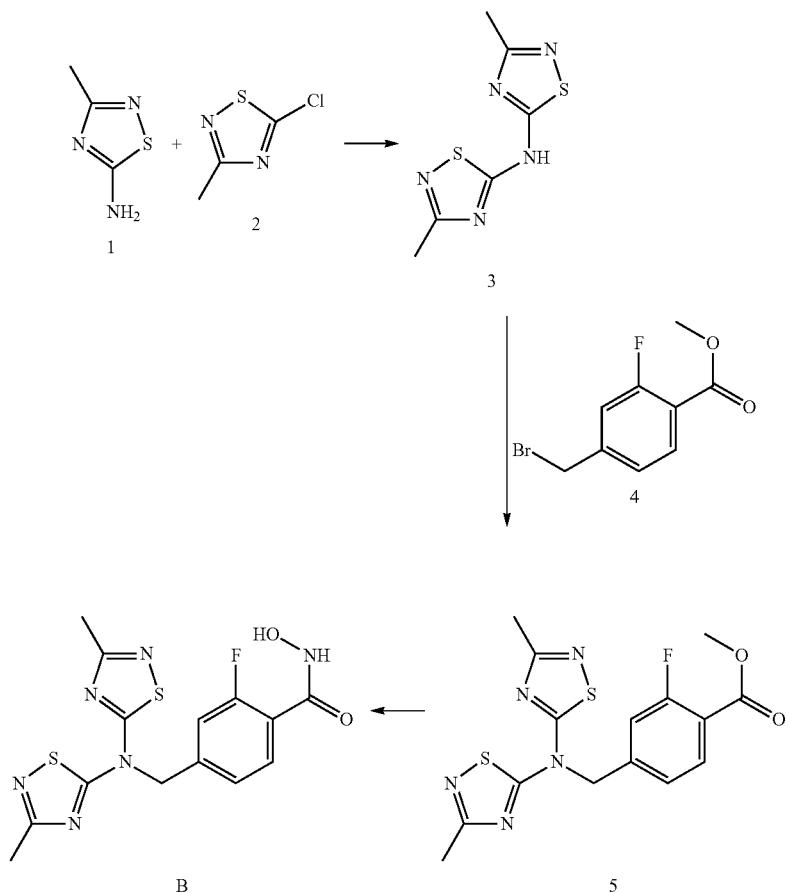

NaH (60% in oil) (50 mg) was added to a solution of 3-methyl-1,2,4-thiadiazol-5-amine (1) (115 mg, 1 mmol) in NMP (2 mL). After 10 min, 5-chloro-3-methyl-1,2,4-thiadiazole (2) (140 mg, 1.05 mmol) was added and the resultant mixture stirred at 45° C. under $N_2(g)$. After 4 h, the reaction mixture was diluted with EtOAc and extracted with saturated bicarbonate solution (×3). Analysis indicated that all desired product was in the aqueous phase. The combined aqueous phases were concentrated to dryness; the resultant mmol) in MeOH (8 mL). The solution was stirred at 45° C. for 7 days, sealed in a vial. The resulting reaction mixture became heterogeneous; on cooling, a white solid was collected by filtration, washed with cold methanol and dried in vacuo to afford the title product, Example B, as solid (50 mg, 28%).

$^1$H NMR (400 MHz, DMSO-$d_6$), $\delta_H$ ppm: 10.90 (br. s., 1H), 9.17 (br. s., 1H), 7.51 (t, J=7.6 Hz, 1H), 7.27 (d, J=10.8 Hz, 1H), 7.16 (dd, J=7.9, 1.3 Hz, 1H), 5.57 (s, 2H), 2.50 (s, 6H).

LCMS (ES): found 381.0 [M+H]$^+$.

Example C

2-Fluoro-N-hydroxy-4-{[(3-methyl-1,2,4-oxadiazol-5-yl)(3-methyl-1,2,4-thiadiazol-5-yl)amino]methyl}benzamide

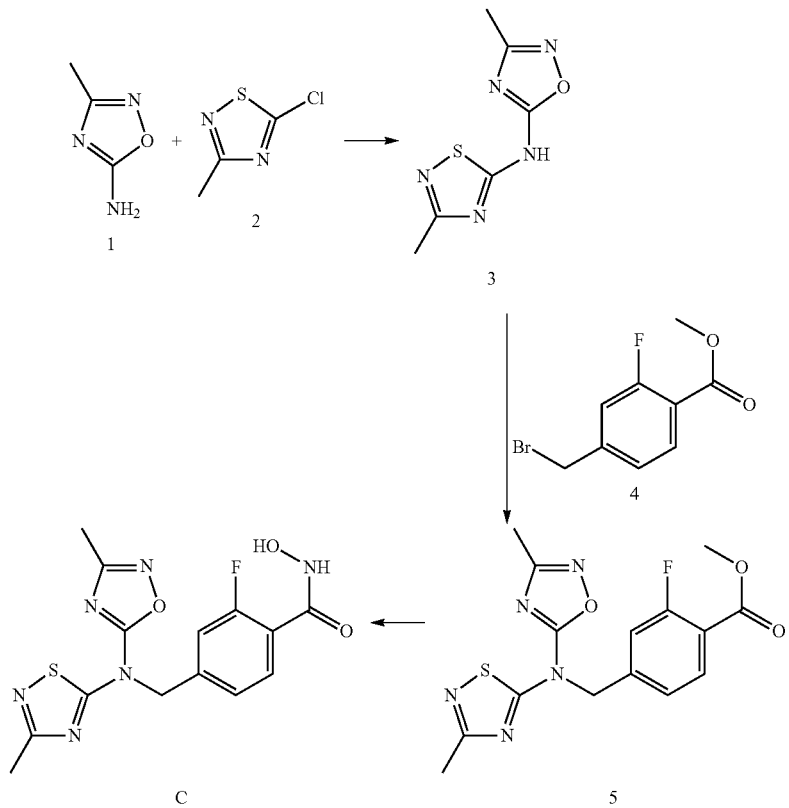

NaH (60% in oil) (50 mg) was added to a solution of 3-methyl-1,2,4-oxadiazol-5-amine (1) (100 mg, 1 mmol) in NMP (2 mL). After 10 min, 5-chloro-3-methyl-1,2,4-thiadiazole (2) (150 mg, 1.1 mmol) was added, and the resultant mixture was stirred at 45° C. under N$_2$(g). After 18 h, analysis by LCMS was conducted.

LCMS (ES): found 198.0 [M+H]$^+$.

NaH (60% in oil) (70 mg) and methyl 4-(bromomethyl)-2-fluorobenzoate (4) (200 mg, 0.81 mmol) were added to the above reaction mixture and heating was continued at 45° C. under N$_2$(g). After 3 h, a further quantity of (4) (90 mg, 0.36 mmol) was added. After an additional 2 h, the reaction mixture was cooled, diluted with EtOAc, and extracted sequentially with water saturated bicarbonate solution (×2), and was then dried over Na$_2$SO$_4$, filtered and concentrated. Purification by silica gel chromatography with CH$_2$Cl$_2$/MeOH (1:0-97:3) yielded a residue (5) (350 mg, 96% over 2 steps).

LCMS (ES): found 364.0 [M+H]$^+$.

50% Hydroxylamine aqueous solution (1 mL) was added to a crude solution of methyl 4-{[bis(3-methyl-1,2,4-thiadiazol-5-yl)amino]methyl}-2-fluorobenzoate (5) (350 mg, 0.96 mmol) in methanol (5 mL). The resulting solution was stirred at 45-50° C. for 5 days, sealed in a vial. The reaction mixture turned heterogeneous and, on cooling, a white solid was filtered off and the resulting filtrate was concentrated. The filtrate was purified by RP-HPLC on Xterra 10-70% MeCN/water+0.1% formic acid, to furnish the title compound, Example C (30 mg, 8%).

$^1$H NMR (400 MHz, Methanol-d$_4$), δ$_H$ ppm: 7.69 (t, J=7.6 Hz, 1H), 7.12-7.22 (m, 2H), 5.48 (s, 2H), 2.44 (s, 3H), 2.32 (s, 3H).

LCMS (ES): found 365.0 [M+H]$^+$.

Example D

N-Hydroxy-4-(((3-methyl-1,2,4-oxadiazol-5-yl)(pyridin-2-yl)amino)methyl)benzamide

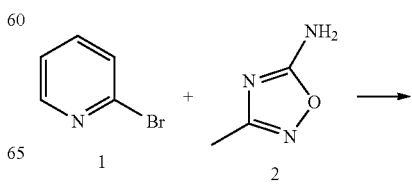

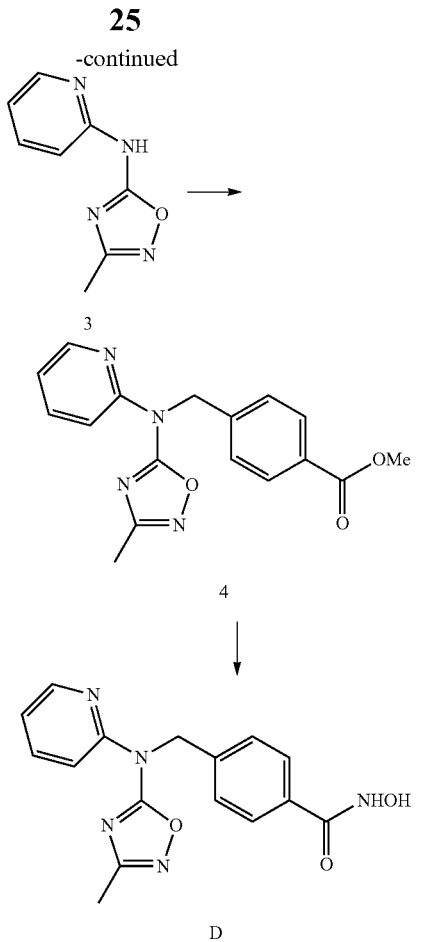

2-Bromopyridine (1) (1.0 g, 6.32 mmol), 3-methyl-1,2,4-oxadiazol-5-amine (2) (0.940 g, 9.49 mmol), Xantphos (0.366 g, 0.63 mmol), and $Cs_2CO_3$ (4.1 g, 12.64 mmol) were combined in dry 1,4-dioxane (15 mL). The reaction mixture was degassed with $N_2(g)$ and placed under vacuum for 10 min. $Pd_2(dba)_3$ (0.28 g, 0.31 mmol) was then added to the reaction mixture, which was heated at 90° C. for 30 h. It was then poured into demineralized water (200 mL) and extracted with EtOAc (3×100 mL). The organic phases were combined, dried over $Na_2SO_4$, filtered and subsequently concentrated in vacuo. The resulting residue was purified by flash chromatography with EtOAc/Hexane (1:1) to provide 3-methyl-N-(pyridin-2-yl)-1,2,4-oxadiazol-5-amine (3) as a white solid (0.7 g, 63%).

LCMS (ES): Found 177.1 $[M+H]^+$.

NaH (60%) (52.5 mg, 1.31 mmol) was added portionwise to 3-methyl-N-(pyridin-2-yl)-1,2,4-oxadiazol-5-amine (3) (220 mg, 1.25 mmol) in DMF (5 mL) at 5° C. under Ar(g). The reaction mixture was stirred for 20 min, then methyl 4-(bromomethyl)benzoate (372 mg, 1.62 mmol) was added, and stirring was continued at 80° C. under Ar(g) for 1 h. The reaction mixture was then poured onto demineralized water (100 mL), and extracted with EtOAc (3×50 mL). The organic phases were combined, dried over $Na_2SO_4$, filtered and subsequently concentrated in vacuo. The resulting residue was purified by flash chromatography with EtOAc/Hexane (1:1) to furnish methyl 4-(((3-methyl-1,2,4-oxadiazol-5-yl)(pyridin-2-yl)amino)methyl)benzoate (4) as a white solid (130 mg, 40%).

LCMS (ES): Found 325.1 $[M+H]^+$.

A fresh solution of $NH_2OH$ in MeOH was prepared: [KOH (0.91 g, 16.3 mmol) in MeOH (10 mL) was added to $NH_2OH·HCl$ (1.12 g, 16.3 mmol) in MeOH (10 mL) at 0° C.]. The reaction mixture was stirred for 20 min at 0° C., then filtered to remove salts; it was then added to methyl 4-(((3-methyl-1,2,4-oxadiazol-5-yl)(pyridin-2-yl)amino)methyl)benzoate (4) (105.5 mg, 0.3 mmol) followed by KOH (181 mg, 3.2 mmol) solubilized in MeOH (5 mL). The reaction mixture was stirred at rt for 21 h, and then concentrated in vacuo, poured onto brine/$H_2O$ (15 mL/35 mL), and extracted with $CH_2Cl_2$ (3×50 mL). The organic phases were combined, dried over $Na_2SO_4$, filtered and subsequently concentrated in vacuo. The resulting residue was purified by flash chromatography with MeOH/$CH_2Cl_2$ (10:90) to provide N-hydroxy-8-((3-methyl-1,2,4-oxadiazol-5-yl)(pyridin-2-yl)amino)octanamide, Example D, as a light yellow solid (12.2 mg, 40%).

$^1$H NMR (400 MHz, DMSO-$d_6$), $\delta_H$ ppm: 11.14 (br. s., 1H), 9.01 (br. s., 1H), 8.42 (dd, J=4.8, 1.1 Hz, 1H), 8.07 (d, J=8.4 Hz, 1H), 7.92 (ddd, J=8.5, 7.4, 2.0 Hz, 1H), 7.66 (d, J=8.3 Hz, 2H), 7.34 (d, J=8.3 Hz, 2H), 7.23 (ddd, J=7.3, 4.9, 0.8 Hz, 1H), 5.48 (s, 2H), 2.23 (s, 3H).

LCMS (ES): Found 326.1 $[M+H]^+$.

Example E

N-Hydroxy-4-(((1-methyl-1H-pyrazol-3-yl)(pyridin-2-yl)amino)methyl)benzamide

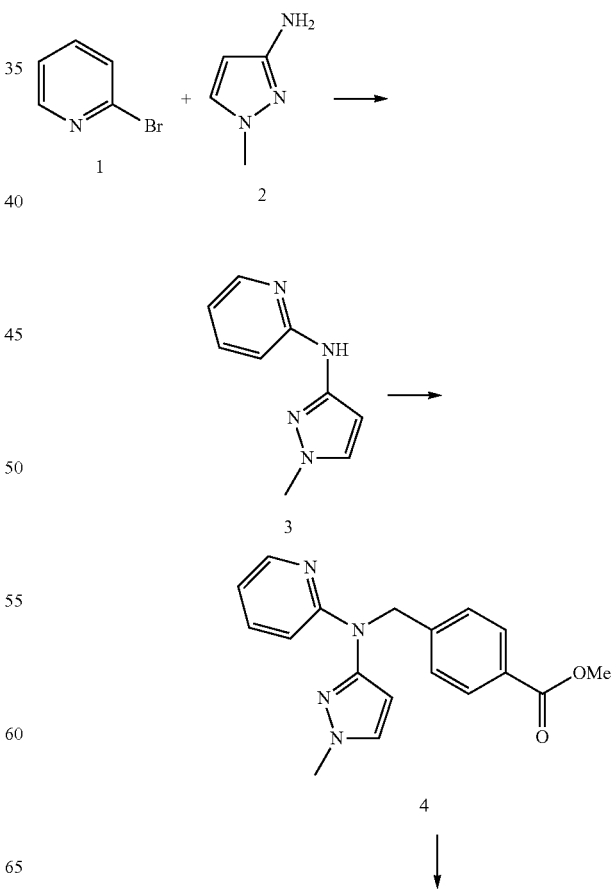

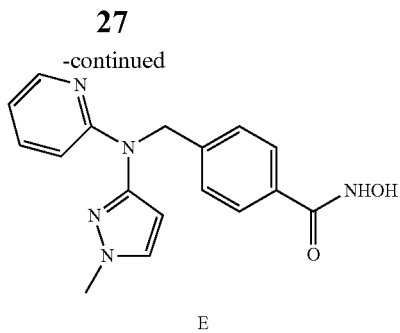

E

2-Bromopyridine (1) (1.0 g, 6.3 mmol), 1-methyl-1H-pyrazol-3-amine (2) (0.79 g, 8.2 mmol), Xantphos (0.37 g, 0.63 mmol), and Cs$_2$CO$_3$ (4.1 g, 12.6 mmol) were combined in dry 1,4-dioxane (15 mL). The reaction mixture was then degassed with N$_2$(g), and placed under vacuum for 10 min. Pd$_2$(dba)$_3$ (0.29 g, 0.31 mmol) was added and the resulting reaction mixture was heated at 90° C. for 30 h. It was then poured onto demineralized water (200 mL), and extracted with EtOAc (3×100 mL). The organic phases were combined, dried over Na$_2$SO$_4$, filtered and subsequently concentrated in vacuo. The resulting residue was purified by flash chromatography with EtOAc/Hexane (1:1) to provide N-(1-methyl-1H-pyrazol-3-yl)pyridin-2-amine (3) as a yellow solid (0.75 g, 68%).

LCMS (ES): Found 175.2 [M+H]$^+$.

NaH (60%) (60.4 mg, 1.5 mmol) was added portion-wise to N-(1-methyl-1H-pyrazol-3-yl)pyridin-2-amine (3) (250 mg, 1.4 mmol) in DMF (8 mL) at 5° C. under Ar(g). The reaction mixture was stirred for 20 min, then methyl 4-(bromomethyl)benzoate (428 mg, 1.8 mmol) was added, and stirring was continued at 70° C. under Ar(g) for 1 h. The reaction mixture was then poured onto demineralized water (100 mL), and extracted with EtOAc (3×50 mL). The organic phases were combined, dried over Na$_2$SO$_4$, filtered and subsequently concentrated in vacuo. The resulting residue was purified by flash chromatography with EtOAc/Hexane (3:7) to furnish methyl 4-(((1-methyl-1H-pyrazol-3-yl)(pyridin-2-yl)amino)methyl)benzoate (4) as a light yellow solid (440 mg, 82%).

LCMS (ES): Found 323.1 [M+H]$^+$.

A fresh solution of NH$_2$OH in MeOH was prepared: [KOH (3.83 g, 68.3 mmol) in MeOH (20 mL) was added to NH$_2$OH.HCl (4.74 g, 68.3 mmol) in MeOH (20 mL) at 0° C.]. The reaction mixture was stirred for 20 min at 0° C., then filtered to remove salts; it was then added to 4-(((1-methyl-1H-pyrazol-3-yl)(pyridin-2-yl)amino)methyl)benzoate (4) (440 mg, 1.3 mmol) followed by KOH (766 mg, 13.0 mmol) solubilized in MeOH (10 mL). The reaction mixture was stirred at rt for 21 h, and then concentrated in vacuo, poured onto brine/H$_2$O (30 mL/70 mL), and extracted with CH$_2$Cl$_2$ (3×100 mL). The organic phases were combined, dried over Na$_2$SO$_4$, filtered and subsequently concentrated in vacuo. The resulting residue was purified by flash chromatography with MeOH/CH$_2$Cl$_2$ (1:9) to provide N-hydroxy-4-(((1-methyl-1H-pyrazol-3-yl)(pyridin-2-yl)amino)methyl)benzamide, Example E, as a light brown liquid (50 mg, 11%).

$^1$H NMR (400 MHz, Methanol-d$_4$), δ$_H$ ppm: 8.09 (ddd, J=5.0, 1.9, 0.8 Hz, 1H), 7.64 (d, J=8.3 Hz, 2H), 7.52 (d, J=2.3 Hz, 1H), 7.49 (ddd, J=8.7, 7.0, 1.9 Hz, 1H), 7.40 (d, J=8.4 Hz, 2H), 6.91 (d, J=8.6 Hz, 1H), 6.73 (ddd, J=7.1, 5.1, 0.7 Hz, 1H), 6.10 (d, J=2.4 Hz, 1H), 5.26 (s, 2H), 3.81 (s, 3H).

LCMS (ES): Found 324.4 [M+H]$^+$.

Example F

N-Hydroxy-4-((pyridin-2-yl(1,3,4-thiadiazol-2-yl)amino)methyl)benzamide

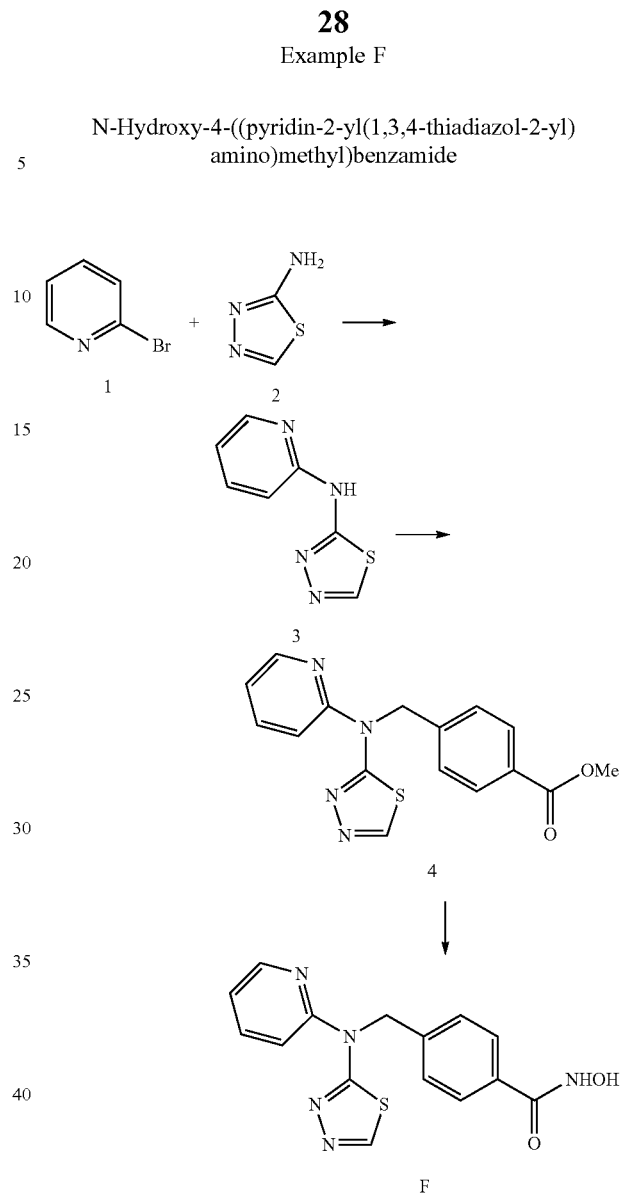

2-Bromopyridine (1) (1.0 g, 6.3 mmol), 1,3,4-thiadiazol-2-amine (2) (0.64 g, 6.3 mmol), Xantphos (0.37 g, 0.63 mmol), and Cs$_2$CO$_3$ (3.1 g, 9.4 mmol) were combined in dry 1,4-dioxane (15 mL). The reaction mixture was degassed with N$_2$(g) and placed under vacuum for 10 min. Pd$_2$(dba)$_3$ (0.29 g, 0.31 mmol) was then added and the resulting reaction mixture was then heated at 90° C. for 30 h. It was then poured onto demineralized water (200 mL), and extracted with EtOAc (3×100 mL). The organic phases were combined, dried over Na$_2$SO$_4$, filtered and subsequently concentrated in vacuo. The resulting residue was purified by flash chromatography with EtOAc/Hexane (1:1) to provide N-(pyridin-2-yl)-1,3,4-thiadiazol-2-amine (3) as a yellow solid (0.33 g, 30%).

LCMS (ES): Found 179.0 [M+H]$^+$.

NaH (60%) (53 mg, 1.3 mmol) was added portion-wise to N-(pyridin-2-yl)-1,3,4-thiadiazol-2-amine (3) (225 mg, 1.26 mmol) in DMF (8 mL) at 5° C. under Ar(g). The reaction mixture was stirred for 20 min, then methyl 4-(bromomethyl)benzoate (336 mg, 1.6 mmol) was added, and stirring was continued at 70° C. under Ar(g) for 1 h in the dark. The reaction mixture was then poured onto demineralized water (100 mL), and extracted with EtOAc (3×50 mL). The organic phases were combined, dried over Na$_2$SO$_4$, filtered and subsequently concentrated in vacuo. The resulting residue was purified by flash chromatography with EtOAc/Hexane (3:7) to furnish methyl 4-((pyridin-2-yl(1,3,4-thiadiazol-2-yl)amino)methyl)benzoate (4) as a light yellow solid (118 mg, 33%).

LCMS (ES): Found 327.3 [M+H]$^+$.

A fresh solution of NH$_2$OH in MeOH was prepared: [KOH (1.01 g, 18.1 mmol) in MeOH (20 mL) was added to NH$_2$OH.HCl (1.26 g, 18.1 mmol) in MeOH (20 mL) at 0° C.]. The reaction mixture was stirred for 20 min at 0° C., then filtered to remove salts; it was then added to methyl 4-((pyridin-2-yl(1,3,4-thiadiazol-2-yl)amino)methyl)benzoate (4) (118 mg, 0.36 mmol) followed by KOH (203 mg, 3.6 mmol) solubilized in MeOH (10 mL). The reaction mixture was stirred at rt for 21 h, and then concentrated in vacuo, poured onto brine/H$_2$O (30 mL/70 mL), and extracted with CH$_2$Cl$_2$ (3×100 mL). The organic phases were combined, dried over Na$_2$SO$_4$, filtered and subsequently concentrated in vacuo. The resulting residue was purified by flash chromatography with MeOH/CH$_2$Cl$_2$ (1:9) to provide N-hydroxy-4-((pyridin-2-yl(1,3,4-thiadiazol-2-yl)amino)methyl)benzamide, Example F, as a light brown liquid (15 mg, 13%).

$^1$H NMR (400 MHz, Methanol-d$_4$), δ$_H$ ppm: 8.96 (s, 1H), 8.44 (dd, J=5.0, 1.1 Hz, 1H), 7.72-7.78 (m, 1H), 7.69 (d, J=8.2 Hz, 2H), 7.33 (d, J=8.2 Hz, 2H), 7.06-7.11 (m, 2H), 5.79 (s, 2H).

LCMS (ES): Found 328.1 [M+H]$^+$.

Example G

N-Hydroxy-4-((pyrazin-2-yl(pyridin-2-yl)amino)methyl)benzamide

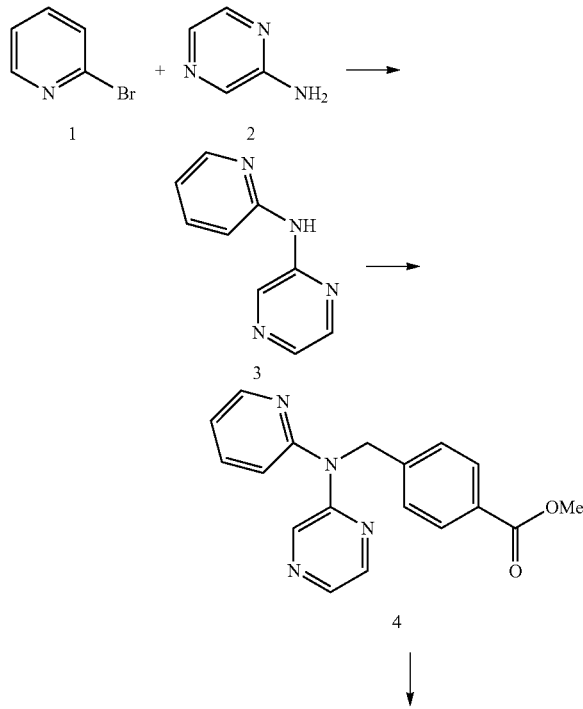

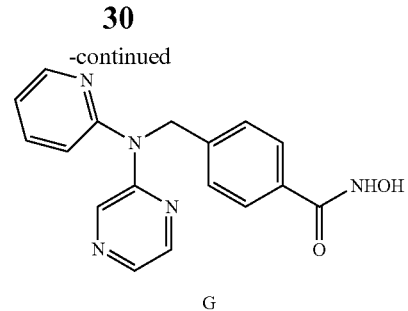

2-Bromopyridine (1) (1.0 g, 6.3 mmol), pyrazin-2-amine (2) (0.67 g, 6.9 mmol), BINAP (0.12 g, 0.18 mmol), t-BuOK (0.99 g, 8.8 mmol) were combined in dry toluene (15 mL). The reaction mixture was degassed with N$_2$(g) and placed under vacuum for 10 min. Pd$_2$(dba)$_3$ (0.11 g, 0.12 mmol) was added, and the mixture heated at 90° C. for 3 h. It was then poured onto demineralized water (200 mL), and extracted with EtOAc (3×100 mL). The organic phases were combined, dried over Na$_2$SO$_4$, filtered and subsequently concentrated in vacuo. The resulting residue was purified by flash chromatography with EtOAc/Hexane (1:1) to provide N-(pyridin-2-yl)pyrazin-2-amine (3) as a yellow solid (0.9 g, 83%).

LCMS (ES): Found 173.1 [M+H]$^+$.

NaH (60%) (61 mg, 1.52 mmol) was added portion-wise to N-(pyridin-2-yl)pyrazin-2-amine (3) (250 mg, 1.45 mmol) in DMF (10 mL) at 5° C. under Ar(g). The reaction mixture was stirred for 20 min, then methyl 4-(bromomethyl)benzoate (432 mg, 1.88 mmol) was added, and stirring was continued at 70° C. under Ar(g) for 1 h in the dark. The reaction mixture was then poured onto demineralized water (100 mL), and extracted with EtOAc (3×50 mL). The organic phases were combined, dried over Na$_2$SO$_4$, filtered and subsequently concentrated in vacuo. The resulting residue was purified by flash chromatography with EtOAc/Hexane (3:7) to furnish methyl 4-((pyrazin-2-yl(pyridin-2-yl)amino)methyl)benzoate (4) as a light yellow solid (380 mg, 81%).

LCMS (ES): Found 321.3 [M+H]$^+$.

A fresh solution of NH$_2$OH in MeOH was prepared: [KOH (3.33 g, 59.0 mmol) in MeOH (20 mL) was added to NH$_2$OH.HCl (4.1 g, 59.0 mmol) in MeOH (20 mL) at 0° C.]. The reaction mixture was stirred for 20 min at 0° C., then filtered to remove salts; it was then added to methyl 4-((pyrazin-2-yl(pyridin-2-yl)amino)methyl)benzoate (4) (380 mg, 1.1 mmol) followed by KOH (666 mg, 11.8 mmol) solubilized in MeOH (10 mL). The reaction mixture was stirred at rt for 21 h, and then concentrated in vacuo, poured onto brine/H$_2$O (30 mL/70 mL), and extracted with CH$_2$Cl$_2$ (3×100 mL). The organic phases were combined, dried over Na$_2$SO$_4$, filtered and subsequently concentrated in vacuo. The resulting residue was purified by flash chromatography with MeOH/CH$_2$Cl$_2$ (1:9) to provide N-hydroxy-4-((pyrazin-2-yl(pyridin-2-yl)amino)methyl)benzamide, Example G, as a light cream solid (20 mg, 5%).

$^1$H NMR (400 MHz, DMSO-d$_6$), δ$_H$ ppm: 11.10 (br. s., 1H), 8.99 (br. s., 1H), 8.65 (d, J=1.4 Hz, 1H), 8.32 (ddd, J=4.9, 1.9, 0.8 Hz, 1H), 8.27 (dd, J=2.7, 1.5 Hz, 1H), 8.10 (d, J=2.6 Hz, 1H), 7.74 (ddd, J=8.4, 7.3, 2.0 Hz, 1H), 7.64 (d, J=8.3 Hz, 2H), 7.36 (d, J=8.2 Hz, 2H), 7.33 (d, J=8.4 Hz, 1H), 7.06 (ddd, J=7.3, 4.9, 0.8 Hz, 1H), 5.45 (s, 2H).

LCMS (ES): Found 322.3 [M+H]$^+$.

Example H

N-Hydroxy-4-(((5-methyl-1,3,4-thiadiazol-2-yl)(pyridin-2-yl)amino)methyl)benzamide

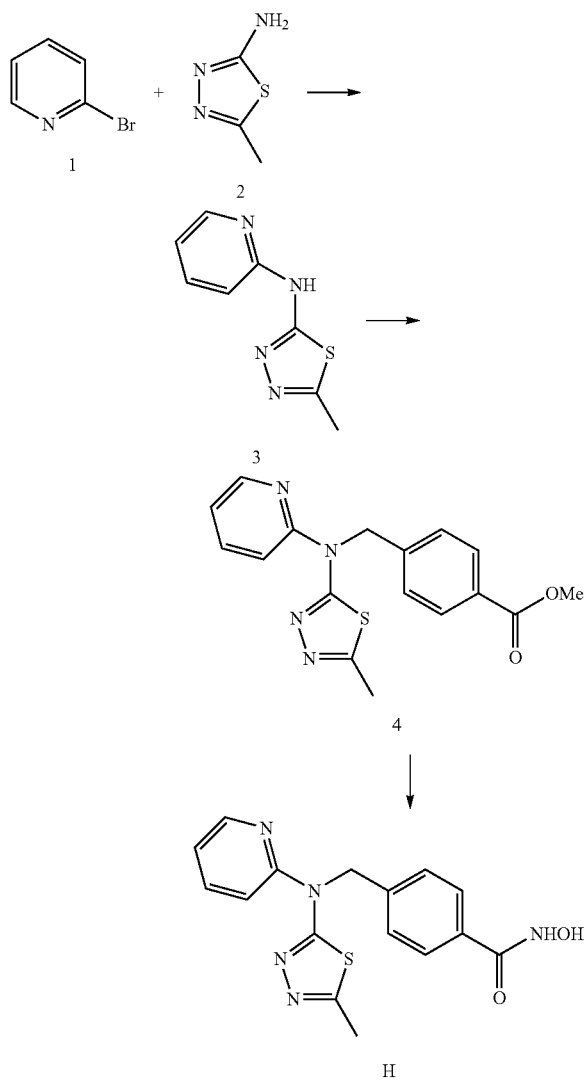

2-Bromopyridine (1) (1.0 g, 6.3 mmol), 5-methyl-1,3,4-thiadiazol-2-amine (2) (0.947 g, 8.2 mmol), Xantphos (0.366 g, 0.63 mmol), and $Cs_2CO_3$ (3.09 g, 9.4 mmol) were combined in dry 1,4-dioxane (15 mL). The reaction mixture was degassed with $N_2$(g) and placed under vacuum for 10 min. $Pd_2(dba)_3$ (0.289 g, 0.31 mmol) was then added and the resulting reaction mixture was heated at 90° C. for 30 h. It was then poured onto demineralized water (200 mL), and extracted with EtOAc (3×100 mL). The organic phases were combined, dried over $Na_2SO_4$, filtered and subsequently concentrated in vacuo. The resulting residue was purified by flash chromatography with EtOAc/Hexane (1:1) to provide 5-methyl-N-(pyridin-2-yl)-1,3,4-thiadiazol-2-amine (3) as a yellow solid (0.22 g, 18%).

LCMS (ES): Found 193.2 $[M+H]^+$.

NaH (60%) (109.3 mg, 1.3 mmol) was added portionwise to 5-methyl-N-(pyridin-2-yl)-1,3,4-thiadiazol-2-amine (3) (500 mg, 2.6 mmol) in DMF (8 mL) at 5° C. under Ar(g). The reaction mixture was stirred for 20 min, then methyl 4-(bromomethyl)benzoate (775 mg, 3.3 mmol) was added, and stirring was continued at 70° C. under Ar(g) for 1 h in the dark. The reaction mixture was then poured onto demineralized water (100 mL), and extracted with EtOAc (3×50 mL). The organic phases were combined, dried over $Na_2SO_4$, filtered and subsequently concentrated in vacuo. The resulting residue was purified by flash chromatography with EtOAc/Hexane (1:3) to furnish methyl 4-(((5-methyl-1,3,4-thiadiazol-2-yl)(pyridin-2-yl)amino)methyl)benzoate (4) as a light yellow solid (134 mg, 39%).

LCMS (ES): Found 341.4 $[M+H]^+$.

A fresh solution of $NH_2OH$ in MeOH was prepared: [KOH (1.0 g, 19.7 mmol) in MeOH (20 mL) was added to $NH_2OH.HCl$ (1.36 g, 19.7 mmol) in MeOH (20 mL) at 0° C.]. The reaction mixture was stirred for 20 min at 0° C., then filtered to remove salts; it was then added to methyl 4-(((5-methyl-1,3,4-thiadiazol-2-yl)(pyridin-2-yl)amino)methyl)benzoate (4) (134 mg, 0.39 mmol) followed by KOH (221 mg, 3.9 mmol) solubilized in MeOH (10 mL). The reaction mixture was stirred at rt for 21 h, and then concentrated in vacuo, poured onto brine/$H_2O$ (30 mL/70 mL), and extracted with $CH_2Cl_2$ (3×100 mL). The organic phases were combined, dried over $Na_2SO_4$, filtered and subsequently concentrated in vacuo. The resulting residue was purified by flash chromatography with MeOH/$CH_2Cl_2$ (1:9) to provide N-hydroxy-4-(((5-methyl-1,3,4-thiadiazol-2-yl)(pyridin-2-yl)amino)methyl)benzamide, Example H, as a light brown liquid (15 mg, 11%).

$^1$H NMR (400 MHz, Methanol-$d_4$), $\delta_H$ ppm: 8.42 (dd, J=4.9, 1.1 Hz, 1H), 7.73 (ddd, J=8.6, 7.2, 1.8 Hz, 1H), 7.69 (d, J=8.3 Hz, 2H), 7.33 (d, J=8.2 Hz, 2H), 7.02-7.09 (m, 2H), 5.72 (s, 2H), 2.65 (s, 3H).

LCMS (ES): Found 342.1 $[M+H]^+$.

Example I 4-((Benzo[d]oxazol-2-yl(pyridin-2-yl)amino)methyl)-N-hydroxybenzamide

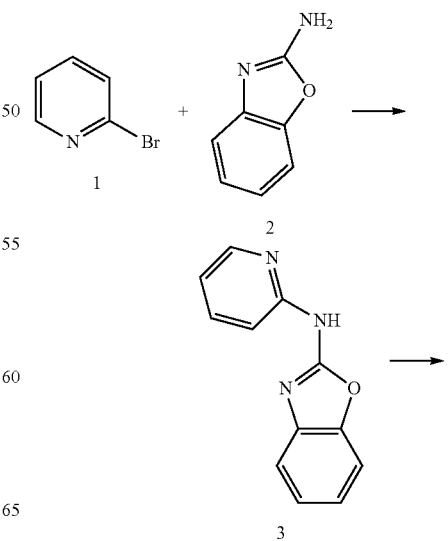

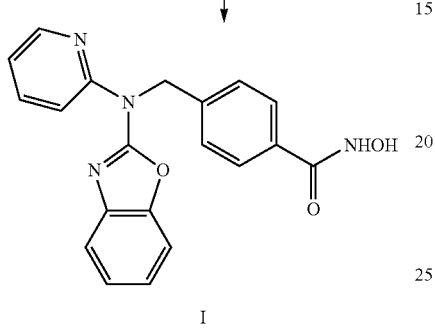

4

↓

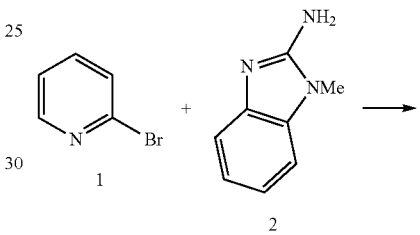

I

2-Bromopyridine (1) (1.0 g, 6.3 mmol), benzo[d]oxazol-2-amine (2) (0.871 g, 6.4 mmol), Xantphos (0.37 g, 0.63 mmol), and Cs$_2$CO$_3$ (3.09 g, 9.4 mmol) were combined in dry 1,4-dioxane (15 mL). The reaction mixture was degassed with N$_2$(g) and placed under vacuum for 10 min. Pd$_2$(dba)$_3$ (0.289 g, 0.31 mmol) was then added and the resulting reaction mixture was heated at 90° C. for 30 h. It was then poured onto demineralized water (200 mL), and extracted with EtOAc (3×100 mL). The organic phases were combined, dried over Na$_2$SO$_4$, filtered and subsequently concentrated in vacuo. The resulting residue was purified by flash chromatography with EtOAc/Hexane (1:1) to provide N-(pyridin-2-yl)benzo[d]oxazol-2-amine (3) as a yellow solid (0.8 g, 60%).

LCMS (ES): Found 212.1 [M+H]$^+$.

NaH (60%) (53 mg, 1.3 mmol) was added portion-wise to N-(pyridin-2-yl)benzo[d]oxazol-2-amine (3) (265 mg, 1.28 mmol) in DMF (8 mL) at 5° C. under Ar(g). The reaction mixture was stirred for 20 min, then methyl 4-(bromomethyl)benzoate (380 mg, 1.66 mmol) was added, and stirring was continued at 70° C. under Ar(g) for 1 h. The reaction mixture was then poured onto demineralized water (100 mL), and extracted with EtOAc (3×50 mL). The organic phases were combined, dried over Na$_2$SO$_4$, filtered and subsequently concentrated in vacuo. The resulting residue was purified by flash chromatography with EtOAc/Hexane (3:7) to furnish methyl 4-((benzo[d]oxazol-2-yl(pyridin-2-yl)amino)methyl)benzoate (4) as a light yellow solid (220 mg, 48%).

LCMS (ES): Found 360.1 [M+H]$^+$.

A fresh solution of NH$_2$OH in MeOH was prepared: [KOH (1.75 g, 31.0 mmol) in MeOH (15 mL) was added to NH$_2$OH.HCl (2.16 g, 31.0 mmol) in MeOH (15 mL) at 0° C. The reaction mixture was stirred for 20 min at 0° C., then filtered to remove salts; it was then added to methyl 4-((benzo[d]oxazol-2-yl(pyridin-2-yl)amino)methyl)benzoate (4) (220 mg, 0.62 mmol) followed by KOH (348 mg, 6.2 mmol) solubilized in MeOH (5 mL). The reaction mixture was stirred at rt for 21 h, and then concentrated in vacuo, poured onto brine/H$_2$O (30 mL/70 mL), and extracted with CH$_2$Cl$_2$ (3×100 mL). The organic phases were combined, dried over Na$_2$SO$_4$, filtered and subsequently concentrated in vacuo. The resulting residue was purified by flash chromatography with MeOH/CH$_2$Cl$_2$ (1:9) to provide 4-((benzo[d]oxazol-2-yl(pyridin-2-yl)amino)methyl)-N-hydroxybenzamide, Example I, as a light orange solid (50 mg, 23%).

$^1$H NMR (400 MHz, DMSO-d$_6$), δ$_H$ ppm: 11.12 (br. s., 1H), 9.00 (br. s., 1H), 8.40 (dd, J=4.7, 1.8 Hz, 1H), 8.17 (d, J=8.4 Hz, 1H), 7.88-7.94 (m, 1H), 7.65 (d, J=8.2 Hz, 2H), 7.47-7.55 (m, 2H), 7.41 (d, J=8.2 Hz, 2H), 7.26 (t, J=7.8 Hz, 1H), 7.14-7.22 (m, 2H), 5.59 (s, 2H).

LCMS (ES): Found 361.1 [M+H]$^+$.

Example J

N-Hydroxy-4-(((1-methyl-1H-benzo[d]imidazol-2-yl)(pyridin-2-yl)amino)methyl)benzamide

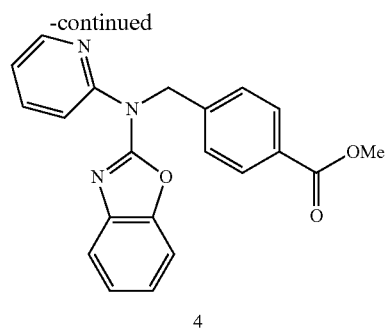

2

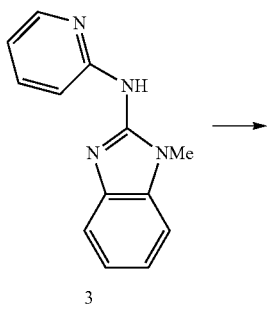

3

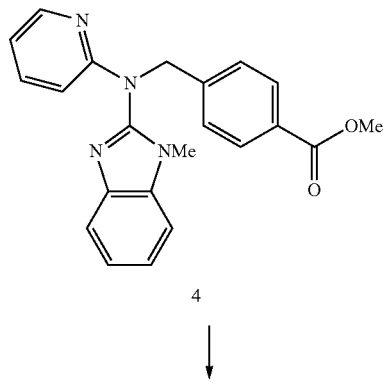

4

↓

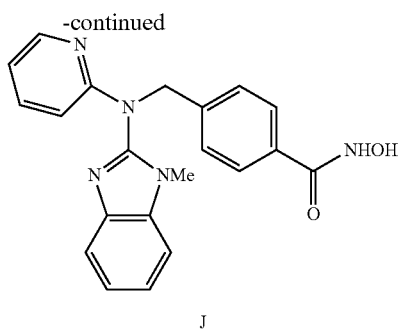

J

2-Bromopyridine (1) (1.0 g, 6.3 mmol), 1-methyl-1H-pyrazol-3-amine (2) (1.21 g, 6.9 mmol), Xantphos (0.37 g, 0.63 mmol), and Cs$_2$CO$_3$ (4.1 g, 12.6 mmol) were combined in dry 1,4-dioxane (15 mL). The reaction mixture was degassed with N$_2$(g) and placed under vacuum for 10 min. Pd$_2$(dba)$_3$ (0.29 g, 0.31 mmol) was then added and the resulting reaction mixture was heated at 90° C. for 30 h. It was then poured onto demineralized water (200 mL), and extracted with EtOAc (3×100 mL). The organic phases were combined, dried over Na$_2$SO$_4$, filtered and subsequently concentrated in vacuo. The resulting residue was purified by flash chromatography with EtOAc/Hexane (1:1) to provide 1-methyl-N-(pyridin-2-yl)-1H-benzo[d]imidazol-2-amine (3) as a yellow solid (0.35 g, 25%).

LCMS (ES): Found 225.1 [M+H]$^+$.

NaH (60%) (32.8 mg, 0.82 mmol) was added portion-wise to 1-methyl-N-(pyridin-2-yl)-1H-benzo[d]imidazol-2-amine (3) (175 mg, 0.78 mmol) in DMF (5 mL) at 5° C. under Ar(g). The reaction mixture was stirred for 20 min, then methyl 4-(bromomethyl)benzoate (232 mg, 1.01 mmol) was added, and stirring was continued at 70° C. under Ar(g) for 1 h in the dark. The reaction mixture was then poured onto demineralized water (100 mL), and extracted with EtOAc (3×50 mL). The organic phases were combined, dried over Na$_2$SO$_4$, filtered and subsequently concentrated in vacuo. The residue was purified by flash chromatography with EtOAc/Hexane (3:7) to furnish methyl 4-(((1-methyl-1H-benzo[d]imidazol-2-yl)(pyridin-2-yl)amino)methyl)benzoate (4) as a light yellow solid (42 mg, 16%).

LCMS (ES): Found 373.2 [M+H]$^+$.

A fresh solution of NH$_2$OH in MeOH was prepared: [KOH (1.07 g, 19.0 mmol) in MeOH (10 mL) was added to NH$_2$OH.HCl (530 mg, 19.0 mmol) in MeOH (10 mL) at 0° C.]. The reaction mixture was stirred for 20 min at 0° C., then filtered to remove salts; it was then added to methyl 4-(((1-methyl-1H-benzo[d]imidazol-2-yl)(pyridin-2-yl)amino)methyl)benzoate (4) (142 mg, 0.38 mmol) followed by KOH (214 mg, 3.8 mmol) solubilized in MeOH (5 mL). The reaction mixture was stirred at rt for 21 h, and then concentrated in vacuo, poured onto brine/H$_2$O (30 mL/70 mL), and extracted with CH$_2$Cl$_2$ (3×100 mL). The organic phases were combined, dried over Na$_2$SO$_4$, filtered and subsequently concentrated in vacuo. The resulting residue was purified by flash chromatography with MeOH/CH$_2$Cl$_2$ (10:90) to provide N-hydroxy-4-(((1-methyl-1H-benzo[d]imidazol-2-yl)(pyridin-2-yl)amino)methyl)benzamide, Example J, as an off white solid (9 mg, 7%).

$^1$H NMR (400 MHz, Methanol-d$_4$), δ$_H$ ppm: 8.23 (dd, J=5.0, 1.1 Hz, 1H), 7.65 (d, J=8.3 Hz, 2H), 7.58-7.63 (m, 2H), 7.52 (d, J=8.2 Hz, 2H), 7.41 (dd, J=6.8, 1.9 Hz, 1H), 7.24-7.32 (m, 2H), 6.92 (dd, J=6.8, 5.1 Hz, 1H), 6.56 (d, J=8.4 Hz, 1H), 5.37 (s, 2H), 3.37-3.42 (m, 3H).

LCMS (ES): Found 374.3 [M+H]$^+$.

Example K

N-Hydroxy-4-((pyridin-2-yl(1,2,4-thiadiazol-5-yl)amino)methyl)benzamide

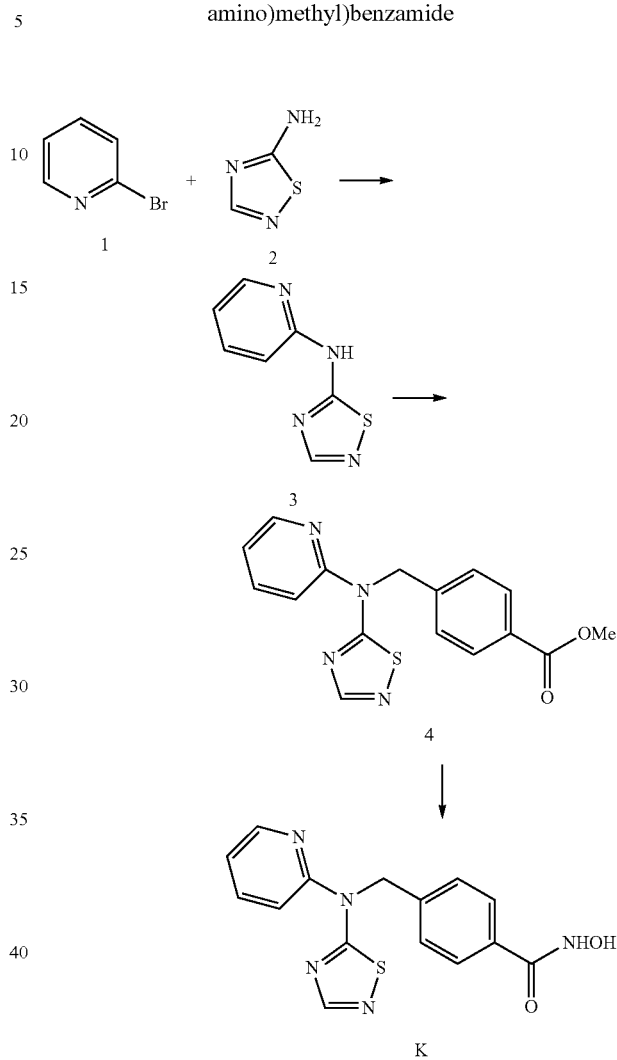

2-Bromopyridine (1) (1.0 g, 6.3 mmol), 1,2,4-thiadiazol-5-amine (2) (0.830 g, 8.22 mmol), Xantphos (0.366 g, 0.63 mmol), and Cs$_2$CO$_3$ (3.09 g, 9.4 mmol) were combined in dry 1,4-dioxane (15 mL). The reaction mixture was degassed with N$_2$(g) and placed under vacuum for 10 min. Pd$_2$(dba)$_3$ (0.29 g, 0.31 mmol) was then added and the resulting reaction mixture was heated at 90° C. for 30 h. It was then poured onto demineralized water (200 mL), and extracted with EtOAc (3×100 mL). The organic phases were combined, dried over Na$_2$SO$_4$, filtered and subsequently concentrated in vacuo. The resulting residue was purified by flash chromatography with EtOAc/Hexane (1:1) to provide N-(pyridin-2-yl)-1,2,4-thiadiazol-5-amine (3) as a yellow solid (0.188 g, 16%).

LCMS (ES): Found 179.0 [M+H]$^+$

NaH (60%) (49 mg, 1.23 mmol) was added portion-wise to N-(pyridin-2-yl)-1,2,4-thiadiazol-5-amine (3) (210 mg, 1.19 mmol) in DMF (8 mL) at 5° C. under Ar(g). The reaction mixture was stirred for 20 min, then methyl 4-(bromomethyl)benzoate (351 mg, 1.5 mmol) was added, and stirring was continued at 70° C. under Ar(g) for 1 h in the dark. The reaction mixture was then poured onto demineralized water (100 mL), and extracted with EtOAc (3×50 mL). The organic phases were combined, dried over Na$_2$SO$_4$, filtered and subsequently concentrated in vacuo. The resulting residue was purified by flash chromatography with EtOAc/Hexane (3:7) to furnish methyl 4-((pyridin-2-yl(1,2,4-thiadiazol-5-yl)amino)methyl)benzoate (4) as a light yellow solid (110 mg, 28%).

LCMS (ES): Found 327.4 [M+H]$^+$.

A fresh solution of NH$_2$OH in MeOH was prepared: [KOH (949 mg, 16.9 mmol) in MeOH (10 mL) was added to NH$_2$OH.HCl (1.17 g, 16.9 mmol) in MeOH (10 mL) at 0° C.]. The reaction mixture was stirred for 20 min at 0° C., then filtered to remove salts; it was then added to methyl 4-((pyridin-2-yl(1,2,4-thiadiazol-5-yl)amino)methyl)benzoate (4) (110 mg, 0.33 mmol) followed by KOH (185 mg, 3.3 mmol) solubilized in MeOH (5 mL). The reaction mixture was stirred at rt for 21 h, and then concentrated in vacuo, poured onto brine/H$_2$O (30 mL/70 mL), and extracted with CH$_2$Cl$_2$ (3×100 mL). The organic phases were combined, dried over Na$_2$SO$_4$, filtered and subsequently concentrated in vacuo. The resulting residue was purified by flash chromatography with MeOH/CH$_2$Cl$_2$ (1:9) to provide N-hydroxy-4-((Pyridin-2-yl(1,2,4-thiadiazol-5-yl)amino)methyl) benzamide, Example K, as a light orange solid (11 mg, 10%).

$^1$H NMR (400 MHz, Methanol-d$_4$), δ$_H$ ppm: 8.54 (d, J=4.3 Hz, 1H), 8.22-8.31 (m, 1H), 7.81 (br. s., 1H), 7.65-7.76 (m, 2H), 7.08-7.38 (m, 4H), 5.82 (s, 2H).

LCMS (ES): Found 328.0 [M+H]$^+$.

Example L 4-(((5-Fluoropyridin-2-yl)(pyrazin-2-yl)amino) methyl)-N-hydroxybenzamide

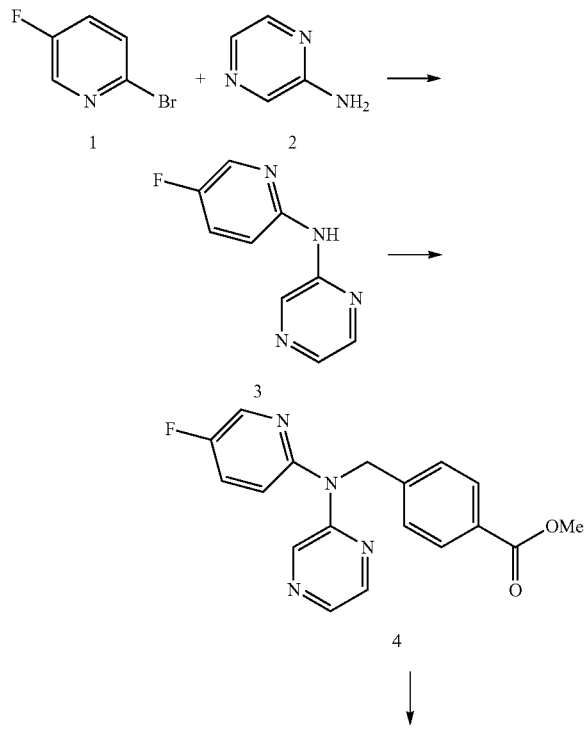

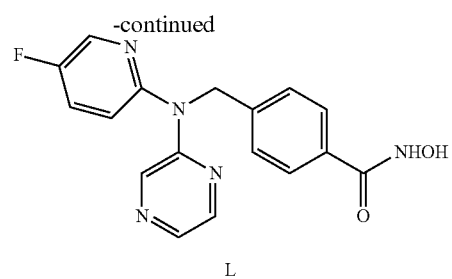

L

2-Bromo-5-fluoropyridine (1) (1.0 g, 5.71 mmol), pyrazin-2-amine (2) (543 mg, 5.71 mmol), Xantphos (0.330 g, 0.57 mmol), Cs$_2$CO$_3$ (2.79 g, 8.56 mmol) were combined in dry 1,4-dioxane (15 mL). The reaction mixture was degassed with N$_2$(g), and placed under vacuum for 10 min. Pd$_2$(dba)$_3$ (0.26 g, 0.28 mmol) was added and the reaction mixture was then heated at 90° C. for 30 h. It was then poured onto demineralized water (200 mL), and extracted with EtOAc (3×100 mL). The organic phases were combined, dried over Na$_2$SO$_4$, filtered and subsequently concentrated in vacuo. The resulting residue was purified by flash chromatography with EtOAc/Hexane (1:1) to provide N-(5-fluoropyridin-2-yl)pyrazin-2-amine (3) as a yellow solid (0.56 g, 51%).

LCMS (ES): Found 191.1 [M+H]$^+$.

NaH (60%) (39 mg, 0.99 mmol) was added portion-wise to N-(5-fluoropyridin-2-yl)pyrazin-2-amine (3) (180 mg, 0.94 mmol) in DMF (5 mL) at 5° C. under Ar(g). The reaction mixture was stirred for 20 min, then methyl 4-(bromomethyl)benzoate (281 mg, 1.23 mmol) was added, and stirring was continued at 70° C. under Ar(g) for 1 h. The reaction mixture was then poured onto demineralized water (100 mL), and extracted with EtOAc (3×50 mL). The organic phases were combined, dried over Na$_2$SO$_4$, filtered and subsequently concentrated in vacuo. The resulting residue was purified by flash chromatography with EtOAc/Hexane (3:7) to furnish methyl 4-(((5-fluoropyridin-2-yl)(pyrazin-2-yl)amino)methyl)benzoate (4) as a light yellow solid (190 mg, 59%).

LCMS (ES): Found 339.1 [M+H]$^+$.

A fresh solution of NH$_2$OH in MeOH was prepared: [KOH (1.57 g, 28.1 mmol) in MeOH (15 mL) was added to NH$_2$OH.HCl (1.95 g, 28.1 mmol) in MeOH (15 mL) at 0° C.]. The reaction mixture was stirred for 20 min at 0° C., then filtered to remove salts; it was then added to methyl 4-(((5-fluoropyridin-2-yl)(pyrazin-2-yl)amino)methyl)benzoate (4) (190 mg, 0.56 mmol) followed by KOH (315 mg, 5.6 mmol) solubilized in MeOH (5 mL). The reaction mixture was stirred at rt for 21 h, and then concentrated in vacuo, poured onto brine/H$_2$O (30 mL/70 mL), and extracted with CH$_2$Cl$_2$ (3×100 mL). The organic phases were combined, dried over Na$_2$SO$_4$, filtered and subsequently concentrated in vacuo. The resulting residue was purified by flash chromatography with MeOH/CH$_2$Cl$_2$ (1:9) to provide 4-(((5-fluoropyridin-2-yl)(pyrazin-2-yl)amino) methyl)-N-hydroxybenzamide, Example L, as a creamish solid (40 mg, 21%).

$^1$H NMR (400 MHz, DMSO-d$_6$), δ$_H$ ppm: 11.08 (br. s, 1H), 8.84-9.09 (m, 1H), 8.54 (d, J=1.4 Hz, 1H), 8.34 (d, J=3.1 Hz, 1H), 8.24 (dd, J=2.7, 1.5 Hz, 1H), 8.09 (d, J=2.7 Hz, 1H), 7.72 (ddd, J=9.0, 8.2, 3.1 Hz, 1H), 7.64 (d, J=8.3 Hz, 2H), 7.46 (dd, J=9.1, 3.7 Hz, 1H), 7.37 (d, J=8.3 Hz, 2H), 5.42 (s, 2H)

LCMS (ES): Found 340.1 [M+H]$^+$.

Example M 4-(((5-Fluoropyridin-2-yl)(3-methyl-1,2,4-oxadiazol-5-yl)amino)methyl)-N-hydroxybenzamide

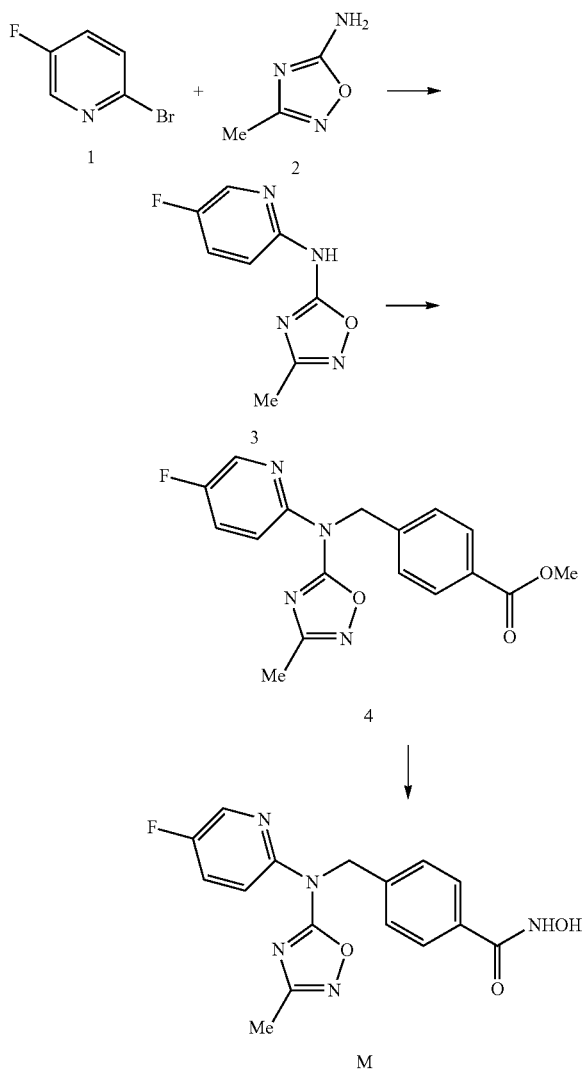

2-Bromo-5-fluoropyridine (1) (1.0 g, 5.71 mmol), 3-methyl-1,2,4-oxadiazol-5-amine (2) (566 mg, 5.71 mmol), Xantphos (0.330 g, 0.57 mmol), and Cs$_2$CO$_3$ (2.79 g, 8.56 mmol) were combined in dry 1,4-dioxane (15 mL). The reaction mixture was degassed with N$_2$(g) and placed under vacuum for 10 min. Pd$_2$(dba)$_3$ (0.261 g, 0.28 mmol) was then added and the resulting reaction mixture was heated at 90° C. for 30 h. It was then poured onto demineralized water (200 mL), and extracted with EtOAc (3×100 mL). The organic phases were combined, dried over Na$_2$SO$_4$, filtered and subsequently concentrated in vacuo. The resulting residue was purified by flash chromatography with EtOAc/Hexane (1:1) to provide N-(5-fluoropyridin-2-yl)-3-methyl-1,2,4-oxadiazol-5-amine (3) as a yellow solid (0.70 g, 63%).

LCMS (ES): Found 195.0 [M+H]$^+$.

NaH (60%) (56 mg, 1.4 mmol) was added portion-wise to N-(5-fluoropyridin-2-yl)-3-methyl-1,2,4-oxadiazol-5-amine (3) (260 mg, 1.34 mmol) in DMF (10 mL) at 5° C. under Ar(g). The reaction mixture was stirred for 20 min, then methyl 4-(bromomethyl)benzoate (398 mg, 1.7 mmol) was added, and stirring was continued at 70° C. under Ar(g) for 1 h. The reaction mixture was then poured onto demineralized water (100 mL), and extracted with EtOAc (3×50 mL). The organic phases were combined, dried over Na$_2$SO$_4$, filtered and subsequently concentrated in vacuo. The resulting residue was purified by flash chromatography with EtOAc/Hexane (3:7) to furnish methyl-4-(((5-fluoropyridin-2-yl)(3-methyl-1,2,4-oxadiazol-5-yl)amino)methyl)benzoate (4) as a light yellow solid (170 mg, 37%).

LCMS (ES): Found 343.1 [M+H]$^+$.

A fresh solution of NH$_2$OH in MeOH was prepared: [KOH (1.39 g, 24.8 mmol) in MeOH (15 mL) was added to NH$_2$OH.HCl (1.72 g, 24.8 mmol) in MeOH (15 mL) at 0° C.]. The reaction mixture was stirred for 20 min at 0° C., then filtered to remove salts; it was then added to methyl 4-(((5-fluoropyridin-2-yl)(3-methyl-1,2,4-oxadiazol-5-yl)amino)methyl)benzoate (4) (170 mg, 0.49 mmol) followed by KOH (278 mg, 4.9 mmol) solubilized in MeOH (5 mL). The reaction mixture was stirred at rt for 21 h, and then concentrated in vacuo, poured onto brine/H$_2$O (30 mL/70 mL), and extracted with CH$_2$Cl$_2$ (3×100 mL). The organic phases were combined, dried over Na$_2$SO$_4$, filtered and subsequently concentrated in vacuo. The resulting residue was purified by flash chromatography with MeOH/CH$_2$Cl$_2$ (1:9) to provide 4-(((5-fluoropyridin-2-yl)(3-methyl-1,2,4-oxadiazol-5-yl)amino)methyl)-N-hydroxybenzamide, Example M, as a light orange solid (20 mg, 12%).

$^1$H NMR (400 MHz, DMSO-d$_6$), δ$_H$ ppm: 11.11 (br. s., 1H), 9.01 (br. s., 1H), 8.43 (d, J=3.0 Hz, 1H), 8.11 (dd, J=9.2, 3.8 Hz, 1H), 7.89 (td, J=8.6, 3.1 Hz, 1H), 7.67 (d, J=8.3 Hz, 2H), 7.34 (d, J=8.2 Hz, 2H), 5.43 (s, 2H), 2.22 (s, 4H).

LCMS (ES): Found 344.1 [M+H]$^+$.

Example N 4-(((5-Fluoropyridin-2-yl)(1-methyl-1H-benzo[d]imidazol-2-yl)amino)methyl)-N-hydroxybenzamide

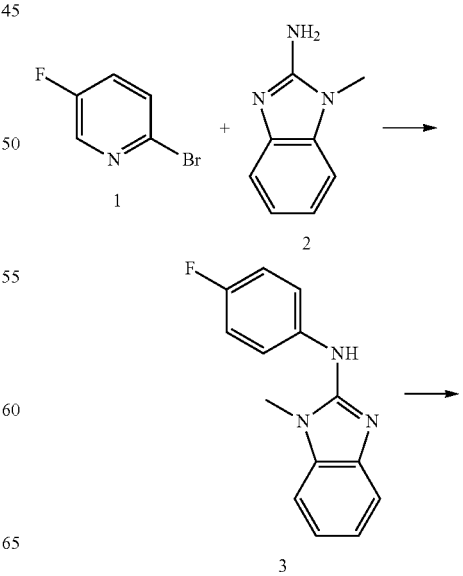

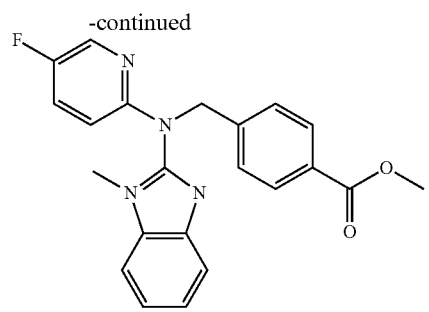

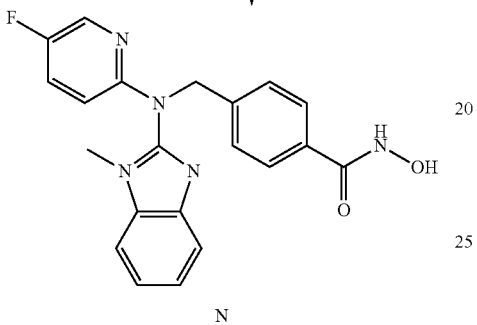

2-Bromo-5-fluoropyridine (1) (1.0 g, 5.71 mmol), 1-methyl-1H-benzo[d]imidazol-2-amine (2) (840 mg, 5.71 mmol), Xantphos (0.33 g, 0.57 mmol), and Cs$_2$CO$_3$ (2.79 g, 8.56 mmol) were combined in dry 1,4-dioxane (15 mL). The reaction mixture was degassed with N$_2$(g) and placed under vacuum for 10 min. Pd$_2$(dba)$_3$ (0.26 g, 0.28 mmol) was then added and the resulting reaction mixture was heated at 90° C. for 30 h. It was then poured onto demineralized water (200 mL), and extracted with EtOAc (3×100 mL). The organic phases were combined, dried over Na$_2$SO$_4$, filtered and subsequently concentrated in vacuo. The resulting residue was purified by flash chromatography with EtOAc/Hexane (1:1) to provide N-(5-fluoropyridin-2-yl)-1-methyl-1H-benzo[d]imidazol-2-amine (3) as a yellow solid (0.56 g, 41%).

LCMS (ES): Found 243.1 [M+H]$^+$.

NaH (60%) (27 mg, 0.66 mmol) was added portion-wise to N-(5-fluoropyridin-2-yl)-1-methyl-1H-benzo[d]imidazol-2-amine (3) (154 mg, 0.63 mmol) in DMF (5 mL) at 5° C. under Ar(g). The reaction mixture was stirred for 20 min, then methyl 4-(bromomethyl)benzoate (189 mg, 0.82 mmol) was added, and stirring was continued at 70° C. under Ar(g) for 1 h. The reaction mixture was then poured onto demineralized water (100 mL), and extracted with EtOAc (3×50 mL). The organic phases were combined, dried over Na$_2$SO$_4$, filtered and subsequently concentrated in vacuo. The resulting residue was purified by flash chromatography with EtOAc/Hexane (3:7) to furnish methyl 4-(((5-fluoropyridin-2-yl)(1-methyl-1H-benzo[d]imidazol-2-yl)amino)methyl)benzoate (4) as a light yellow solid (165 mg, 66%).

LCMS (ES): Found 391.2 [M+H]$^+$.

A fresh solution of NH$_2$OH in MeOH was prepared: [KOH (1.20 g, 21.4 mmol) in MeOH (15 mL) was added to NH$_2$OH.HCl (1.48 g, 21.4 mmol) in MeOH (15 mL) at 0° C.]. The reaction mixture was stirred for 20 min at 0° C., then filtered to remove salts; it was then added to methyl 4-(((5-fluoropyridin-2-yl)(1-methyl-1H-benzo[d]imidazol-2-yl)amino)methyl)benzoate (4) (165 mg, 0.40 mmol) followed by KOH (240 mg, 4.0 mmol) solubilized in MeOH (5 mL). The reaction mixture was stirred at rt for 21 h, and then concentrated in vacuo, poured onto brine/H$_2$O (30 mL/70 mL), and extracted with CH$_2$Cl$_2$ (3×100 mL). The organic phases were combined, dried over Na$_2$SO$_4$, filtered and subsequently concentrated in vacuo. The resulting residue was purified by flash chromatography with MeOH/CH$_2$Cl$_2$ (1:9) to provide 4-(((5-fluoropyridin-2-yl)(1-methyl-1H-benzo[d]imidazol-2-yl)amino)methyl)-N-hydroxybenzamide, Example N, as a light orange solid (20 mg, 12%).

$^1$H NMR (400 MHz, DMSO-d$_6$), δ$_H$ ppm: 8.19 (d, J=2.9 Hz, 1H), 7.66 (d, J=8.2 Hz, 1H), 7.55-7.63 (m, 3H), 7.42-7.54 (m, 3H), 7.15-7.27 (m, 2H), 6.74 (dd, J=9.2, 3.4 Hz, 1H), 5.22-5.31 (m, 2H), 3.42 (s, 3H).

LCMS (ES): Found 392.25 [M+H]$^+$.

Example O 4-(((5-Fluoropyridin-2-yl)(1-methyl-1H-pyrazol-3-yl)amino)methyl)-N-hydroxybenzamide

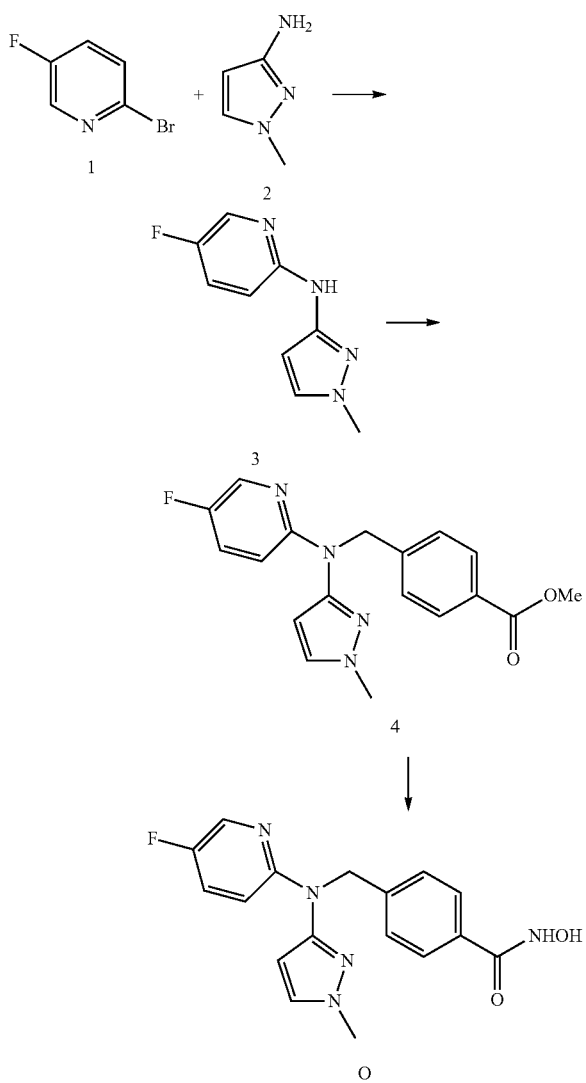

2-Bromo-5-fluoropyridine (1) (1.0 g, 5.71 mmol), 1-methyl-1H-pyrazol-3-amine (2) (554 mg, 5.71 mmol), Xantphos (0.330 g, 0.57 mmol), and Cs$_2$CO$_3$ (2.79 g, 8.56 mmol) were combined in dry 1,4-dioxane (15 mL). The reaction mixture was degassed with N$_2$(g) and placed under vacuum for 10 min. Pd$_2$(dba)$_3$ (0.261 g, 0.28 mmol) was then added and the resulting reaction mixture was heated at 90° C. for 30 h. It was then poured onto demineralized water (200 mL), and extracted with EtOAc (3×100 mL). The organic phases were combined, dried over Na$_2$SO$_4$, filtered and subsequently concentrated in vacuo. The resulting residue was purified by flash chromatography with EtOAc/Hexane (1:1) to provide 5-fluoro-N-(1-methyl-1H-pyrazol-3-yl)pyridin-2-amine (3) as a yellow solid (0.65 g, 61%).

LCMS (ES): Found 193.0 [M+H]$^+$.

NaH (60%) (50 mg, 1.25 mmol) was added portion-wise to 5-fluoro-N-(1-methyl-1H-pyrazol-3-yl)pyridin-2-amine (3) (230 mg, 1.19 mmol) in DMF (10 mL) at 5° C. under Ar(g). The reaction mixture was stirred for 20 min, then methyl 4-(bromomethyl)benzoate (356 mg, 1.55 mmol) was added, and stirring was continued at 70° C. under Ar(g) for 1 h. The reaction mixture was then poured onto demineralized water (100 mL), and extracted with EtOAc (3×50 mL). The organic phases were combined, dried over Na$_2$SO$_4$, filtered and subsequently concentrated in vacuo. The resulting residue was purified by flash chromatography with EtOAc/Hexane (3:7) to furnish methyl 4-(((5-fluoropyridin-2-yl)(1-methyl-1H-pyrazol-3-yl)amino)methyl)benzoate (4) as a light yellow solid (312 mg, 76%).

LCMS (ES): Found 341.1 [M+H]$^+$.

A fresh solution of NH$_2$OH in MeOH was prepared: [KOH (2.57 g, 45.8 mmol) in MeOH (15 mL) was added to NH$_2$OH.HCl (3.18 g, 45.8 mmol) in MeOH (15 mL) at 0° C.]. The reaction mixture was stirred for 20 min at 0° C., then filtered to remove salts; it was then added to methyl methyl 4-(((5-fluoropyridin-2-yl)(1-methyl-1H-pyrazol-3-yl)amino)methyl)benzoate (4) (312 mg, 0.91 mmol) followed by KOH (512 mg, 9.1 mmol) solubilized in MeOH (5 mL). The reaction mixture was stirred at rt for 21 h, and then concentrated in vacuo, poured onto brine/H$_2$O (30 mL/70 mL), and extracted with CH$_2$Cl$_2$ (3×100 mL). The organic phases were combined, dried over Na$_2$SO$_4$, filtered and subsequently concentrated in vacuo. The resulting residue was purified by flash chromatography with MeOH/CH$_2$Cl$_2$ (1:9) to provide 4-(((5-fluoropyridin-2-yl)(1-methyl-1H-pyrazol-3-yl)amino)methyl)-N-hydroxybenzamide, Example O, as a cream solid (65 mg, 20%).

$^1$H NMR (400 MHz, DMSO-d$_6$), δ$_H$ ppm: 11.11 (br. s, 1H), 8.96 (br. s, 1H), 8.10 (d, J=3.1 Hz, 1H), 7.59-7.66 (m, 3H), 7.51 (ddd, J=9.3, 8.2, 3.1 Hz, 1H), 7.31 (d, J=8.1 Hz, 2H), 7.19 (dd, J=9.4, 3.7 Hz, 1H), 6.13 (d, J=2.3 Hz, 1H), 5.21 (s, 2H), 3.76 (s, 3H).

LCMS (ES): Found 342.1 [M+H]$^+$.

Example P 4-((Benzo[d]oxazol-2-yl(5-fluoropyridin-2-yl)amino)methyl)-N-hydroxybenzamide

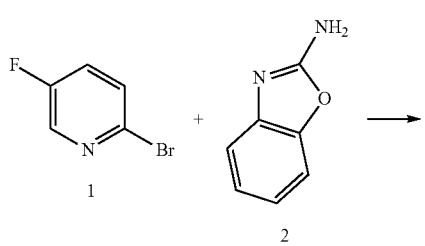

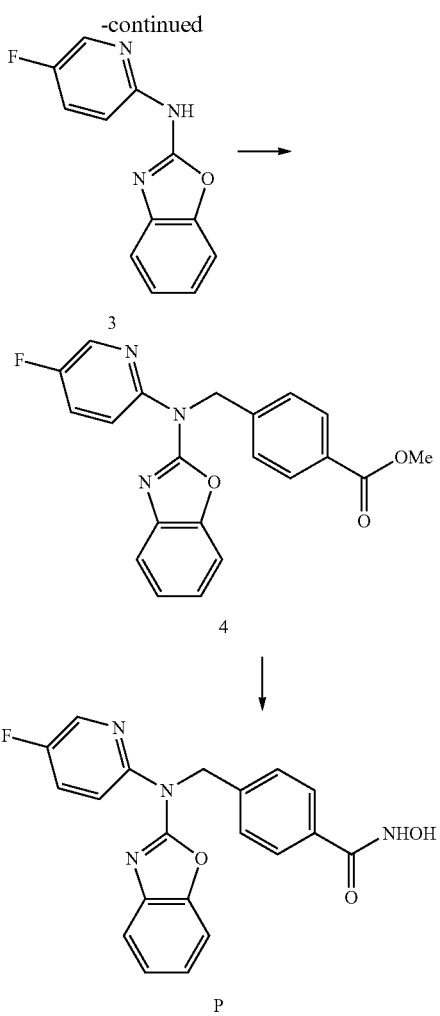

2-Bromo-5-fluoropyridine (1) (1.0 g, 5.71 mmol), benzo[d]oxazol-2-amine (2) (766 mg, 5.71 mmol), Xantphos (0.33 g, 0.57 mmol), and Cs$_2$CO$_3$ (2.79 g, 8.56 mmol) were combined in dry 1,4-dioxane (15 mL). The reaction mixture was degassed with N$_2$(g) and placed under vacuum for 10 min. Pd$_2$(dba)$_3$ (0.261 g, 0.28 mmol) was then added and the resulting reaction mixture was heated at 90° C. for 30 h. It was then poured onto demineralized water (200 mL), and extracted with EtOAc (3×100 mL). The organic phases were combined, dried over Na$_2$SO$_4$, filtered and subsequently concentrated in vacuo. The resulting residue was purified by flash chromatography with EtOAc/Hexane (1:1) to provide N-(5-fluoropyridin-2-yl)benzo[d]oxazol-2-amine (3) as a yellow solid (0.6 g, 46%).

LCMS (ES): Found 230.1 [M+H]$^+$.

NaH (60%) (36 mg, 0.91 mmol) was added portion-wise to N-(5-fluoropyridin-2-yl)benzo[d]oxazol-2-amine (3) (200 mg, 0.87 mmol) in DMF (8 mL) at 5° C. under Ar(g). The reaction mixture was stirred for 20 min, then methyl 4-(bromomethyl)benzoate (259 mg, 1.13 mmol) was added, and stirring was continued at 70° C. under Ar(g) for 1 h. The reaction mixture was then poured onto demineralized water (100 mL), and extracted with EtOAc (3×50 mL). The organic phases were combined, dried over Na$_2$SO$_4$, filtered and subsequently concentrated in vacuo. The resulting residue was purified by flash chromatography with EtOAc/

Hexane (3:7) to furnish methyl 4-((benzo[d]oxazol-2-yl(5-fluoropyridin-2-yl)amino)methyl)benzoate (4) as a light yellow solid (144 mg, 43%).

LCMS (ES): Found 378.1 [M+H]⁺.

A fresh solution of NH₂OH in MeOH was prepared: [KOH (1.07 g, 19.0 mmol) in MeOH (15 mL) was added to NH₂OH.HCl (1.33 g, 19.0 mmol) in MeOH (15 mL) at 0° C.]. The reaction mixture was stirred for 20 min at 0° C., then filtered to remove salts; it was then added to methyl 4-((benzo[d]oxazol-2-yl(5-fluoropyridin-2-yl)amino) methyl)benzoate (4) (144 mg, 0.38 mmol) followed by KOH (214 mg, 3.8 mmol) solubilized in MeOH (5 mL). The reaction mixture was stirred at rt for 21 h, and then concentrated in vacuo, poured onto brine/H₂O (30 mL/70 mL), and extracted with CH₂Cl₂ (3×100 mL). The organic phases were combined, dried over Na₂SO₄, filtered and subsequently concentrated in vacuo. The resulting residue was purified by flash chromatography with MeOH/CH₂Cl₂ (1:9) to provide 4-((benzo[d]oxazol-2-yl(5-fluoropyridin-2-yl) amino)methyl)-N-hydroxybenzamide, Example P, as an orange solid (30 mg, 20%).

¹H NMR (400 MHz, DMSO-d₆), δ$_H$ ppm: 11.13 (br. s, 1H), 9.01 (br. s., 1H), 8.41 (d, J=3.1 Hz, 1H), 8.25 (dd, J=9.2, 3.8 Hz, 1H), 7.89 (ddd, J=9.2, 8.1, 3.1 Hz, 1H), 7.66 (d, J=8.3 Hz, 2H), 7.47-7.54 (m, 2H), 7.41 (d, J=8.2 Hz, 2H), 7.26 (td, J=7.7, 1.1 Hz, 1H), 7.13-7.20 (m, 1H), 5.54 (s, 2H).

LCMS (ES): Found 379.1 [M+H]⁺.

Example Q 4-(((4-(4-Fluorophenyl)pyridin-2-yl)(1-methyl-1H-pyrazol-3-yl)amino)methyl)-N-hydroxybenzamide

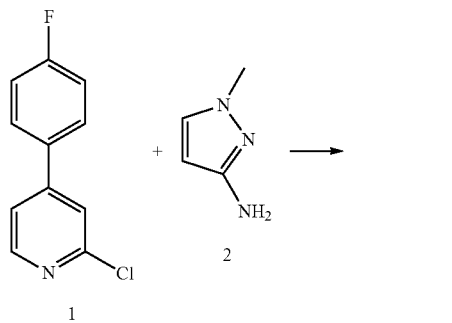

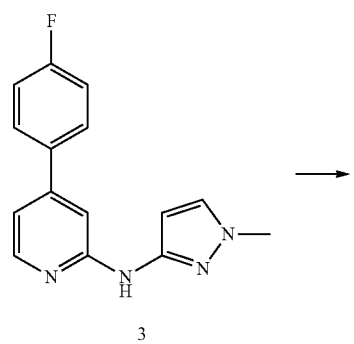

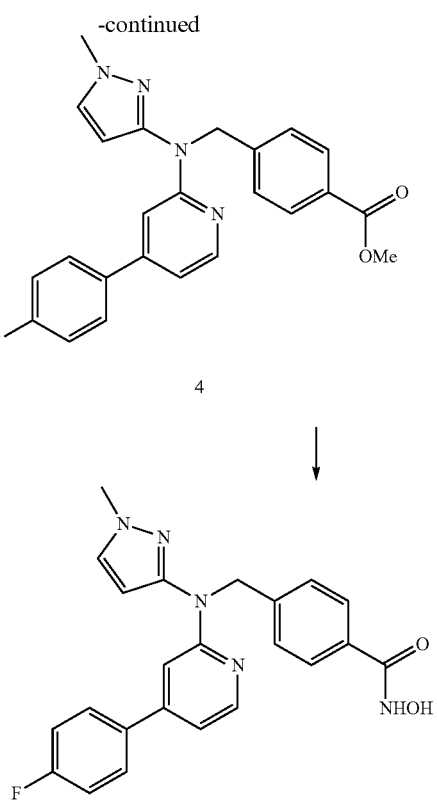

2-Chloro-4-(4-fluorophenyl)pyridine (1) (1.0 g, 4.8 mmol), 1-methyl-1H-pyrazol-3-amine (2) (470 mg, 4.8 mmol), Xantphos (0.28 g, 0.48 mmol), and Cs₂CO₃ (2.35 g, 7.24 mmol) were combined in dry 1,4-dioxane (15 mL). The reaction mixture was degassed with N₂(g) and placed under vacuum for 10 min. Pd₂(dba)₃ (0.22 g, 0.24 mmol) was then added and the resulting reaction mixture was heated at 90° C. for 30 h. It was then poured onto demineralized water (200 mL), and extracted with EtOAc (3×100 mL). The organic phases were combined, dried over Na₂SO₄, filtered and subsequently concentrated in vacuo. The resulting residue was purified by flash chromatography with EtOAc/Hexane (1:1) to provide 4-(4-fluorophenyl)-N-(1-methyl-1H-pyrazol-3-yl)pyridin-2-amine (3) as a yellow solid (1.0 g, 71%).

LCMS (ES): Found 269.1 [M+H]⁺.

NaH (60%) (37 mg, 0.93 mmol) was added portion-wise to 4-(4-fluorophenyl)-N-(1-methyl-1H-pyrazol-3-yl)pyridin-2-amine (3) (250 mg, 0.93 mmol) in DMF (10 mL) at 5° C. under Ar(g). The reaction mixture was stirred for 20 min, then methyl 4-(bromomethyl)benzoate (277 mg, 1.2 mmol) was added, and stirring was continued at 70° C. under Ar(g) for 1 h in the dark. The reaction mixture was then poured onto demineralized water (100 mL), and extracted with EtOAc (3×50 mL). The organic phases were combined, dried over Na₂SO₄, filtered and subsequently concentrated in vacuo. The resulting residue was purified by flash chromatography with EtOAc/Hexane (3:7) to furnish methyl 4-(((4-(4-fluorophenyl)pyridin-2-yl)(1-methyl-1H-pyrazol-3-yl)amino)methyl)benzoate (4) as a light yellow solid (267 mg, 68%).

LCMS (ES): Found 417.4 [M+H]⁺.

A fresh solution of NH₂OH in MeOH was prepared: [KOH (1.79 g, 32.0 mmol) in MeOH (15 mL) was added to NH₂OH.HCl (2.23 g, 32.0 mmol) in MeOH (15 mL) at 0° C.]. The reaction mixture was stirred for 20 min at 0° C., then filtered to remove salts; it was then added to methyl 4-(((4-(4-fluorophenyl)pyridin-2-yl)(1-methyl-1H-pyrazol-3-yl)amino)methyl)benzoate (4) (267 mg, 0.64 mmol) followed by KOH (359 mg, 6.41 mmol) solubilized in MeOH (10 mL). The reaction mixture was stirred at rt for 21 h, and then concentrated in vacuo, poured onto brine/H₂O (30 mL/70 mL), and extracted with CH₂Cl₂ (3×100 mL). The organic phases were combined, dried over Na₂SO₄, filtered and subsequently concentrated in vacuo. The resulting residue was purified by flash chromatography with MeOH/CH₂Cl₂ (1:9) to 4-(((4-(4-fluorophenyl)pyridin-2-yl)(1-methyl-1H-pyrazol-3-yl)amino)methyl)-N-hydroxybenzamide, Example Q, as an off white solid (30 mg, 11%).

¹H NMR (400 MHz, DMSO-d₆), $\delta_H$ ppm: 11.11 (br. s, 1H), 9.00 (br. s, 1H), 8.19 (d, J=5.3 Hz, 1H), 7.59-7.71 (m, 5H), 7.24-7.39 (m, 5H), 6.98-7.05 (m, 1H), 6.26 (d, J=2.2 Hz, 1H), 5.30 (s, 2H), 3.74-3.79 (m, 3H).

LCMS (ES): Found 418.2 [M+H]⁺.

Example R 4-(((5-Fluoropyridin-2-yl)(3-methyl-1,2,4-thiadiazol-5-yl)amino)methyl)-N-hydroxybenzamide

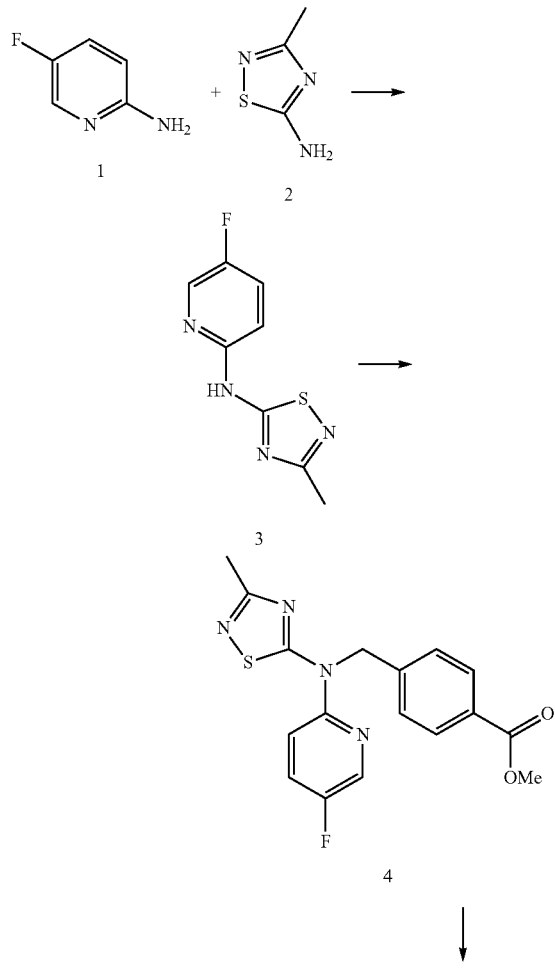

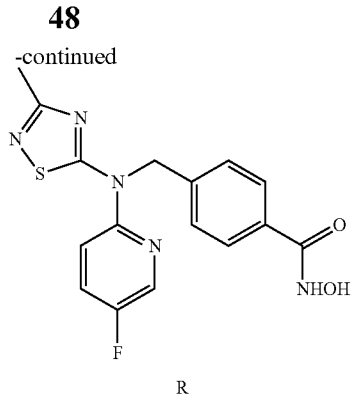

5-Fluoropyridin-2-amine (1) (1.0 g, 8.9 mmol), 5-chloro-3-methyl-1,2,4-thiadiazole (2) (1.19 g, 8.9 mmol), Xantphos (0.52 g, 0.89 mmol), and Cs₂CO₃ (4.35 g, 13.3 mmol) were combined in dry 1,4-dioxane (15 mL). The reaction mixture was degassed with N₂(g) and placed under vacuum for 10 min. Pd₂(dba)₃ (0.41 g, 0.44 mmol) was then added and the resulting reaction mixture was heated at 90° C. for 30 h. The reaction mixture was then poured onto demineralized water (200 mL), and extracted with EtOAc (3×100 mL). The organic phases were combined, dried over Na₂SO₄, filtered and subsequently concentrated in vacuo. The resulting residue was purified by flash chromatography with EtOAc/Hexane (3:7) to provide N-(5-fluoropyridin-2-yl)-3-methyl-1,2,4-thiadiazol-5-amine (3) as a yellow solid (1.2 g, 67%).

LCMS (ES): Found 211.1 [M+H]⁺.

NaH (60%) (59 mg, 1.49 mmol) was added portion-wise to N-(5-fluoropyridin-2-yl)-3-methyl-1,2,4-thiadiazol-5-amine (3) (300 mg, 1.42 mmol) in DMF (7 mL) at 5° C. under Ar(g). The reaction mixture was stirred for 20 min, then methyl 4-(bromomethyl)benzoate (425 mg, 1.85 mmol) was added, and stirring was continued at 70° C. under Ar(g) for 1 h in the dark. The reaction mixture was then poured onto water (100 mL), and extracted with EtOAc (3×50 mL). The organic phases were combined, dried over Na₂SO₄, filtered and subsequently concentrated in vacuo. The residue was purified by flash chromatography with EtOAc/Hexane (3:7) to furnish methyl-4-(((5-fluoropyridin-2-yl)(3-methyl-1,2,4-thiadiazol-5-yl)amino)methyl)benzoate (4) as a yellow solid (480 mg, 90%).

LCMS (ES): Found 359.3 [M+H]⁺.

A fresh solution of NH₂OH in MeOH was prepared: [KOH (4.63 g, 67.0 mmol) in MeOH (20 mL) was added to NH₂OH.HCl (3.76 g, 67.0 mmol) in MeOH (20 mL) at 0° C.]. The reaction mixture was stirred for 20 min at 0° C., then filtered to remove salts; it was then added to methyl 4-(((5-fluoropyridin-2-yl)(3-methyl-1,2,4-thiadiazol-5-yl)amino)methyl)benzoate (4) (480 mg, 1.3 mmol) followed by KOH (750 mg, 1.3 mmol) solubilized in MeOH (10 mL). The reaction mixture was stirred at rt for 21 h, and then concentrated in vacuo, poured onto brine/H₂O (30 mL/70 mL), and extracted with CH₂Cl₂ (3×100 mL). The organic phases were combined, dried over Na₂SO₄, filtered and subsequently concentrated in vacuo. The resulting residue was purified by flash chromatography with MeOH/CH₂Cl₂ (1:9) to provide 4-(((5-fluoropyridin-2-yl)(3-methyl-1,2,4-thiadiazol-5-yl)amino)methyl)-N-hydroxybenzamide, Example R, as an orange solid (90 mg, 19%).

¹H NMR (400 MHz, DMSO-d₆), $\delta_H$ ppm: 11.16 (br. s., 1H), 9.03 (br. s., 1H), 8.60 (d, J=2.9 Hz, 1H), 7.86 (td, J=8.7, 2.8 Hz, 1H), 7.64-7.76 (m, 2H), 7.19-7.34 (m, 3H), 5.77 (s, 2H), 2.39 (s, 3H).

LCMS (ES): Found 359.8 [M+H]⁺.

Example S 4-(((4-(4-Fluorophenyl)pyridin-2-yl)(3-methyl-1,2,4-thiadiazol-5-yl)amino)methyl)-N-hydroxybenzamide

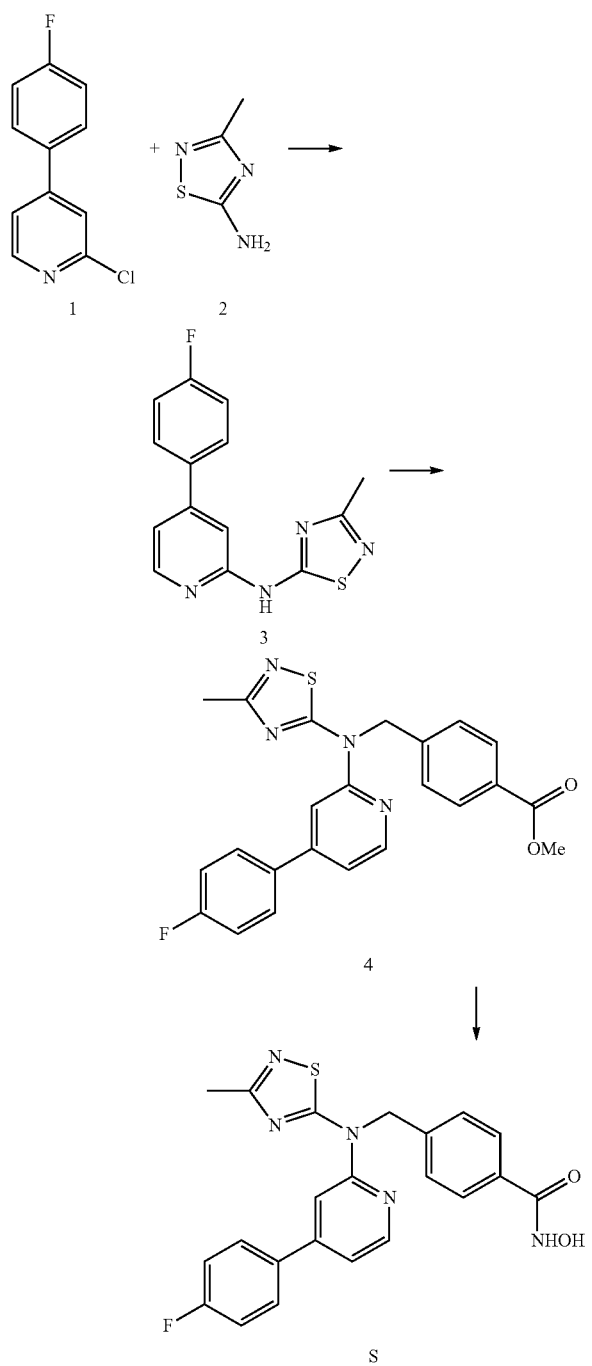

2-Chloro-4-(4-fluorophenyl)pyridine (1) (1.0 g, 4.8 mmol), 3-methyl-1,2,4-thiadiazol-5-amine (2) (0.56 g, 4.8 mmol), Xantphos (0.279 g, 0.48 mmol), and Cs$_2$CO$_3$ (2.35 g, 7.24 mmol) were combined in dry 1,4-dioxane (15 mL). The reaction mixture was degassed with N$_2$(g) and placed under vacuum for 10 min. Pd$_2$(dba)$_3$ (0.22 g, 0.24 mmol) was then added and the resulting reaction mixture was heated at 90° C. for 30 h. It was then poured onto demineralized water (200 mL), and extracted with EtOAc (3×100 mL). The organic phases were combined, dried over Na$_2$SO$_4$, filtered and subsequently concentrated in vacuo. The resulting residue was purified by flash chromatography with EtOAc/Hexane (1:1) to provide N-(4-(4-fluorophenyl)pyridin-2-yl)-3-methyl-1,2,4-thiadiazol-5-amine (3) as a yellow solid (1.1 g, 80%).

LCMS (ES): Found 287.1 [M+H]$^+$.

NaH (60%) (42 mg, 1.05 mmol) was added portion-wise to N-(4-(4-fluorophenyl)pyridin-2-yl)-3-methyl-1,2,4-thiadiazol-5-amine (3) (300 mg, 1.05 mmol) in DMF (10 mL) at 5° C. under Ar(g). The reaction mixture was stirred for 20 min, then methyl 4-(bromomethyl)benzoate (312 mg, 1.36 mmol) was added, and stirring was continued at 70° C. under Ar(g) for 1 h. The reaction mixture was then poured onto demineralized water (100 mL), and extracted with EtOAc (3×50 mL). The organic phases were combined, dried over Na$_2$SO$_4$, filtered and subsequently concentrated in vacuo. The resulting residue was purified by flash chromatography with EtOAc/Hexane (3:7) to furnish methyl 4-(((4-(4-fluorophenyl)pyridin-2-yl)(3-methyl-1,2,4-thiadiazol-5-yl)amino)methyl)benzoate (4) as a yellow solid (325 mg, 74%).

LCMS (ES): Found 421.1 [M+H]$^+$.

A fresh solution of NH$_2$OH in MeOH was prepared: [KOH (1.96 g, 35 mmol) in MeOH (10 mL) was added to NH$_2$OH.HCl (2.43 g, 35 mmol) in MeOH (10 mL) at 0° C.]. The reaction mixture was stirred for 20 min at 0° C., then filtered to remove salts; it was then added to methyl 4-(((4-(4-fluorophenyl)pyridin-2-yl)(3-methyl-1,2,4-thiadiazol-5-yl)amino)methyl)benzoate (4) (319 mg, 0.69 mmol) followed by KOH (392 mg, 7.0 mmol) solubilized in MeOH (10 mL). The reaction mixture was stirred at rt for 21 h, and then concentrated in vacuo, poured onto brine/H$_2$O (30 mL/70 mL), and extracted with CH$_2$Cl$_2$ (3×100 mL). The organic phases were combined, dried over Na$_2$SO$_4$, filtered and subsequently concentrated in vacuo. The resulting residue was purified by flash chromatography with MeOH/CH$_2$Cl$_2$ (1:9) to 4-(((4-(4-fluorophenyl)pyridin-2-yl)(3-methyl-1,2,4-thiadiazol-5-yl)amino)methyl)-N-hydroxybenzamide, Example S, as an off white solid (58 mg, 19%).

$^1$H NMR (400 MHz, DMSO-d$_6$), $\delta_H$ ppm: 11.13 (br. s., 1H), 9.02 (br. s., 1H), 8.59 (d, J=5.3 Hz, 1H), 7.82 (dd, J=8.7, 5.3 Hz, 2H), 7.67 (d, J=8.2 Hz, 2H), 7.43-7.51 (m, 2H), 7.27-7.40 (m, 4H), 5.92 (s, 2H), 2.40 (s, 3H).

LCMS (ES): Found 436.4 [M+H]$^+$.

Example T 4-(((5-Fluoropyridin-2-yl)(3-(trifluoromethyl)-1,2,4-thiadiazol-5-yl)amino)methyl)-N-hydroxybenzamide

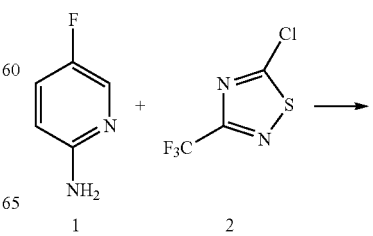

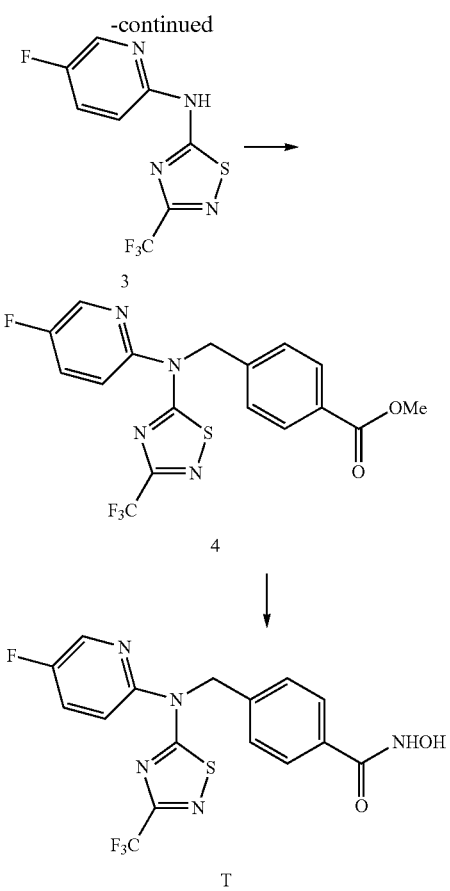

A fresh solution of NH₂OH in MeOH was prepared: [KOH (3.63 g, 64.0 mmol) in MeOH (20 mL) was added to NH₂OH.HCl (4.47 g, 64.0 mmol) in MeOH (20 mL) at 0° C.]. The reaction mixture was stirred for 20 min at 0° C., then filtered to remove salts; it was then added to methyl 4-(((5-fluoropyridin-2-yl)(3-(trifluoromethyl)-1,2,4-thiadiazol-5-yl)amino)methyl)benzoate (3) (535 mg, 1.2 mmol) followed by KOH (720 mg, 13.0 mmol) solubilized in MeOH (10 mL). The reaction mixture was stirred at rt for 21 h, and then concentrated in vacuo, poured onto brine/H₂O (30 mL/70 mL), and extracted with CH₂Cl₂ (3×100 mL). The organic phases were combined, dried over Na₂SO₄, filtered and subsequently concentrated in vacuo. The resulting residue was purified by flash chromatography with MeOH/CH₂Cl₂ (1:9) to provide 4-(((5-fluoropyridin-2-yl)(3-(trifluoromethyl)-1,2,4-thiadiazol-5-yl)amino)methyl)-N-hydroxybenzamide, Example T, as an orange solid (90 mg, 17%).

¹H NMR (400 MHz, DMSO-d₆), δ$_H$ ppm: 11.18 (br. s., 1H), 9.06 (br. s., 1H), 8.73 (d, J=2.7 Hz, 1H), 7.97 (td, J=8.6, 2.6 Hz, 1H), 7.69 (d, J=8.2 Hz, 2H), 7.46 (dd, J=9.0, 2.8 Hz, 1H), 7.31 (d, J=7.8 Hz, 2H), 5.80 (br. s., 2H), 5.72-5.87 (m, 1H).

LCMS (ES): Found 414.3 [M+H]⁺.

Example U 4-(((4-(4-Fluorophenyl)pyridin-2-yl)(pyrazin-2-yl)amino)methyl)-N-hydroxybenzamide 5-Fluoropyridin-2-amine (1) (1.0 g, 8.9 mmol), 5-chloro-3-(trifluoromethyl)-1, 2, 4-thiadiazole (2) (1.68 g, 8.9 mmol), Xantphos (0.52 g, 0.89 mmol), and Cs₂CO₃ (4.35 g, 13.3 mmol) were combined in dry 1,4-dioxane (15 mL). The reaction mixture was degassed with N₂(g) and placed under vacuum for 10 min. Pd₂(dba)₃ (0.41 g, 0.44 mmol) was then added and the resulting reaction mixture was heated at 90° C. for 30 h. It was then poured onto demineralized water (200 mL), and extracted with EtOAc (3×100 mL). The organic phases were combined, dried over Na₂SO₄, filtered and subsequently concentrated in vacuo. The resulting residue was purified by flash chromatography with EtOAc/Hexane (3:7) to provide N-(5-fluoropyridin-2-yl)-3-(trifluoromethyl)-1,2,4-thiadiazol-5-amine (3) as a yellow solid (900 mg, 38%).

LCMS (ES): Found 265.1 [M+H]⁺.

NaH (60%) (61 mg, 1.51 mmol) was added portion-wise to N-(5-fluoropyridin-2-yl)-3-(trifluoromethyl)-1,2,4-thiadiazol-5-amine (3) (400 mg, 1.51 mmol) in DMF (10 mL) at 5° C. under Ar(g). The reaction mixture was stirred for 20 min, then methyl 4-(bromomethyl)benzoate (451 mg, 1.85 mmol) was added, and stirring was continued at 70° C. under Ar(g) for 1 h in the dark. The reaction mixture was then poured onto demineralized water (100 mL), and extracted with EtOAc (3×50 mL). The organic phases were combined, dried over Na₂SO₄, filtered and subsequently concentrated in vacuo. The resulting residue was purified by flash chromatography with EtOAc/Hexane (3:7) to furnish methyl 4-(((5-fluoropyridin-2-yl)(3-(trifluoromethyl)-1,2,4-thiadiazol-5-yl)amino)methyl)benzoate (3) as a yellow solid (535 mg, 82%).

LCMS (ES): Found 413.3 [M+H]⁺.

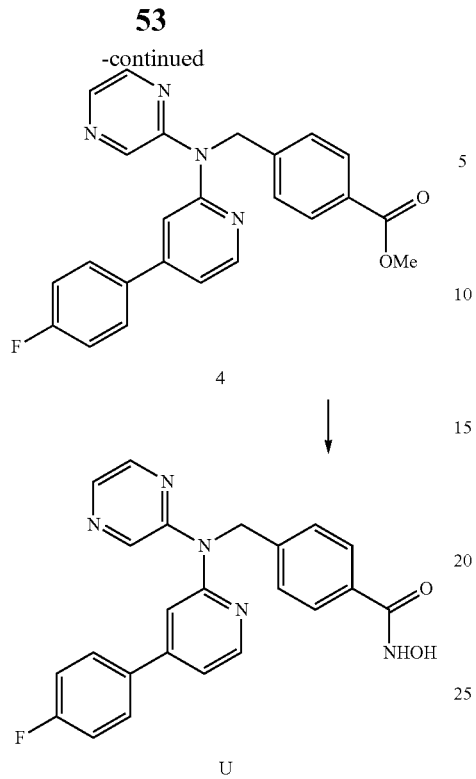

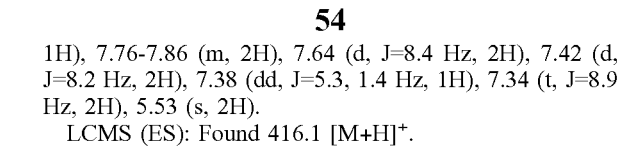

1H), 7.76-7.86 (m, 2H), 7.64 (d, J=8.4 Hz, 2H), 7.42 (d, J=8.2 Hz, 2H), 7.38 (dd, J=5.3, 1.4 Hz, 1H), 7.34 (t, J=8.9 Hz, 2H), 5.53 (s, 2H).

LCMS (ES): Found 416.1 [M+H]$^+$.

Example V 4-((Benzo[d]thiazol-2-yl(pyridin-2-yl)amino)methyl)-N-hydroxybenzamide

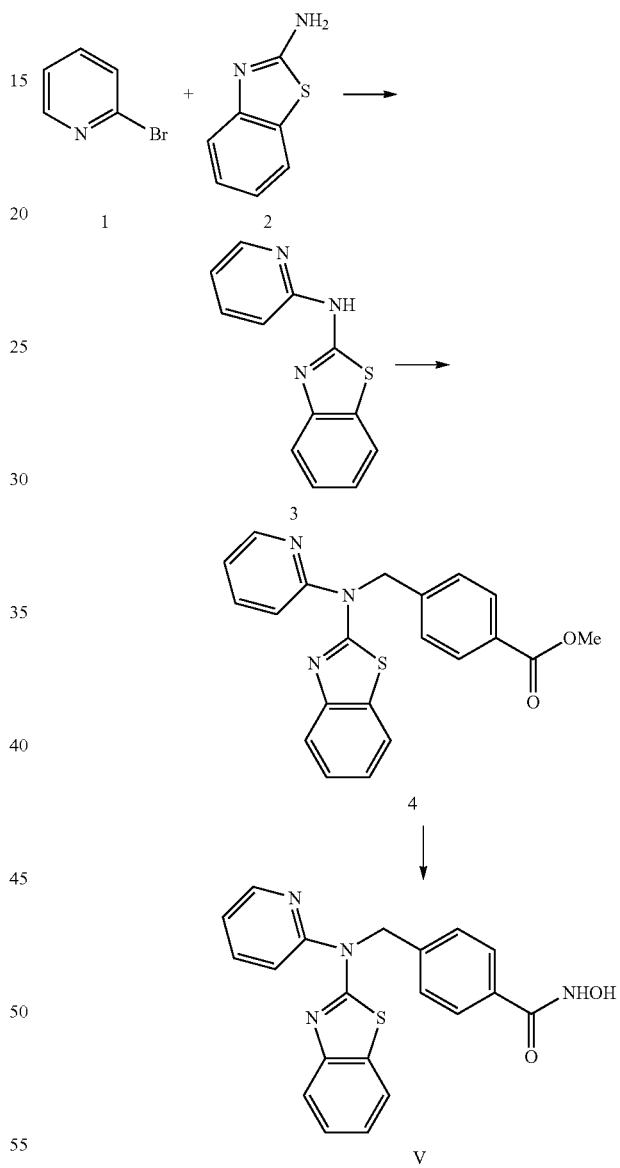

NaH (60%) (47 mg, 1.19 mmol) was added portion-wise to N-(4-(4-fluorophenyl)pyridin-2-yl)pyrazin-2-amine (3) (prepared using conditions as per Examples above) (300 mg, 1.13 mmol) in DMF (10 mL) at 5° C. under Ar(g). The reaction mixture was stirred for 20 min, then methyl 4-(bromomethyl)benzoate (337 mg, 1.47 mmol) was added, and stirring was continued at 70° C. under Ar(g) for 1 h. The reaction mixture was then poured onto demineralized water (100 mL), and extracted with EtOAc (3×50 mL). The organic phases were combined, dried over Na$_2$SO$_4$, filtered and subsequently concentrated in vacuo. The resulting residue was purified by flash chromatography with EtOAc/Hexane (3:7) to furnish methyl 4-(((4-(4-fluorophenyl)pyridin-2-yl)(pyrazin-2-yl)amino)methyl)benzoate (4) as a yellow solid (220 mg, 46%).

LCMS (ES): Found 414.4 [M+H]$^+$.

A fresh solution of NH$_2$OH in MeOH was prepared: [KOH (1.49 g, 26.9 mmol) in MeOH (10 mL) was added to NH$_2$OH.HCl (1.86 g, 26.9 mmol) in MeOH (10 mL) at 0° C.]. The reaction mixture was stirred for 20 min at 0° C., then filtered to remove salts; it was then added to methyl 4-(((4-(4-fluorophenyl)pyridin-2-yl)(pyrazin-2-yl)amino)methyl)benzoate (4) (220 mg, 0.53 mmol) followed by KOH (298 mg, 5.3 mmol) solubilized in MeOH (10 mL). The reaction mixture was stirred at rt for 21 h, and then concentrated in vacuo, poured onto brine/H$_2$O (30 mL/70 mL), and extracted with CH$_2$Cl$_2$ (3×100 mL). The organic phases were combined, dried over Na$_2$SO$_4$, filtered and subsequently concentrated in vacuo. The resulting residue was purified by flash chromatography with MeOH/CH$_2$Cl$_2$ (1:9) to 4-(((4-(4-fluorophenyl)pyridin-2-yl)(pyrazin-2-yl)amino)methyl)-N-hydroxybenzamide, Example U, as an off white solid (35 mg, 16%).

$^1$H NMR (400 MHz, DMSO-d$_6$), $\delta_H$ ppm: 11.10 (br. s., 1H), 8.99 (br. s., 1H), 8.69 (d, J=1.4 Hz, 1H), 8.36 (d, J=5.3 Hz, 1H), 8.28 (dd, J=2.7, 1.5 Hz, 1H), 8.11 (d, J=2.7 Hz, 1H), NaH (60%) (75 mg, 1.8 mmol) was added portion-wise to N-(pyridin-2-yl)benzo[d]thiazol-2-amine (3) (prepared using conditions as per Examples above) (430 mg, 1.8 mmol) in DMF (10 mL) at 5° C. under Ar(g). The reaction mixture was stirred for 20 min, then methyl 4-(bromomethyl)benzoate (563 mg, 2.4 mmol) was added, and stirring was continued at 70° C. under Ar(g) for 1 h. The reaction mixture was then poured onto demineralized water (100 mL), and extracted with EtOAc (3×50 mL). The organic phases were combined, dried over Na$_2$SO$_4$, filtered and subsequently concentrated in vacuo. The resulting residue was purified by flash chromatography with EtOAc/Hexane (3:7) to furnish methyl 4-((benzo[d]thiazol-2-yl(pyridin-2-yl)amino)methyl)benzoate (4) as a yellow solid (300 mg, 42%).

LCMS (ES): Found 376.1 [M+H]$^+$.

A fresh solution of NH$_2$OH in MeOH was prepared: [KOH (2.24 g, 40.0 mmol) in MeOH (15 mL) was added to NH$_2$OH.HCl (2.78 g, 40.0 mmol) in MeOH (15 mL) at 0° C.]. The reaction mixture was stirred for 20 min at 0° C., then filtered to remove salts; it was then added to methyl 4-((benzo[d]thiazol-2-yl(pyridin-2-yl)amino)methyl)benzoate (4) (300 mg, 0.8 mmol) followed by KOH (449 mg, 8.0 mmol) solubilized in MeOH (5 mL). The reaction mixture was stirred at rt for 21 h, and then concentrated in vacuo, poured onto brine/H$_2$O (30 mL/70 mL), and extracted with CH$_2$Cl$_2$ (3×100 mL). The organic phases were combined, dried over Na$_2$SO$_4$, filtered and subsequently concentrated in vacuo. The resulting residue was purified by flash chromatography with MeOH/CH$_2$Cl$_2$ (1:9) to provide 4-((benzo[d]thiazol-2-yl(pyridin-2-yl)amino)methyl)-N-hydroxybenzamide, Example V, as a light orange solid (60 mg, 20%).

$^1$H NMR (400 MHz, DMSO-d$_6$), δ$_H$ ppm: 11.15 (br. s, 1H), 8.99 (br. s, 1H), 8.50 (dd, J=4.8, 1.4 Hz, 1H), 7.93 (d, J=7.6 Hz, 1H), 7.78-7.86 (m, 1H), 7.68 (d, J=8.2 Hz, 2H), 7.64 (d, J=7.9 Hz, 1H), 7.33-7.39 (m, 1H), 7.21-7.31 (m, 3H), 7.11-7.20 (m, 2H), 5.82 (s, 2H).

LCMS (ES): Found 377.1 [M+H]$^+$.

Example W

N-Hydroxy-4-((pyridin-2-yl(3-(trifluoromethyl)-1,2,4-thiadiazol-5-yl)amino)methyl)benzamide

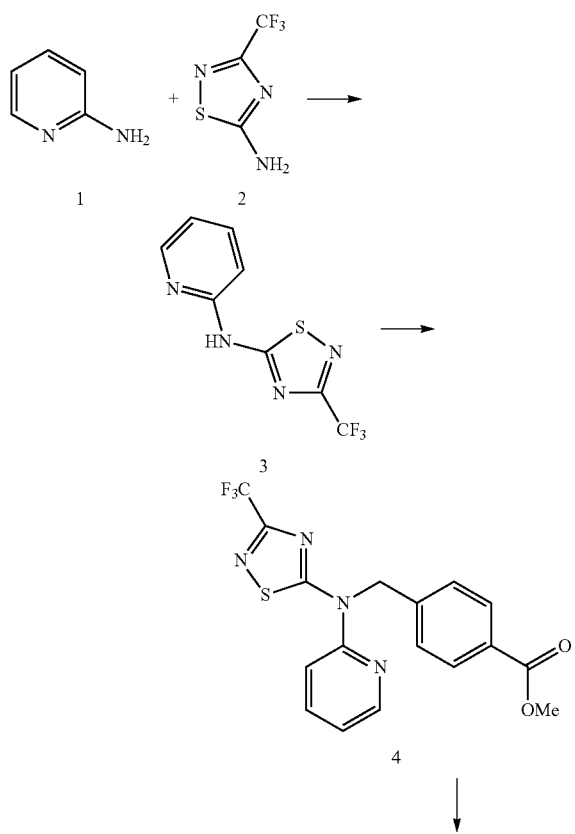

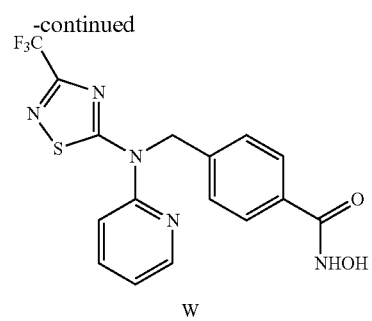

Pyridin-2-amine (1) (1.0 g, 10.6 mmol), 5-chloro-3-(trifluoromethyl)-1,2,4-thiadiazole (2) (1.82 g, 10.6 mmol), Xantphos (0.61 g, 1.06 mmol), and Cs$_2$CO$_3$ (5.18 g, 15.9 mmol) were combined in dry 1,4-dioxane (15 mL). The reaction mixture was degassed with N$_2$(g) and placed under vacuum for 10 min. Pd$_2$(dba)$_3$ (0.49 g, 0.53 mmol) was then added and the resulting reaction mixture was heated at 90° C. for 30 h. It was then poured onto demineralized water (200 mL), and extracted with EtOAc (3×100 mL). The organic phases were combined, dried over Na$_2$SO$_4$, filtered and subsequently concentrated in vacuo. The resulting residue was purified by flash chromatography with EtOAc/Hexane (1:1) to provide N-(pyridin-2-yl)-3-(trifluoromethyl)-1,2,4-thiadiazol-5-amine (3) as a yellow solid (1.4 g, 57%).

LCMS (ES): Found 247.2 [M+H]$^+$.

NaH (60%) (49 mg, 1.21 mmol) was added portion-wise to N-(pyridin-2-yl)-3-(trifluoromethyl)-1,2,4-thiadiazol-5-amine (3) (300 mg, 1.21 mmol) in DMF (10 mL) at 5° C. under Ar(g). The reaction mixture was stirred for 20 min, then methyl 4-(bromomethyl)benzoate (363 mg, 1.58 mmol) was added, and stirring was continued at 70° C. under Ar(g) for 1 h in the dark. The reaction mixture was then poured onto demineralized water (100 mL), and extracted with EtOAc (3×50 mL). The organic phases were combined, dried over Na$_2$SO$_4$, filtered and subsequently concentrated in vacuo. The resulting residue was purified by flash chromatography with EtOAc/Hexane (3:7) to furnish methyl 4-((pyridin-2-yl(3-(trifluoromethyl)-1,2,4-thiadiazol-5-yl)amino)methyl)benzoate (4) as a yellow solid (450 mg, 90%).

LCMS (ES): Found 395.3 [M+H]$^+$.

A fresh solution of NH$_2$OH in MeOH was prepared: [KOH (3.56 g, 63.4 mmol) in MeOH (20 mL) was added to NH$_2$OH.HCl (4.41 g, 63.4 mmol) in MeOH (20 mL) at 0° C.]. The reaction mixture was stirred for 20 min at 0° C., then filtered to remove salts; it was then added to methyl 4-((pyridin-2-yl(3-(trifluoromethyl)-1,2,4-thiadiazol-5-yl)amino)methyl)benzoate (4) (500 mg, 1.2 mmol) followed by KOH (712 mg, 12.6 mmol) solubilized in MeOH (10 mL). The reaction mixture was stirred at rt for 21 h, and then concentrated in vacuo, poured onto brine/H$_2$O (30 mL/70 mL), and extracted with CH$_2$Cl$_2$ (3×100 mL). The organic phases were combined, dried over Na$_2$SO$_4$, filtered and subsequently concentrated in vacuo. The resulting residue was purified by flash chromatography with MeOH/CH$_2$Cl$_2$ (1:9) to provide N-hydroxy-4-((pyridin-2-yl(3-(trifluoromethyl)-1,2,4-thiadiazol-5-yl)amino)methyl)benzamide, Example W, as an off white solid (20 mg, 4%).

$^1$H NMR (400 MHz, DMSO-d$_6$), δ$_H$ ppm: 11.15 (br. s., 1H), 9.03 (br. s., 1H), 8.63-8.68 (m, J=5.0, 0.9 Hz, 1H), 7.97 (ddd, J=8.7, 7.2, 1.8 Hz, 1H), 7.69 (d, J=8.4 Hz, 2H), 7.41 (d, J=8.6 Hz, 1H), 7.32 (d, J=8.3 Hz, 2H), 7.28 (dd, J=7.0, 5.3 Hz, 1H), 5.80 (s, 2H).

LCMS (ES): Found 396.3 [M+H]$^+$.

Example X

N-Hydroxy-4-(((3-methoxypyridin-2-yl)-(5-methyl-pyridin-2-yl)amino)methyl)benzamide

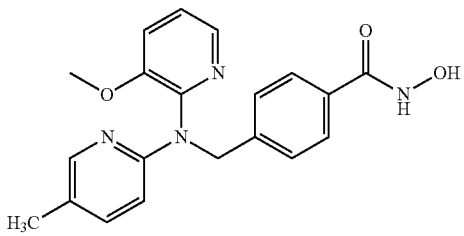 [SMILES: COc1cccnc1N(Cc1ccc(C(=O)NO)cc1)c1ccc(C)cn1]

$^1$H NMR (400 MHz, Methanol-d$_4$), δ$_H$ ppm: 7.97 (d, J=4.9 Hz, 1H), 7.89 (d, J=2.3 Hz, 1H), 7.61 (d, J=7.8 Hz, 2H), 7.46 (t, J=7.5 Hz, 3H), 7.33 (dd, J=8.5, 2.4 Hz, 1H), 7.22 (dd, J=8.2, 4.8 Hz, 1H), 6.41 (d, J=8.5 Hz, 1H), 5.31 (s, 2H), 3.73 (s, 3H), 2.20 (s, 3H).

LCMS (ES): Found 365.0 [M+H]$^+$.

Example Y

N-Hydroxy-4-(((5-methoxypyridin-2-yl)(5-methyl-pyridin-2-yl)amino)methyl)benzamide

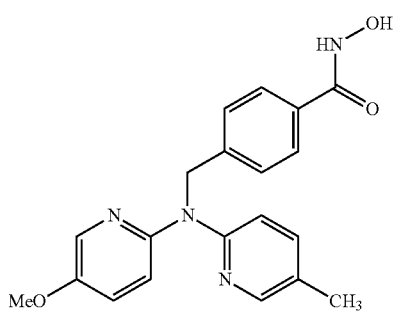 [SMILES: COc1ccc(N(Cc2ccc(C(=O)NO)cc2)c2ccc(C)cn2)nc1]

$^1$H NMR (400 MHz, Methanol-d$_4$), δ$_H$ ppm: 7.99 (dd, J=4.8, 2.6 Hz, 2H), 7.62 (d, J=8.0 Hz, 2H), 7.41 (dd, J=8.2, 4.9 Hz, 3H), 7.31 (dd, J=9.1, 3.1 Hz, 1H), 7.14 (d, J=8.9 Hz, 1H), 6.84 (d, J=8.5 Hz, 1H), 5.36 (s, 2H), 3.83 (s, 3H), 2.22 (s, 3H).

LCMS (ES): Found 365.0 [M+H]$^+$.

Example Z

N-Hydroxy-4-(((3-methoxypyridin-2-yl)(5-morpholinopyridin-2-yl)amino)methyl)benzamide

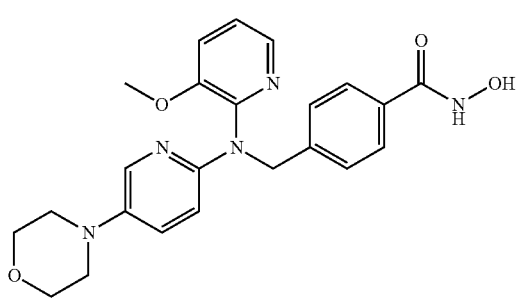 [SMILES: COc1cccnc1N(Cc1ccc(C(=O)NO)cc1)c1ccc(N2CCOCC2)cn1]

$^1$H NMR (400 MHz, Methanol-d$_4$), δ$_H$ ppm: 7.94 (dd, J=4.8, 1.5 Hz, 1H), 7.78 (d, J=3.0 Hz, 1H), 7.61 (d, J=8.3 Hz, 2H), 7.38-7.51 (m, 3H), 7.27 (dd, J=9.0, 3.1 Hz, 1H), 7.17 (dd, J=8.1, 4.8 Hz, 1H), 6.51 (d, J=9.0 Hz, 1H), 5.31 (s, 2H), 3.77-3.89 (m, 4H), 3.72 (s, 3H), 2.97-3.08 (m, 4H).

LCMS (ES): Found 436.0 [M+H]$^+$.

Example AA

N-Hydroxy-4-(((5-methoxypyridin-2-yl)(5-morpholinopyridin-2-yl)amino)methyl)benzamide

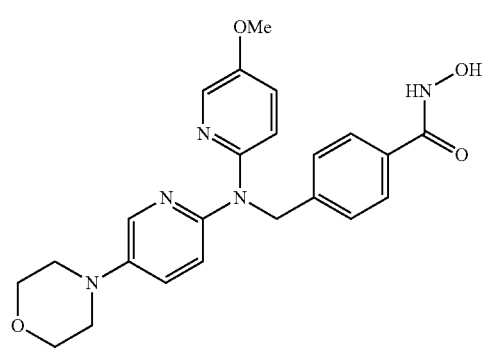 [SMILES: COc1ccc(N(Cc2ccc(C(=O)NO)cc2)c2ccc(N3CCOCC3)cn2)nc1]

$^1$H NMR (400 MHz, Methanol-d$_4$), δ$_H$ ppm: 7.88-7.95 (m, 2H), 7.58-7.66 (m, 2H), 7.42 (d, J=8.0 Hz, 2H), 7.33 (dd, J=9.0, 3.1 Hz, 1H), 7.26 (dd, J=9.1, 3.1 Hz, 1H), 6.99 (dd, J=9.0, 4.5 Hz, 2H), 5.34 (s, 2H), 3.71-3.94 (m, 7H), 3.04-3.15 (m, 4H).

LCMS (ES): Found 436.0 [M+H]$^+$.

Example BB

N-Hydroxy-4-((pyridin-2-yl(thieno[3,2-c]pyridin-4-yl)amino)methyl)benzamide

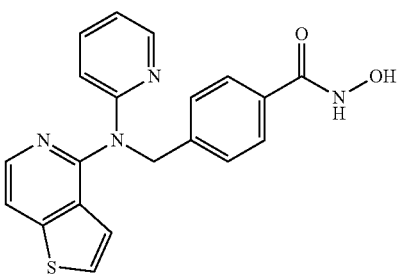 [SMILES: O=C(NO)c1ccc(CN(c2ccccn2)c2nccc3sccc23)cc1]

$^1$H NMR (400 MHz, Methanol-d$_4$), δ$_H$ ppm: 7.97-8.10 (m, 1H), 7.76 (dd, J=9.3, 7.1 Hz, 3H), 7.33-7.69 (m, 5H), 7.14 (d, J=5.4 Hz, 1H), 6.98 (d, J=9.1 Hz, 1H), 6.64 (t, J=6.8 Hz, 1H), 5.56 (s, 2H).

LCMS (ES): Found 377.0 [M+H]$^+$.

Example CC

N-Hydroxy-4-(((6-methylpyridin-2-yl)(5-morpholinopyridin-2-yl)amino)methyl)benzamide

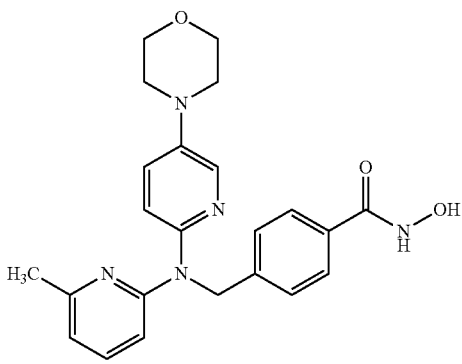 [SMILES: Cc1cccc(N(Cc2ccc(C(=O)NO)cc2)c2ccc(N3CCOCC3)cn2)n1]

¹H NMR (400 MHz, Methanol-d₄), δ_H ppm: 7.99 (d, J=3.0 Hz, 1H), 7.62 (d, J=7.8 Hz, 2H), 7.42 (d, J=8.1 Hz, 2H), 7.34-7.39 (m, 2H), 7.14 (d, J=8.9 Hz, 1H), 6.64 (dd, J=8.1, 7.8 Hz, 2H), 5.39 (s, 2H), 3.79-3.86 (m, 4H), 3.14 (dd, J=6.1, 3.6 Hz, 4H), 2.37 (s, 3H).

LCMS (ES): Found 420.0 [M+H]⁺.

Example DD

N-Hydroxy-4-{[(pyrazin-2-yl)(pyrimidin-4-yl)amino]methyl}benzamide

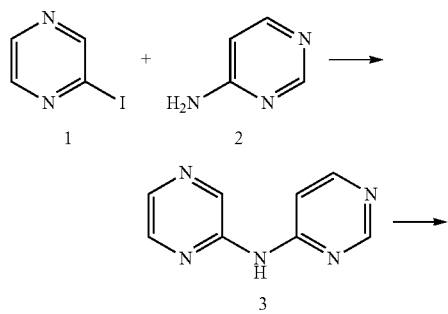

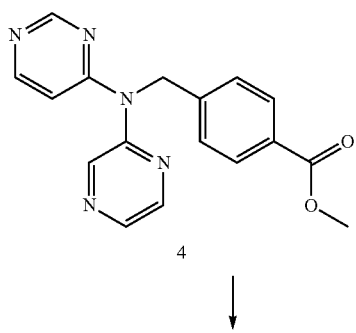

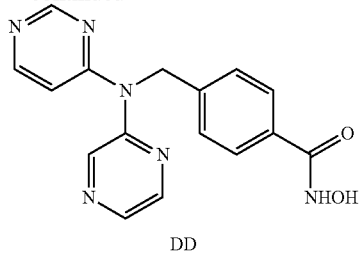

A solution of 2-iodopyrazine (1) (1.2 g, 5.83 mmol), pyrimidin-4-amine (2) (609 mg, 6.41 mmol), Cs₂CO₃ (3.80 g, 11.65 mmol) and Xantphos (148 mg, 0.26 mmol) in 1,4-Dioxane (15 mL) was purged with N₂(g) for 10 min. Pd₂(dba)₃ (107 mg, 0.12 mmol) was added and mixture was heated to 90° C. for 3 h. Reaction was cooled to rt and partitioned between water (300 mL) and EtOAc (3×100 mL). Combined organics were washed with water (50 mL), dried over Na₂SO₄, filtered and concentrated in vacuo. The residue was purified by flash column chromatography with CH₂Cl₂/MeOH (1:0-9:1) to yield (3) (678 mg, 66%).

¹H NMR (500 MHz, Methanol-d₄), δ_H ppm: 9.06 (d, J=1.3 Hz, 1H), 8.74 (s, 1H), 8.42 (d, J=6.0 Hz, 1H), 8.34 (dd, J=2.6, 1.5 Hz, 1H), 8.19 (d, J=2.7 Hz, 1H), 7.72 (dd, J=6.0, 1.0 Hz, 1H).

LCMS (ES): Found 174.0 [M+H]⁺.

NaH (60%, 48.5 mg, 1.21 mmol) was added to a solution of (3) (200 mg, 1.15 mmol) in DMF (7 mL) at 5° C. under N₂(g). The reaction mixture was stirred for 20 min then methyl 4-(bromomethyl)benzoate (344 mg, 1.5 mmol) was added as a solution in DMF (3 mL), the stirring was continued at 70° C. for 1 h. Reaction cooled to rt and poured onto water (100 mL). Brine (25 mL) was added and the aqueous was extracted with EtOAc (2×100 mL). Combined organics were dried over Na₂SO₄, filtered and concentrated in vacuo. Purification by flash column chromatography with CH₂Cl₂/EtOAc (1:0-0:1) then EtOAc/MeOH (1:0-4:1) yielded (4) (187 mg, 50%).

¹H NMR (500 MHz, Chloroform-d), δ_H ppm: 8.85 (d, J=1.4 Hz, 1H), 8.77-8.80 (m, 1H), 8.34-8.38 (m, 2H), 8.29 (d, J=2.6 Hz, 1H), 7.95 (d, J=8.4 Hz, 2H), 7.36 (d, J=8.4 Hz, 2H), 6.91 (dd, J=6.0, 1.2 Hz, 1H), 5.49 (s, 2H), 3.87 (s, 3H).

LCMS (ES): Found 322.0 [M+H]⁺.

A solution of (4) (0.09 mL, 0.58 mmol) in 0.85M hydroxylamine in MeOH (10 mL) was stirred at rt for 40 h. Solvent was removed in vacuo and the residue purified by reverse phase HPLC to give Example DD (30 mg, 15%).

¹H NMR (500 MHz, Methanol-d₄), δ_H ppm: 8.89 (d, J=1.4 Hz, 1H), 8.69 (s, 1H), 8.47 (dd, J=2.5, 1.5 Hz, 1H), 8.25-8.37 (m, 2H), 7.68 (d, J=8.3 Hz, 2H), 7.38 (d, J=8.3 Hz, 2H), 7.08 (dd, J=6.2, 1.2 Hz, 1H), 5.51 (s, 2H).

LCMS (ES): Found 323.0 [M+H]⁺.

Example EE

3-Fluoro-N-hydroxy-4-{[(pyrazin-2-yl)(pyrimidin-4-yl)amino]methyl}benzamide

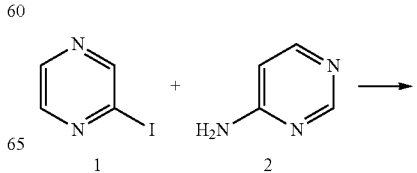

Example FF

N-Hydroxy-6-{[(pyrazin-2-yl)(pyrimidin-4-yl)amino]methyl}pyridine-3-carboxamide

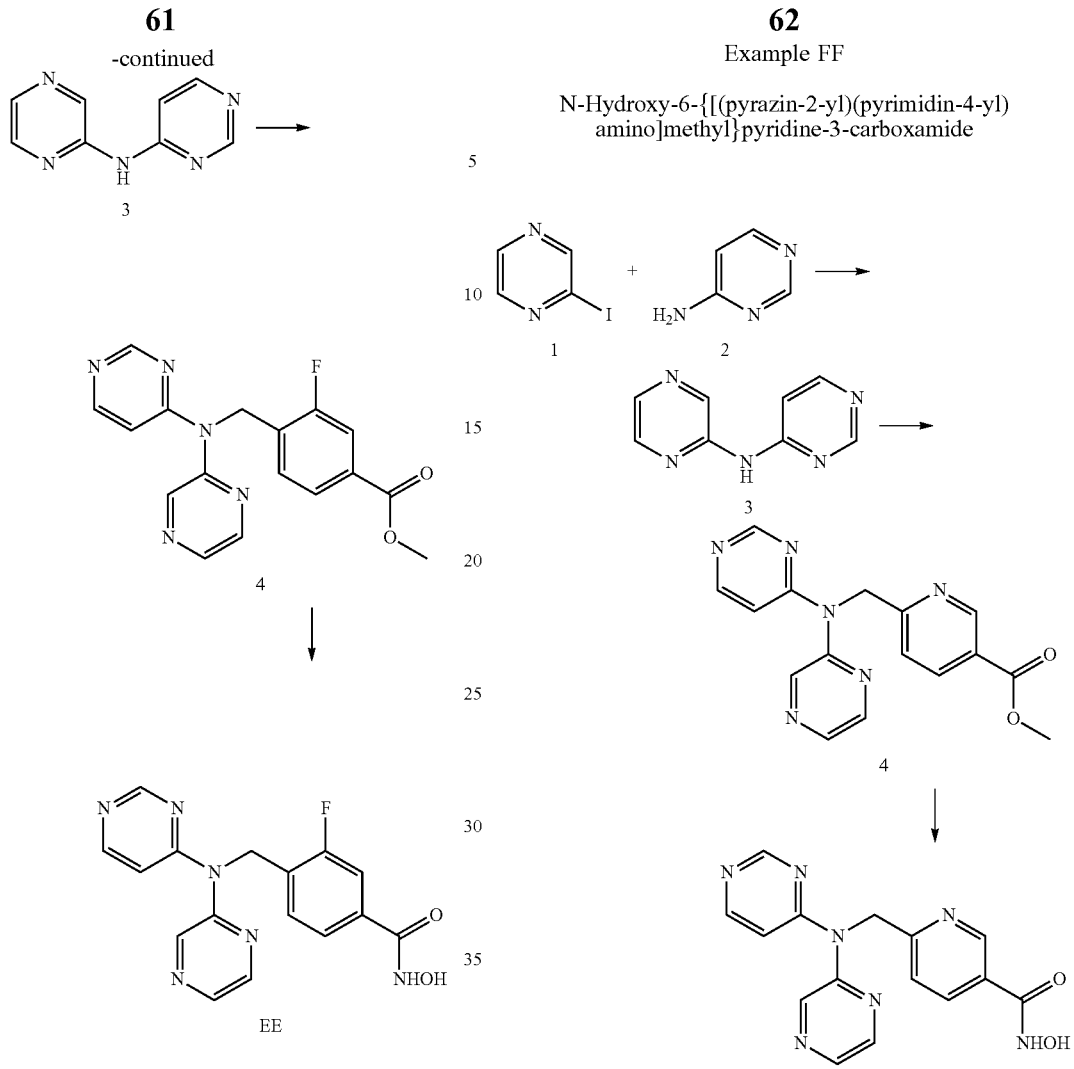

NaH (60%, 48.5 mg, 1.21 mmol) was added to a solution of (3) (200 mg, 1.15 mmol) in DMF (7 mL) at 5° C. under N₂(g). The reaction mixture was stirred for 20 min then methyl 4-(bromomethyl)-3-fluorobenzoate (371 mg, 1.5 mmol) was added as a solution in DMF (3 mL). The stirring was continued at 70° C. for 1 h. Reaction cooled to rt and poured onto water (100 mL). Brine (25 mL) was added and the aqueous was extracted with EtOAc (2×100 mL). Combined organics were dried over Na₂SO₄, filtered and concentrated in vacuo. Purification by flash column chromatography with EtOAc/CH₂Cl₂ (0:1-1:0) then EtOAc/MeOH (1:0-4:1) yielded (4) (158 mg, 40%).

¹H NMR (500 MHz, Chloroform-d), δ$_H$ ppm: 8.87 (d, J=1.4 Hz, 1H), 8.76-8.78 (m, 1H), 8.36-8.40 (m, 2H), 8.31 (d, J=2.6 Hz, 1H), 7.69 (d, J=9.2 Hz, 2H), 7.30 (t, J=7.6 Hz, 1H), 6.92 (dd, J=6.1, 1.2 Hz, 1H), 5.50 (s, 2H), 3.87 (s, 3H).

LCMS (ES): Found 340.0 [M+H]⁺.

A solution of (4) (0.08 mL, 0.47 mmol) in 0.85M hydroxylamine in MeOH (10 mL) was stirred at rt for 18 h. Solvent was concentrated to dryness and the residue purified by neutral pH reverse phase HPLC to give Example EE (25 mg, 15%).

¹H NMR (500 MHz, Methanol-d₄), δ$_H$ ppm: 8.91 (d, J=1.4 Hz, 1H), 8.70 (s, 1H), 8.48 (dd, J=2.5, 1.5 Hz, 1H), 8.31-8.38 (m, 2H), 7.43-7.50 (m, 2H), 7.35 (t, J=7.9 Hz, 1H), 7.09 (dd, J=6.2, 1.2 Hz, 1H), 5.53 (s, 2H).

LCMS (ES): Found 341.0 [M+H]⁺.

NaH (60%, 48.5 mg, 1.21 mmol) was added to a solution of (3) (200 mg, 1.15 mmol) in DMF (7 mL) at 5° C. under N₂(g). The reaction mixture was stirred for 20 min then methyl 6-(bromomethyl)pyridine-3-carboxylate (345 mg, 1.5 mmol) was added as a solution in DMF (3 mL). The stirring was continued at 70° C. for 1 h. Reaction cooled to rt and poured onto water (100 mL). Brine (25 mL) was added and the aqueous was extracted with EtOAc (2×100 mL). Combined organics were dried over Na₂SO₄, filtered and concentrated in vacuo. The residue was purified by flash column chromatography with CH₂Cl₂/EtOAc (1:0-0:1) then CH₂Cl₂/MeOH (1:0-4:1) to yield (4) (116 mg, 27%).

¹H NMR (500 MHz, Chloroform-d), δ$_H$ ppm: 9.11 (d, J=1.6 Hz, 1H), 8.97 (d, J=1.4 Hz, 1H), 8.70-8.77 (m, 1H), 8.34-8.40 (m, 2H), 8.31 (d, J=2.6 Hz, 1H), 8.18 (dd, J=8.2, 2.1 Hz, 1H), 7.36 (d, J=8.2 Hz, 1H), 7.01 (dd, J=6.1, 1.2 Hz, 1H), 5.56 (s, 2H), 3.90 (s, 3H).

LCMS (ES): Found 322.9 [M+H]⁺.

A solution of (4) (0.06 mL, 0.31 mmol) in 0.85M hydroxylamine in MeOH (10 mL) was stirred at rt for 18 h. The reaction mixture was concentrated to dryness. The residue was purified by reverse phase HPLC to give Example FF (25.7 mg, 26%).

¹H NMR (500 MHz, DMSO-d₆), δ$_H$ ppm: 8.99 (d, J=4.9 Hz, 1H), 8.64-8.76 (m, 1H), 8.32-8.51 (m, 3H), 7.82-7.93 (m, 1H), 7.03-7.30 (m, 2H), 5.45 (m, 2H).

LCMS (ES): Found 324.1 [M+H]⁺.

Example GG

4-{[Bis(pyrazin-2-yl)amino]methyl}-N-hydroxybenzamide

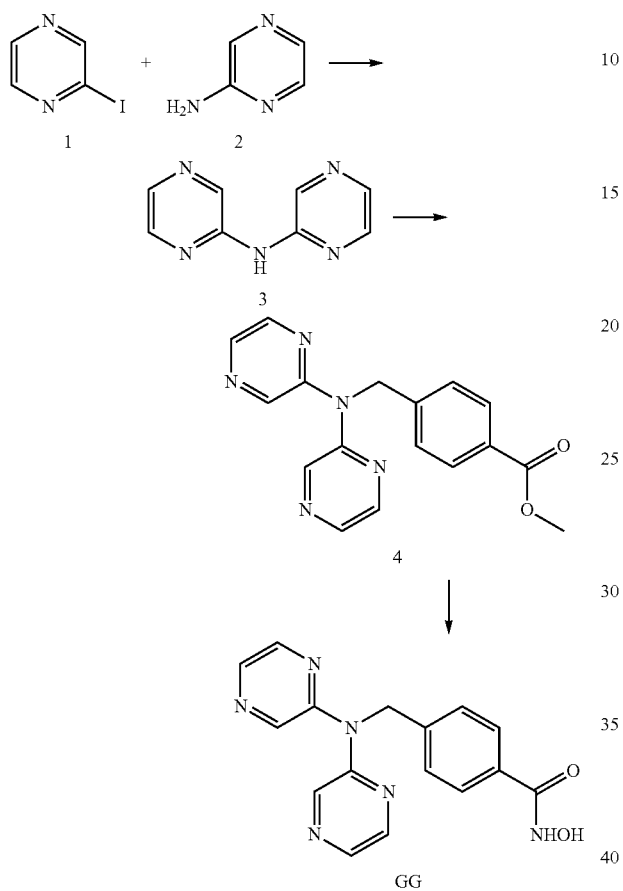

A solution of 2-iodopyrazine (1) (1.2 g, 5.83 mmol), pyrazin-2-amine (2) (609 mg, 6.4 mmol), $Cs_2CO_3$ (3.80 g, 11.7 mmol) and Xantphos (148 mg, 0.26 mmol) in dioxane (25 mL) was purged with $N_2(g)$ for 10 min. $Pd_2(dba)_3$ (107 mg, 0.12 mmol) was added and mixture was heated to 90° C. for 3 h. Reaction cooled to rt and poured onto water (200 mL), extracted with EtOAc (2×150 mL) and $CH_2Cl_2$-IPA (150 mL, 4:1). Combined organics were dried over $Na_2SO_4$, filtered and concentrated in vacuo. Flash column chromatography with heptane/EtOAc (4:1-0:1) then EtOAc/MeOH (1:0-3:1) yielded (3) as an off white solid (210 mg, 51%).

$^1$H NMR (500 MHz, Chloroform-d), $\delta_H$ ppm: 8.99 (d, J=1.4 Hz, 2H), 8.30 (dd, J=2.6, 1.5 Hz, 2H), 8.11 (d, J=2.7 Hz, 2H).

LCMS (ES): Found 174.1 [M+H]$^+$.

NaH (60%, 48.5 mg, 1.21 mmol) was added to a solution of (3) (200 mg, 1.15 mmol) in DMF (7 mL) at 5° C. under $N_2(g)$. The reaction mixture was stirred for 20 min then methyl 4-(bromomethyl)benzoate (344 mg, 1.5 mmol) was added as a solution in DMF (3 mL). The stirring was continued at 70° C. for 1 h. Reaction cooled to rt and poured onto water (100 mL). Brine (25 mL) was added and extracted with EtOAc (2×100 mL). Combined organic was dried over $Na_2SO_4$, filtered and concentrated in vacuo. The residue was purified by flash column chromatography with $CH_2Cl_2$/EtOAc (1:0-0:1) then EtOAc/MeOH (1:0-4:1) to give (4) (196 mg, 53%).

$^1$H NMR (500 MHz, Chloroform-d), $\delta_H$ ppm: 8.59-8.65 (m, 2H), 8.23-8.26 (m, 2H), 8.16 (d, J=2.5 Hz, 2H), 7.94 (d, J=8.3 Hz, 2H), 7.38 (d, J=8.2 Hz, 2H), 5.50 (s, 2H), 3.86 (s, 3H).

LCMS (ES): Found 321.9 [M+H]$^+$.

A solution of (4) (0.09 mL, 0.61 mmol) in 0.85M hydroxylamine in MeOH (10 mL) was stirred at rt for 72 h. Solvent concentrated to dryness and the residue purified by reverse phase HPLC to give Example GG (23 mg, 12%).

$^1$H NMR (500 MHz, Methanol-$d_4$), $\delta_H$ ppm: 8.66 (d, J=1.3 Hz, 2H), 8.28-8.36 (m, 2H), 8.16 (d, J=2.6 Hz, 2H), 7.67 (d, J=8.2 Hz, 2H), 7.45 (d, J=8.2 Hz, 2H), 5.56 (s, 2H).

LCMS (ES): Found 323.1 [M+H]$^+$.

Example HH

4-{[Bis(pyrazin-2-yl)amino]methyl}-3-fluoro-N-hydroxybenzamide

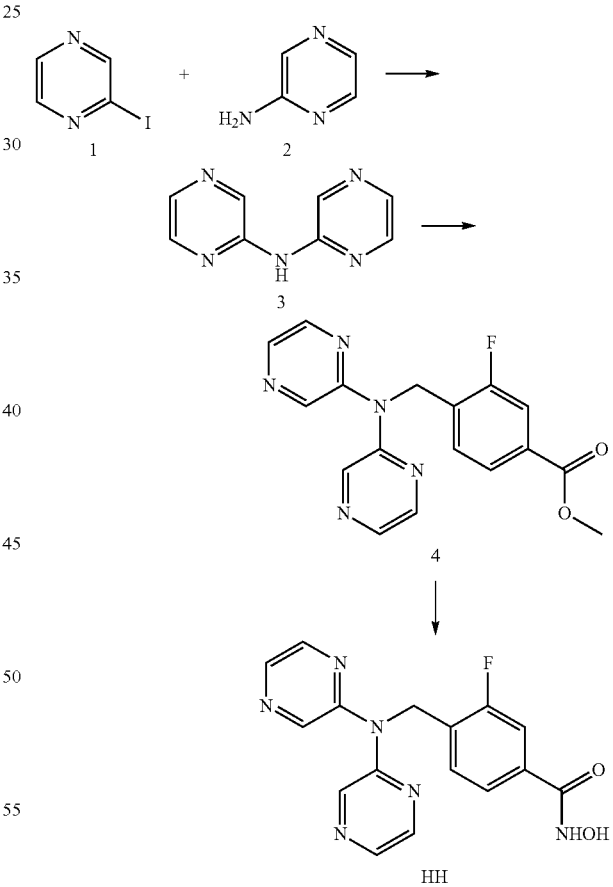

NaH (60%, 49 mg, 1.21 mmol) was added to a solution of (3) (200 mg, 1.15 mmol) in DMF (7 mL) at 5° C. under $N_2(g)$. The reaction mixture was stirred for 20 min then methyl 4-(bromomethyl)-3-fluorobenzoate (371 mg, 1.5 mmol) was added as a solution in DMF (3 mL). The stirring was continued at 70° C. for 1 h. Reaction cooled to rt and poured onto water (100 mL). Brine (25 mL) was added and the aqueous was extracted with EtOAc (2×100 mL). Combined organics were dried over Na$_2$SO$_4$, filtered and concentrated in vacuo. Purification by flash column chromatography with CH$_2$Cl$_2$/EtOAc (1:0-0:1) then EtOAc/MeOH (1:0-4:1) yielded (4) (195 mg, 50%).

$^1$H NMR (500 MHz, Chloroform-d), δ$_H$ ppm: 8.65 (d, J=1.4 Hz, 2H), 8.25 (dd, J=2.5, 1.5 Hz, 2H), 8.18 (d, J=2.6 Hz, 2H), 7.65-7.72 (m, 2H), 7.31 (t, J=7.8 Hz, 1H), 5.53 (s, 2H), 3.87 (s, 3H).

LCMS (ES): Found 339.9 [M+H]$^+$.

A solution of (4) (0.09 mL, 0.57 mmol) in 0.85M hydroxylamine in MeOH (10 mL) was stirred at rt for 18 h. Solvent was concentrated in vacuo and the residue purified by reverse phase HPLC to give Example HH (81 mg, 41%).

$^1$H NMR (500 MHz, DMSO-d$_6$), δ$_H$ ppm: 8.76 (d, J=1.4 Hz, 2H), 8.34 (dd, J=2.5, 1.5 Hz, 2H), 8.25 (d, J=2.6 Hz, 2H), 7.51 (dd, J=11.1, 1.3 Hz, 1H), 7.45 (dd, J=8.0, 1.4 Hz, 1H), 7.34 (t, J=7.8 Hz, 1H), 5.50 (s, 2H).

LCMS (ES): Found 341.1 [M+H]$^+$.

Example II

6-{[Bis(pyrazin-2-yl)amino]methyl}-N-hydroxypyridine-3-carboxamide added and the aqueous was extracted with EtOAc (2×100 mL). Combined organics were dried over Na$_2$SO$_4$, filtered and concentrated in vacuo. The residue was purified by flash column chromatography with CH$_2$Cl$_2$/EtOAc (1:0-0:1) then EtOAc/MeOH (1:0-4:1) to give (4) (129 mg, 35%).

$^1$H NMR (500 MHz, Chloroform-d), δ$_H$ ppm: 9.04-9.13 (m, 1H), 8.70 (s, 2H), 8.19 (s, 2H), 8.13 (dd, J=5.6, 2.3 Hz, 3H), 7.32 (d, J=8.2 Hz, 1H), 5.55 (s, 2H), 3.86 (s, 3H).

LCMS (ES): Found 322.9 [M+H]$^+$.

A solution of (4) (0.06 mL, 0.4 mmol) in 0.85M hydroxylamine in MeOH (10 mL) was stirred at rt for 18 h. The solvent was concentrated to dryness and the residue purified by reverse phase HPLC to give Example II (37 mg, 28%).

$^1$H NMR (500 MHz, DMSO-d$_6$), δ$_H$ ppm: 8.75 (d, J=1.3 Hz, 3H), 8.31 (dd, J=2.6, 1.5 Hz, 2H), 8.21 (d, J=2.6 Hz, 2H), 7.89 (dd, J=8.1, 2.0 Hz, 1H), 7.18 (d, J=8.1 Hz, 1H), 5.47 (s, 2H).

LCMS (ES): Found 324.1 [M+H]$^+$.

Example JJ

N-Hydroxy-4-{[(3-methoxypyridin-2-yl)(pyrazin-2-yl)amino]methyl}benzamide

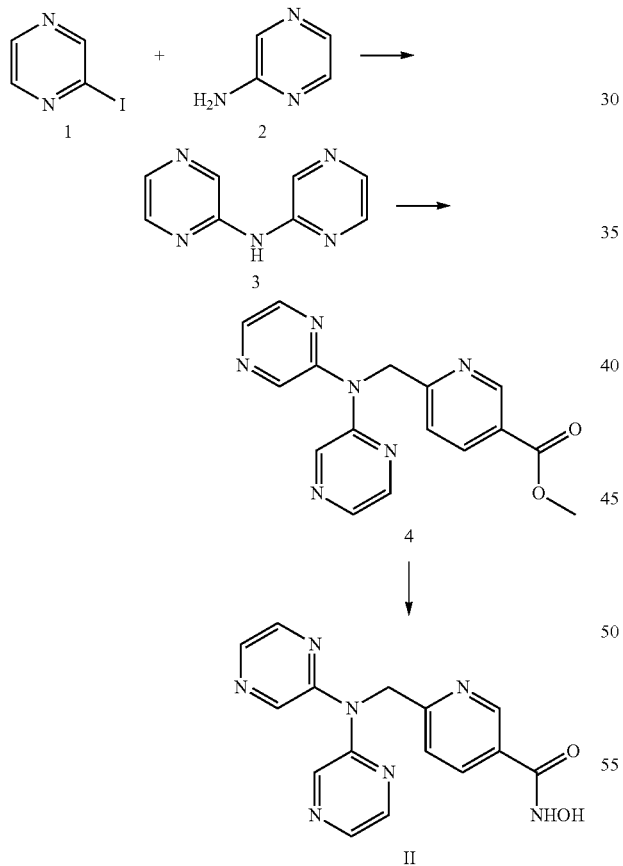

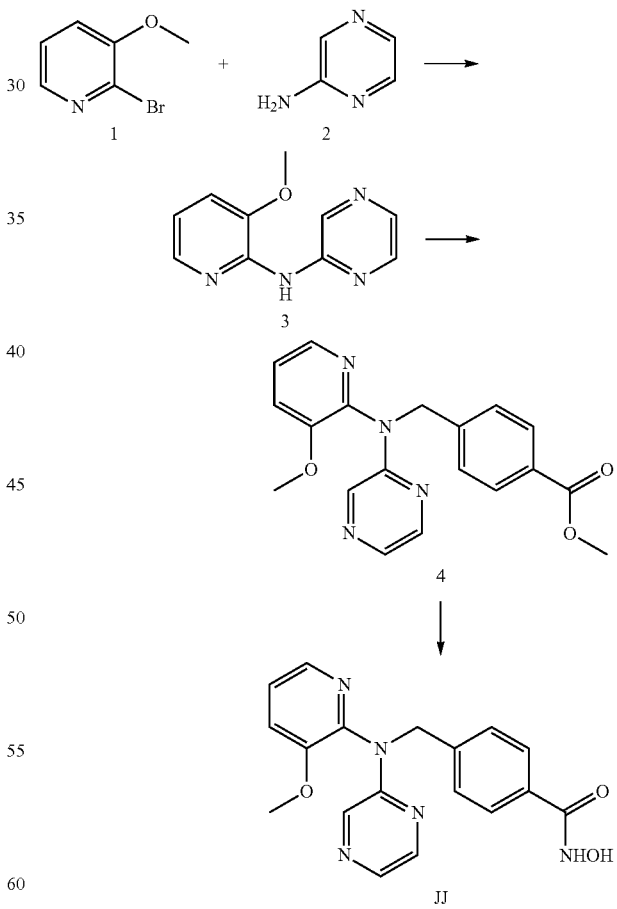

NaH (60%, 48.5 mg, 1.21 mmol) was added to a solution of (3) (200 mg, 1.15 mmol) in DMF (7 mL) at 5° C. under N$_2$(g). The reaction mixture was stirred for 20 min then methyl 6-(bromomethyl)pyridine-3-carboxylate (345 mg, 1.5 mmol) was added as a solution in DMF (3 mL). The stirring was continued at 70° C. for 1 h. Reaction cooled to rt and poured onto water (100 mL). Brine (25 mL) was A solution of pyrazin-2-amine (2) (557 mg, 5.85 mmol), 2-bromo-3-methoxypyridine (1) (1.0 g, 5.32 mmol), Cs$_2$CO$_3$ (3.47 g, 10.64 mmol) and Xantphos (135 mg, 0.23 mmol) in dioxane (15 mL) was purged with N$_2$(g) for 10 min. Pd$_2$(dba)$_3$ (97.4 mg, 0.11 mmol) was added and the mixture was heated to 90° C. for 3 h. The reaction was cooled to rt, partitioned between water (200 mL) and EtOAc (200 mL). Phases were separated and aqueous layer was washed with EtOAc (200+100+50 mL). Combined organics were dried over Na₂SO₄, filtered and concentrated in vacuo. The residue was purified by flash column chromatography eluted with a gradient of CH₂Cl₂/EtOAc (1:0-0:1) to yield (3) (1.0 g, 88%).

¹H NMR (500 MHz, Chloroform-d), $\delta_H$ ppm: 9.91 (d, J=1.2 Hz, 1H), 8.11-8.20 (m, 2H), 7.91 (dd, J=5.0, 1.4 Hz, 1H), 7.80 (s, 1H), 7.06 (dd, J=7.9, 1.3 Hz, 1H), 6.85 (dd, J=7.9, 5.0 Hz, 1H), 3.92 (s, 3H).

LCMS (ES): Found 203.2 [M+H]⁺.

NaH (60%, 41.5 mg, 1.04 mmol) was added to a solution of (3) (200 mg, 0.99 mmol) in DMF (10 mL) at 5° C. under N₂(g). The reaction mixture was stirred for 20 min then methyl 4-(bromomethyl)benzoate (294 mg, 1.29 mmol) was added. The stirring was continued at 70° C. under N₂(g) for 1 h. The reaction was cooled to rt and poured onto water (150 mL) and brine (50 mL), the aqueous was extracted with EtOAc (3×100 mL). Combined organics were dried over Na₂SO₄, filtered and concentrated in vacuo. The residue was purified by flash column chromatography with CH₂Cl₂/EtOAc (1:0-0:1) then EtOAc/MeOH (1:0-4:1) to yield (4) (251 mg, 73%).

¹H NMR (500 MHz, Chloroform-d), $\delta_H$ ppm: 8.06-8.10 (m, 2H), 7.87-7.92 (m, 3H), 7.78 (d, J=1.5 Hz, 1H), 7.44 (d, J=8.4 Hz, 2H), 7.23 (dd, J=8.2, 1.4 Hz, 1H), 7.15 (dd, J=8.1, 4.7 Hz, 1H), 5.42 (s, 2H), 3.85 (s, 3H), 3.73 (s, 3H).

LCMS (ES): Found 350.9 [M+H]⁺.

A solution of (4) (251 mg, 0.72 mmol) in 0.85M hydroxylamine in MeOH (10 mL) was stirred at rt for 72 h. The solvent concentrated to dryness and the residue purified by reverse HPLC to give Example JJ (101 mg, 40%) as a beige solid.

¹H NMR (500 MHz, DMSO-d₆), $\delta_H$ ppm: 8.11 (dd, J=2.6, 1.6 Hz, 1H), 8.07 (dd, J=4.7, 1.3 Hz, 1H), 7.93 (d, J=2.7 Hz, 1H), 7.79 (d, J=1.4 Hz, 1H), 7.61 (d, J=8.2 Hz, 2H), 7.58 (dd, J=8.2, 1.2 Hz, 1H), 7.38 (d, J=8.2 Hz, 2H), 7.32 (dd, J=8.2, 4.7 Hz, 1H), 5.30 (s, 2H), 3.76 (s, 3H).

LCMS (ES): Found 352.1 [M+H]⁺.

Example KK

3-Fluoro-N-hydroxy-4-{[(3-methoxypyridin-2-yl)(pyrazin-2-yl)amino]methyl}benzamide

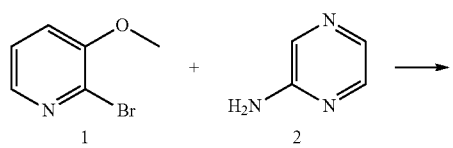

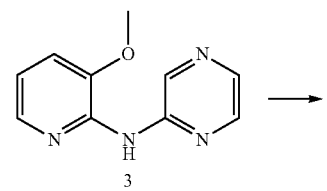

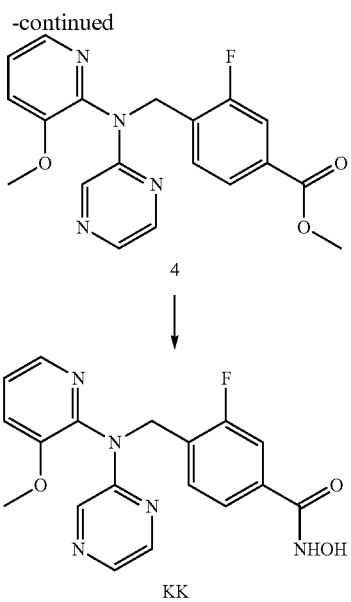

NaH (60%, 41.5 mg, 1.04 mmol) was added to a solution of (3) (200 mg, 0.99 mmol) in DMF (10 mL) at 5° C. under N₂(g). The reaction mixture was stirred for 20 min then methyl 4-(bromomethyl)-3-fluorobenzoate (318 mg, 1.29 mmol) was added. The stirring was continued at 70° C. under N₂(g) for 1 h. The reaction cooled to rt and poured onto water (150 mL) and brine (50 mL), the aqueous extracted with EtOAc (3×100 mL). Combined organics were dried over Na₂SO₄, filtered and concentrated in vacuo. The residue was purified by flash column chromatography with CH₂Cl₂/EtOAc (1:0-0:1) then EtOAc/MeOH (1:0-4:1) to give (4) (269 mg, 74%).

¹H NMR (500 MHz, Chloroform-d), $\delta_H$ ppm: 8.09 (dd, J=4.7, 1.4 Hz, 1H), 8.06 (dd, J=2.6, 1.6 Hz, 1H), 7.90 (d, J=2.7 Hz, 1H), 7.80 (d, J=1.3 Hz, 1H), 7.68 (dd, J=8.0, 1.4 Hz, 1H), 7.62 (dd, J=10.5, 1.4 Hz, 1H), 7.56 (t, J=7.7 Hz, 1H), 7.27 (dd, J=8.3, 1.5 Hz, 1H), 7.18 (dd, J=8.2, 4.7 Hz, 1H), 5.43 (s, 2H), 3.86 (s, 3H), 3.77 (s, 3H).

LCMS (ES): Found 368.9 [M+H]⁺.

A solution of (4) (269 mg, 0.73 mmol) in 0.85M hydroxylamine in MeOH (10 mL) was stirred at rt for 72 h. The solvent was concentrated to dryness and the residue purified by reverse phase HPLC to give Example KK (93 mg, 35%).

¹H NMR (500 MHz, DMSO-d₆), $\delta_H$ ppm: 8.13 (dd, J=2.6, 1.6 Hz, 1H), 8.08 (dd, J=4.7, 1.3 Hz, 1H), 7.95 (d, J=2.7 Hz, 1H), 7.80 (d, J=1.3 Hz, 1H), 7.61 (dd, J=8.3, 1.2 Hz, 1H), 7.48-7.43 (m, 3H), 7.35 (dd, J=8.2, 4.7 Hz, 1H), 5.32 (s, 2H), 3.78 (s, 3H).

LCMS (ES): Found 370.1 [M+H]⁺.

Example LL

N-Hydroxy-6-{[(3-methoxypyridin-2-yl)(pyrazin-2-yl)amino]methyl}pyridine-3-carboxamide -continued

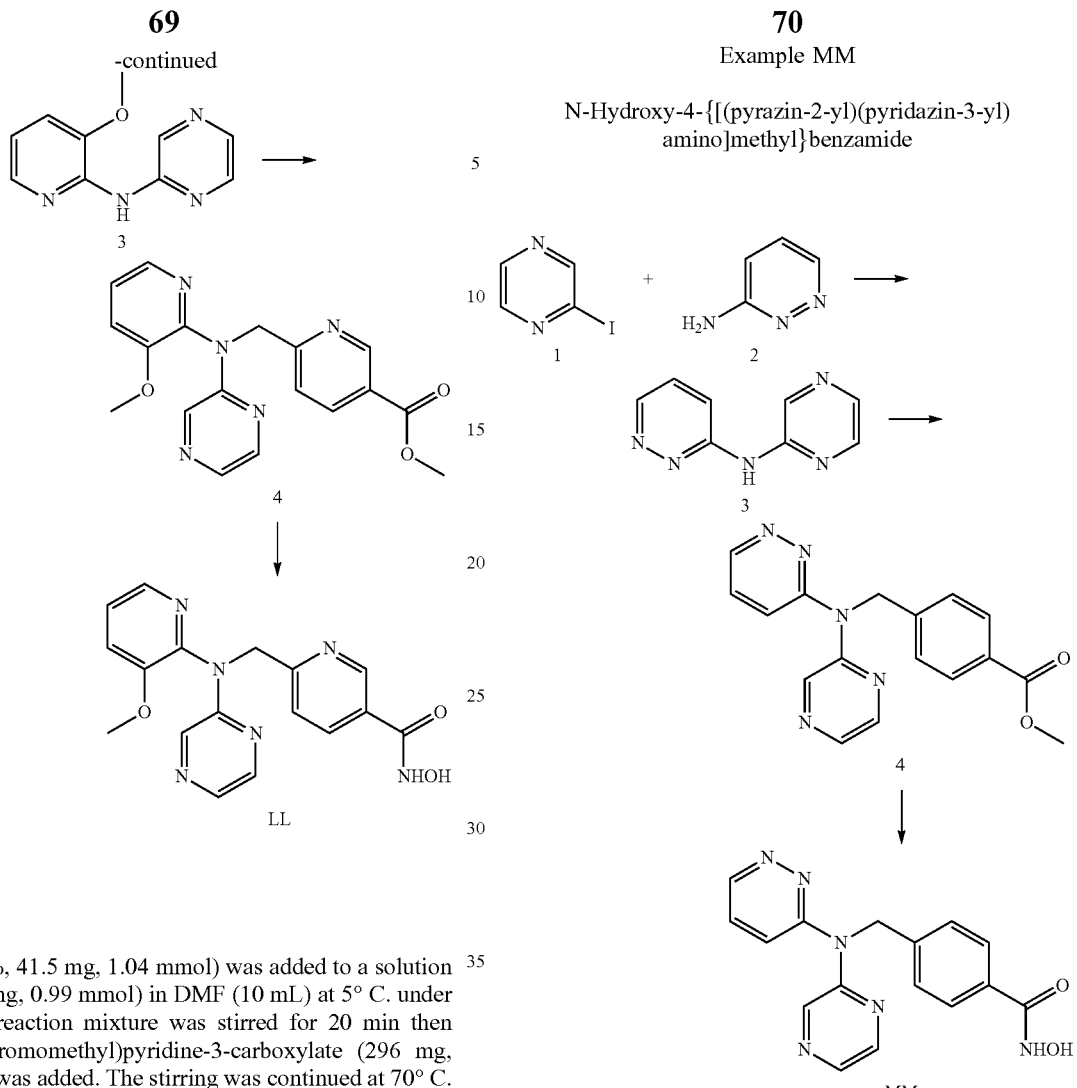

Example MM

N-Hydroxy-4-{[(pyrazin-2-yl)(pyridazin-3-yl)amino]methyl}benzamide

NaH (60%, 41.5 mg, 1.04 mmol) was added to a solution of (3) (200 mg, 0.99 mmol) in DMF (10 mL) at 5° C. under $N_2(g)$. The reaction mixture was stirred for 20 min then methyl 6-(bromomethyl)pyridine-3-carboxylate (296 mg, 1.29 mmol) was added. The stirring was continued at 70° C. under $N_2(g)$ for 1 h. The reaction was cooled to rt and poured onto water (150 mL) and brine (50 mL) and the aqueous extracted with EtOAc (3×100 mL). Combined organics were dried over $Na_2SO_4$, filtered and concentrated in vacuo. The residue was purified by flash column chromatography with $CH_2Cl_2$/EtOAc (1:0-0:1) then EtOAc/MeOH (1:0-4:1) to give (4) (191 mg, 55%).

$^1$H NMR (500 MHz, Chloroform-d), $\delta_H$ ppm: 9.07 (d, J=1.9 Hz, 1H), 8.12 (dd, J=8.2, 2.1 Hz, 1H), 8.06 (dd, J=4.7, 1.4 Hz, 1H), 8.01 (dd, J=2.6, 1.6 Hz, 1H), 7.88 (d, J=2.7 Hz, 1H), 7.84 (d, J=1.4 Hz, 1H), 7.54 (d, J=8.2 Hz, 1H), 7.27 (dd, J=8.2, 1.4 Hz, 1H), 7.17 (dd, J=8.2, 4.7 Hz, 1H), 5.46 (s, 2H), 3.86 (s, 3H), 3.76 (s, 3H).

LCMS (ES): Found 352.0 [M+H]$^+$.

A solution of (4) (191 mg, 0.54 mmol) in 0.85M hydroxylamine in MeOH (10 mL) was stirred at rt for 72 h. After this time the solvent was concentrated to dryness and the residue purified by reverse phase HPLC to give Example LL (35 mg, 19%).

$^1$H NMR (500 MHz, DMSO-d$_6$), $\delta_H$ ppm: 8.72 (d, J=1.8 Hz, 1H), 8.12-8.08 (m, 1H), 8.06 (dd, J=4.7, 1.3 Hz, 1H), 7.93 (d, J=2.7 Hz, 1H), 7.81-7.87 (m, 2H), 7.56-7.61 (m, 1H), 7.32 (dd, J=8.2, 4.7 Hz, 1H), 7.25 (d, J=8.1 Hz, 1H), 5.29 (s, 2H), 3.77 (s, 3H).

LCMS (ES): Found 353.1 [M+H]$^+$.

A solution of 2-iodopyrazine (1) (2.40 g, 11.65 mmol), pyridazin-3-amine (2) (1.2 g, 12.82 mmol), $Cs_2CO_3$ (7.6 g, 23.3 mmol) and Xantphos (297 mg, 0.51 mmol) in dioxane (45 mL) was purged with $N_2(g)$ for 10 min. $Pd_2(dba)_3$ (214 mg, 0.23 mmol) in dioxane (5 mL) was added and mixture was heated to 90° C. for 3 h. The reaction was cooled to rt and partitioned between water (200 mL) and EtOAc (200 mL). The insoluble solid was filtered and put a-side. The phases were separated and aqueous was extracted with EtOAc (200 mL), then $CH_2Cl_2$-IPA (200 mL, 4:1). Combined organics were dried over $Na_2SO_4$, filtered and concentrated in vacuo. The residue was purified by flash column chromatography with $CH_2Cl_2$/EtOAc (1:0-0:1) then EtOAc/MeOH (1:0-4:1) to yield (3). The solid [from filtration] was washed with water (100 mL) and triturated with hot MeOH (3×100 mL) and filtered. The filtrates were concentrated to yield a second batch of (3). The solid was further washed with water (100 mL) and was sucked dry to yield a third batch of (3). All three batches were combined to give (3) (1.63 g, 80%).

$^1$H NMR (500 MHz, DMSO-d$_6$), $\delta_H$ ppm: 10.49 (s, 1H), 9.00 (d, J=1.2 Hz, 1H), 8.83 (dd, J=4.6, 1.2 Hz, 1H), 8.27 (dd, J=2.5, 1.5 Hz, 1H), 8.16 (d, J=2.7 Hz, 1H), 8.06 (dd, J=9.1, 1.2 Hz, 1H), 7.60 (dd, J=9.1, 4.6 Hz, 1H).

LCMS (ES): Found 174.2 [M+H]$^+$.

NaH (60%, 49 mg, 1.21 mmol) was added to a solution of (3) (200 mg, 1.15 mmol) in DMF (8 mL) at 5° C. under N₂(g). The reaction mixture was stirred for 20 min then methyl 4-(bromomethyl)benzoate (344 mg, 1.5 mmol) in DMF (2 mL) was added. The stirring was continued at 70° C. under N₂(g) for 1 h. The reaction was cooled to rt, and poured onto water (200 mL) and brine (50 mL) and the aqueous extracted with EtOAc (2×150 mL). Combined organics were dried over Na₂SO₄, filtered and concentrated in vacuo. The residue was purified by flash column chromatography with heptane/EtOAc (1:0-0:1) then EtOAc/MeOH (1:0-4:1) yielded (4) (119 mg, 32%) as a brown oil.

¹H NMR (250 MHz, Chloroform-d), δ_H ppm: 8.85 (dd, J=4.6, 1.4 Hz, 1H), 8.56 (d, J=1.4 Hz, 1H), 8.25 (dd, J=2.6, 1.5 Hz, 1H), 8.17 (d, J=2.6 Hz, 1H), 7.89-7.97 (m, 2H), 7.48 (dd, J=9.1, 1.4 Hz, 1H), 7.42 (d, J=8.5 Hz, 2H), 7.33 (dd, J=9.1, 4.6 Hz, 1H), 5.64 (s, 2H), 3.86 (s, 3H).

LCMS (ES): Found 321.0 [M+H]⁺.

A solution of (4) (119 mg, 0.37 mmol) in 0.85M hydroxylamine in MeOH (10 mL) was stirred at rt for 72 h. After this time the solvent was concentrated to dryness and the residue purified by reverse phase HPLC to give Example MM (24 mg, 20%) as a beige solid.

¹H NMR (500 MHz, Methanol-d₄), δ_H ppm: 8.81 (dd, J=4.6, 1.2 Hz, 1H), 8.65 (d, J=1.4 Hz, 1H), 8.33 (dd, J=2.6, 1.5 Hz, 1H), 8.16 (d, J=2.6 Hz, 1H), 7.68 (d, J=8.6 Hz, 3H), 7.56 (dd, J=9.1, 4.6 Hz, 1H), 7.35 (d, J=8.2 Hz, 2H), 5.57 (s, 2H).

LCMS (ES): Found 322.2 [M+H]⁺.

Example NN

3-Fluoro-N-hydroxy-4-{[(pyrazin-2-yl)(pyridazin-3-yl)amino]methyl}benzamide

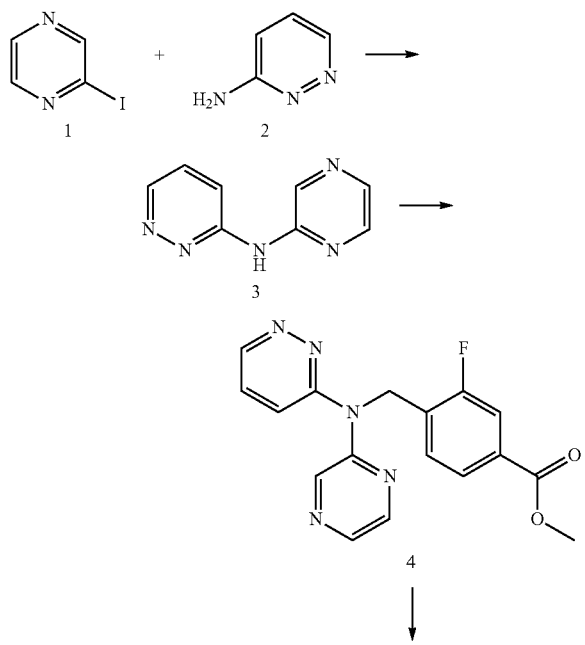

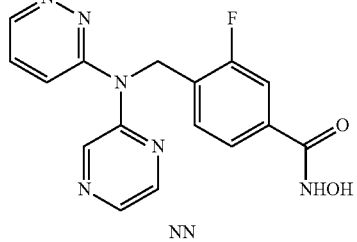

NN

NaH (60%, 73 mg, 1.82 mmol) was added to a solution of (3) (300 mg, 1.73 mmol) in DMF (11 mL) at 5° C. under N₂(g). The reaction mixture was stirred for 20 min then methyl 4-(bromomethyl)-3-fluorobenzoate (556 mg, 2.25 mmol) in DMF (4 mL) was added. The stirring was continued at 70° C. under N₂(g) for 1 h. The reaction was cooled to rt and poured onto water (150 mL) and brine (25 mL) and the aqueous extracted with EtOAc (150+100 mL). Combined organic were dried over Na₂SO₄, filtered and concentrated. The residue was purified by flash column chromatography with CH₂Cl₂/EtOAc (1:0-0:1) then EtOAc/MeOH (1:0-4:1) to yield (4) (141 mg, 24%) as a brown oil.

¹H NMR (500 MHz, Chloroform-d), δ_H ppm: 8.85 (dd, J=4.6, 1.3 Hz, 1H), 8.59 (d, J=1.4 Hz, 1H), 8.23 (dd, J=2.6, 1.5 Hz, 1H), 8.18 (d, J=2.6 Hz, 1H), 7.61-7.71 (m, 2H), 7.50 (dd, J=9.1, 1.3 Hz, 1H), 7.32-7.42 (m, 2H), 5.64 (s, 2H), 3.86 (s, 3H).

LCMS (ES): Found 339.9 [M+H]⁺.

A solution of (4) (141 mg, 0.42 mmol) in 0.85M hydroxylamine in MeOH (10 mL) was stirred at rt for 18 h. The solvent was concentrated to dryness and the residue purified by reverse phase HPLC to give Example NN (51 mg, 36%) as a beige solid.

¹H NMR (500 MHz, Methanol-d₄), δ_H ppm: 8.83 (dd, J=4.6, 1.1 Hz, 1H), 8.67 (d, J=1.3 Hz, 1H), 8.34 (dd, J=2.5, 1.5 Hz, 1H), 8.18 (d, J=2.6 Hz, 1H), 7.70 (dd, J=9.1, 1.2 Hz, 1H), 7.59 (dd, J=9.1, 4.6 Hz, 1H), 7.47 (d, J=11.7 Hz, 2H), 7.32 (t, J=8.0 Hz, 1H), 5.60 (s, 2H).

LCMS (ES): Found 341.0 [M+H]⁺.

Example OO

N-Hydroxy-4-{[(3-methyl-1,2,4-thiadiazol-5-yl)(pyrazin-2-yl)amino]methyl}benzamide

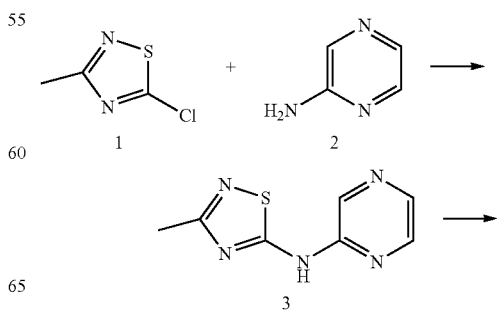

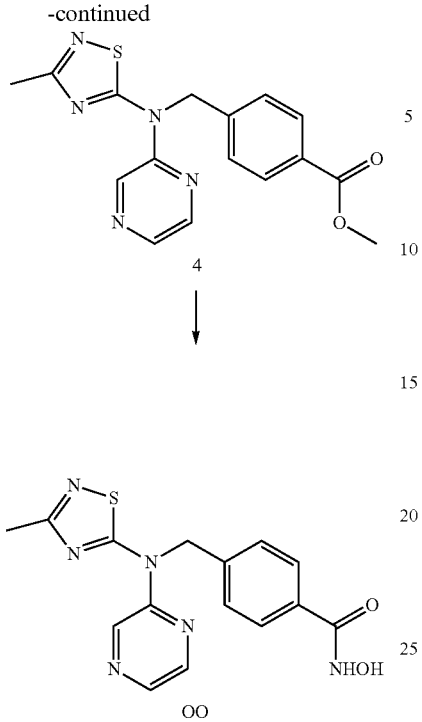

NaH (60%, 120 mg, 3.3 mmol) was added to a solution of (2) (140 mg, 1.47 mmol) in THF (10 mL) under N₂(g). The reaction mixture was stirred for 10 min then 5-chloro-3-methyl-1,2,4-thiadiazole (1) (190 mg, 1.41 mmol) was added. The mixture was heated up at 50° C. under N₂(g) for 24 h.

LCMS (ES): Found 194.0 [M+H]⁺.

To this mixture was added MeCN (10 mL), methyl 4-(bromomethyl)benzoate (400 mg, 1.74 mmol) and potassium carbonate (350 mg, 1.65 mmol). Heating was then continued at 50° C. for 2 h. Once cooled, the mixture was partitioned between H₂O (10 mL) and EtOAc (3×20 mL). Combined organics were dried over Na₂SO₄, filtered and concentrated in vacuo. The residue was purified by flash column chromatography with Petrol/EtOAc (1:0-1:1) to yield (4) (300 mg, 60% over 2 steps) as a white solid.

¹H NMR (400 MHz, DMSO-d₆), δ$_H$ ppm: 8.55-8.77 (m, 2H), 8.41 (s, 1H), 7.92 (d, J=7.9 Hz, 2H), 7.39 (d, J=7.9 Hz, 2H), 5.92 (s, 2H), 3.82 (s, 3H), 2.42 (s, 3H).

LCMS (ES): Found 342.0 [M+H]⁺.

A solution of (4) (174 mg, 0.51 mmol) in 0.85M hydroxylamine in MeOH (10 mL) was stirred at 70° C. for 8 h. The solvent was concentrated to dryness and the residue purified by reverse phase HPLC to give Example OO (44 mg, 25%).

¹H NMR (400 MHz, DMSO-d₆), δ$_H$ ppm: 11.45-10.94 (m, 1H), 9.43-8.80 (m, 1H), 8.70 (d, J=1.3 Hz, 1H), 8.61 (dd, J=2.6, 1.5 Hz, 1H), 8.40 (d, J=2.6 Hz, 1H), 7.70 (d, J=8.5 Hz, 2H), 7.31 (d, J=8.3 Hz, 2H), 5.88 (s, 2H), 2.43 (s, 3H).

LCMS (ES): Found 343.0 [M+H]⁺.

Example PP

N-Hydroxy-4-{[(4-methoxypyridin-2-yl)(pyrazin-2-yl)amino]methyl}benzamide

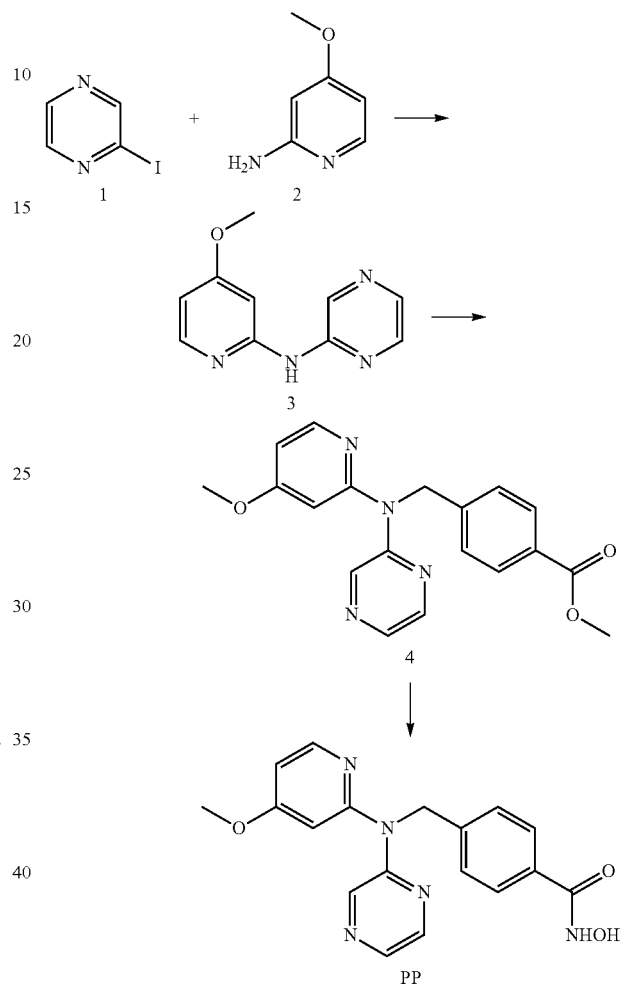

A solution of 2-iodopyrazine (1) (1.34 g, 6.51 mmol), 4-methoxypyridin-2-amine (2) (0.85 g, 6.83 mmol), Cs₂CO₃ (4.24 g, 13.01 mmol) and Xantphos (0.17 g, 0.29 mmol) in dioxane (22 mL) was purged with N₂(g) for 10 min then Pd₂(dba)₃ (0.12 g, 0.13 mmol) was added, re-purged for ~5 min and reaction was heated to 90° C. for 4 h. Once cooled down to rt, the mixture was partitioned between H₂O (150 mL) and EtOAc (3×120 mL). Combined organics were dried over Na₂SO₄, filtered and concentrated in vacuo. The residue was purified by flash column chromatography with CH₂Cl₂/EtOAc (9:1-0:1) to yield (3) (809 mg, 61%) as a yellow solid.

¹H NMR (500 MHz, Chloroform-d), δ$_H$ ppm: 8.70 (d, J=1.3 Hz, 1H), 8.11-8.22 (m, 3H), 8.08 (d, J=2.7 Hz, 1H), 7.43 (d, J=2.2 Hz, 1H), 6.52 (dd, J=5.8, 2.3 Hz, 1H), 3.88 (s, 3H).

LCMS (ES): Found 203.2 [M+H]⁺.

NaH (60%, 42 mg, 1.04 mmol) was added to a solution of (3) (200 mg, 0.99 mmol) in DMF (7 mL) at rt under N₂(g). The reaction mixture was stirred for 30 min then methyl 4-(bromomethyl)-3-fluorobenzoate (249 mg, 1.09 mmol) in DMF (2 mL) was added. The reaction was heated up to 70° C. under N₂(g) for 2 h, then at rt overnight. The reaction was cooled to rt and partitioned between H₂O (150 mL) and EtOAc (2×100 mL). Combined organics were dried over Na₂SO₄, filtered and concentrated in vacuo. The residue was purified by flash column chromatography with CH₂Cl₂/EtOAc (1:0-0:1) to yield (4) (173 mg, 50%) as a viscous oil.

¹H NMR (300 MHz, Chloroform-d), δ$_H$ ppm: 8.63 (dd, J=1.4 Hz, 1H), 8.14-8.22 (m, 2H), 8.01 (d, J=2.6 Hz, 1H), 7.92 (d, J=8.2 Hz, 2H), 7.39 (d, J=8.2 Hz, 2H), 6.61 (d, J=2.1 Hz, 1H), 6.54 (dd, J=5.8, 2.2 Hz, 1H), 5.46 (s, 2H), 3.85 (s, 3H), 3.75 (s, 3H).

LCMS (ES): Found 350.9 [M+H]⁺.

A solution of (4) (173 mg, 0.49 mmol) in 0.85M hydroxylamine in MeOH (10 mL) was stirred at rt for 72 h. The solvent was concentrated to dryness and the residue purified by reverse phase HPLC to give Example PP (15 mg, 9%).

¹H NMR (500 MHz, Methanol-d₄), δ$_H$ ppm: 8.46 (d, J=1.4 Hz, 1H), 8.24 (dd, J=2.6, 1.5 Hz, 1H), 8.14 (d, J=5.9 Hz, 1H), 8.00 (d, J=2.7 Hz, 1H), 7.65 (d, J=8.3 Hz, 2H), 7.42 (d, J=8.3 Hz, 2H), 6.79 (d, J=2.2 Hz, 1H), 6.73 (dd, J=5.9, 2.2 Hz, 1H), 5.45 (s, 2H), 3.82 (s, 3H).

LCMS (ES): Found 352.0 [M+H]⁺.

Example QQ

N-Hydroxy-4-{[(pyrazin-2-yl)[6-(trifluoromethyl)pyrazin-2-yl]amino]methyl}benzamide

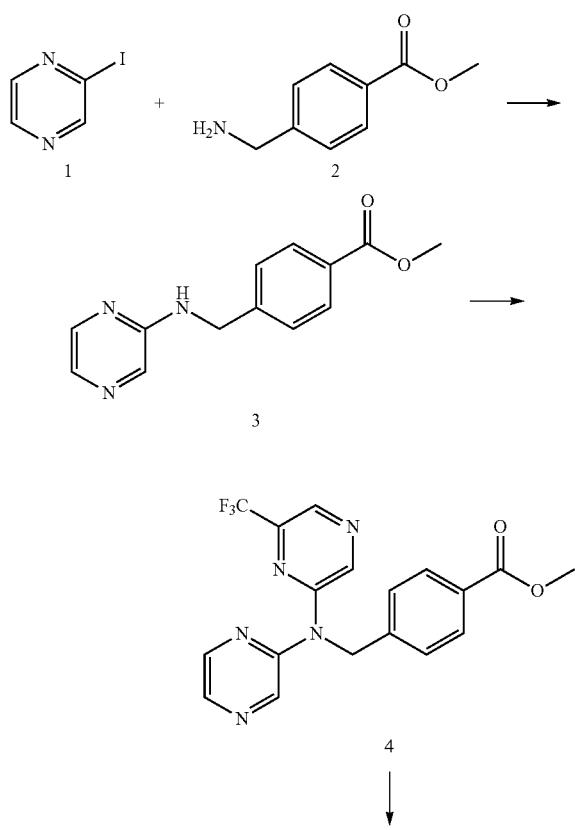

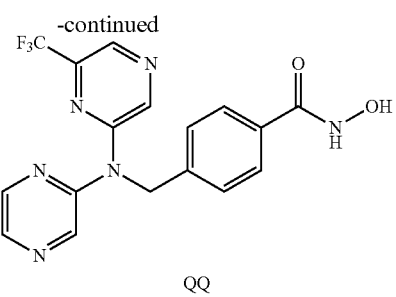

To a solution of methyl 4-(aminomethyl)benzoate hydrochloride (1.47 g, 7.3 mmol) in DMSO (14 mL) was added 2-iodopyrazine (1 g, 4.9 mmol) followed by K₂CO₃ (1.7 g, 12.1 mmol) under Ar(g). After 2 min vigorous stirring, CuI (46 mg, 0.2 mmol) was added and the mixture was left to stir at rt overnight. It was partitioned between EtOAc (150 mL) and 50% brine (50 mL) and the organic layer separated, the aqueous extracted with EtOAc (2×15 mL), before the combined organic phase was washed with 50% brine (15 mL), dried (MgSO₄), and concentrated in vacuo. The residue was purified by flash column chromatography with Hexane/EtOAc (7:3-0:1) to yield (3) (670 mg, 57%) as a white solid.

¹H NMR (300 MHz, CHLOROFORM-d) δ$_H$ ppm: 7.76-8.11 (m, 5H), 7.43 (d, J=8.5 Hz, 2H), 5.01-5.16 (m, 1H), 4.66 (d, J=5.8 Hz, 2H), 3.92 (s, 3H).

LCMS (ES): Found 352.0 [M+H]⁺.

To compound (2) (60 mg, 0.25 mmol), Pd₂(dba)₃ (11 mg, 0.01 mmol), (±)-BINAP (15 mg, 0.025 mmol) and Cs₂CO₃ (241 mg, 0.74 mmol) was added a solution of 2-chloro-6-(trifluoromethyl)pyrazine (90 mg, 0.49 mmol) in dioxane (2 mL) under Ar(g). The reaction mixture was heated at 90° C. for 4 h then allowed to cool to rt overnight. EtOAc (15 mL), water (4 mL) and brine (2 mL) were then added and the organic phase separated, extracting the aqueous with EtOAc (10 mL). The combined organic phases were dried (MgSO₄) and concentrated in vacuo to give a crude residue (153 mg). The residue was scavenged by dissolving in CH₂Cl₂/MeOH (1:1, 10 mL) followed by the addition of MP-TMT (370 mg, 0.68 mmol/g). The mixture was agitated for 24 h before filtering off the resin, washing with CH₂Cl₂/MeOH (1:1, 2×5 mL). The filtrate was then concentrated in vacuo to give crude (3) (132 mg), as a brown solid which was used directly in the next step.

To a solution of crude (3) (132 mg total, containing maximum 0.25 mmol) in THF/MeOH (1:1, 4 mL) was added NH₂OH solution (50% wt. H₂O, 3064, 5 mmol) followed by NaOH (6M, 834, 0.5 mmol). After 50 min stirring at rt, KHSO₄ (1M, 2 mL), water (5 mL) and CH₂Cl₂ (6 mL) were added. The organic phase was separated and the aqueous extracted with CH₂Cl₂ (2×5 mL). The combined organic phase was dried (MgSO₄) and concentrated in vacuo to give a yellow solid. Purification by reverse phase C-18 chromatography with MeCN/H₂O (19:1-1:1) gave Example QQ (81 mg, 83% over 2 steps) as a light brown solid.

¹H NMR (DMSO-d₆) δ$_H$ ppm: 8.93 (s, 1H), 8.88 (d, J=1.7 Hz, 1H), 8.62 (s, 1H), 8.42 (dd, J=2.6, 1.5 Hz, 1H), 8.34 (d, J=2.6 Hz, 1H), 7.62 (d, J=8.3 Hz, 2H), 7.27 (d, J=8.3 Hz, 2H), 5.46 (s, 2H).

LCMS (ES): Found 391.1 [M+H]⁺.

Example RR 4-({[5-(6-Aminopyridin-3-yl)pyridin-2-yl](pyrazin-2-yl)amino}methyl)-N-hydroxybenzamide

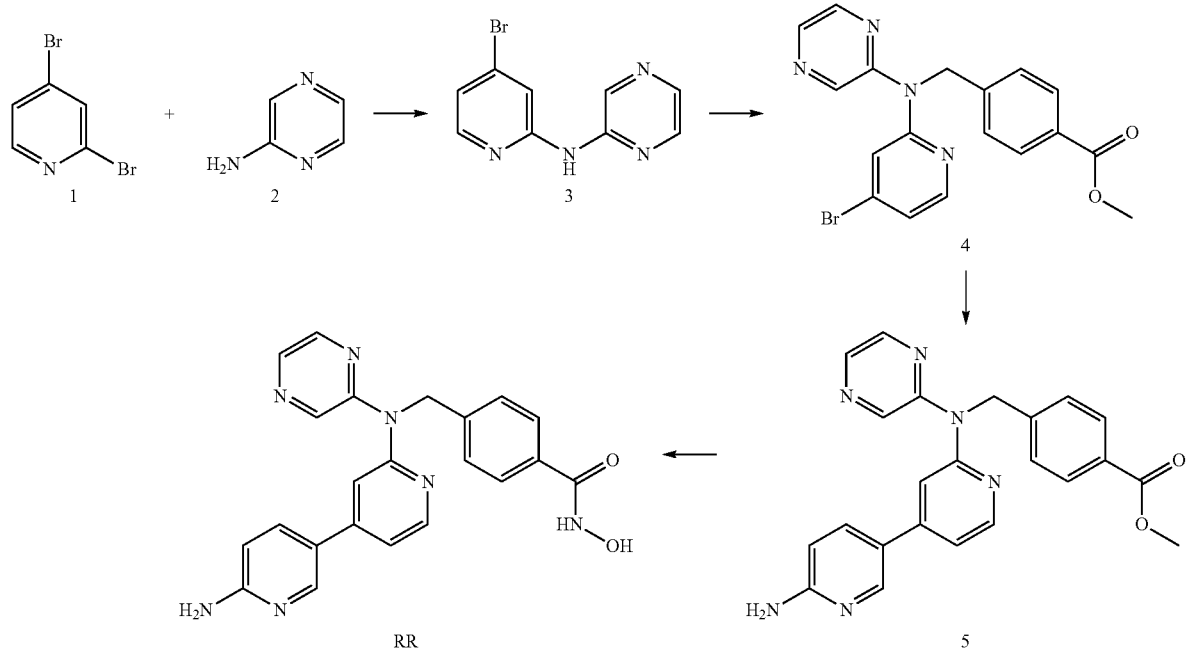

A mixture of 2,4-dibromopyridine (1) (5.0 g, 21.1 mmol), pyrazin-2-amine (2) (2.21 g, 23.22 mmol), Cs₂CO₃ (15.1 g, 46.4 mmol) and Xantphos (611 mg, 1.05 mmol) was suspended in dioxane (50 mL). The mixture was flushed with N₂(g) for 1 min before Pd₂(dba)₃ (386 mg, 0.422 mmol) was added. Mixture was flushed again with N₂(g) and it was heated up to 90° C. overnight. Once cooled, the mixture was partitioned between H₂O (150 mL) and EtOAc (3×150 mL). The combined organic extracts were washed with brine, dried with MgSO₄, filtered and concentrated in vacuo. Purification by flash column chromatography with heptane/EtOAc (9:1-2:3) to yield (3) (2.6 g, 49%) as pale yellow solid.

¹H NMR (500 MHz, Chloroform-d), $\delta_H$ ppm: 8.74 (d, J=1.3 Hz, 1H), 8.22 (dd, J=2.6, 1.5 Hz, 1H), 8.15 (d, J=2.7 Hz, 1H), 8.11 (d, J=5.4 Hz, 1H), 8.07 (d, J=1.5 Hz, 1H), 7.63 (s, 1H), 7.10 (dd, J=5.4, 1.6 Hz, 1H).

LCMS (ES): Found 251.0-253.0 [M+H]⁺.

To a solution of (3) (1.08 g, 4.3 mmol) in DMF (15 mL) cooled to 0° C. under N₂(g) was added NaH (60%, 206 mg, 5.16 mmol). The mixture was stirred for 30 min. Then, a solution of methyl 4-(bromomethyl)benzoate (1.08 g, 4.73 mmol) in DMF (5 mL) was added and the mixture was heated up to 50° C. for 1.5 h. Once cooled down, the reaction was partitioned between H₂O (150 mL) and EtOAc (3×150 mL). The combined organic extracts were washed with brine, dried with MgSO₄, filtered and concentrated in vacuo. Purification by flash column chromatography with heptane/EtOAc (9:1-2:3) to yield (4) (915 mg, 53%) as white solid.

¹H NMR (500 MHz, Chloroform-d), $\delta_H$ ppm: 8.66 (d, J=1.4 Hz, 1H), 8.25 (dd, J=2.5, 1.6 Hz, 1H), 8.15 (d, J=5.3 Hz, 1H), 8.13 (d, J=2.6 Hz, 1H), 7.95 (d, J=8.3 Hz, 2H), 7.39 (d, J=8.3 Hz, 2H), 7.33 (d, J=1.4 Hz, 1H), 7.10 (dd, J=5.3, 1.5 Hz, 1H), 5.49 (s, 2H), 3.88 (s, 3H).

LCMS (ES): Found 399.0-401.0 [M+H]⁺.

To a suspension of (4) (200 mg, 0.50 mmol), 5-(4,4,5,5-tetramethyl-1,3,2-dioxaborolan-2-yl)pyridin-2-amine (132.3 mg, 0.6 mmol) and Cs₂CO₃ (326 mg, 1.0 mmol) in DMF (4 mL) and H₂O (1 mL) was added Pd(PPh₃)₄ (58 mg, 0.05 mmol). The mixture was flushed with N₂(g) then it was heated up to 90° C. for 2 h. Once cooled down, H₂O (20 mL) was added and a precipitate was left to settle at rt for 72 h. After filtration, washings with H₂O (2 mL) and drying, (5) was obtained as a brown solid (219 mg, quant.).

¹H NMR (500 MHz, Methanol-d₄), $\delta_H$ ppm: 8.54 (s, 1H), 8.31 (d, J=5.3 Hz, 1H), 8.25-8.28 (m, 1H), 8.23 (d, J=2.3 Hz, 1H), 8.02 (d, J=2.6 Hz, 1H), 7.92 (d, J=8.2 Hz, 2H), 7.77 (dd, J=8.8, 2.4 Hz, 1H), 7.50 (s, 1H), 7.48 (d, J=5.5 Hz, 2H), 7.32 (d, J=5.4 Hz, 1H), 6.65 (d, J=8.8 Hz, 1H), 5.55 (s, 2H), 3.86 (s, 3H).

LCMS (ES): Found 413.0 [M+H]⁺.

A solution of (5) (219 mg, 0.53 mmol) in 0.85M NH₂OH in MeOH (5 mL) was stirred at rt overnight. The volatiles were then removed in vacuo and the residue was purified by reverse prep HPLC to give Example RR (19 mg, 8%) as pale yellow solid.

1H NMR (500 MHz, DMSO-d₆), $\delta_H$ ppm: 8.63 (d, J=1.4 Hz, 1H), 8.35 (d, J=2.3 Hz, 1H), 8.27-8.28 (m, 1H), 8.26-8.27 (m, 1H), 8.07 (d, J=2.6 Hz, 1H), 7.76 (d, J=2.6 Hz, 1H), 7.61 (d, J=8.3 Hz, 2H), 7.51 (s, 1H), 7.30 (dd, J=5.3, 1.5 Hz, 1H), 7.26 (d, J=8.2 Hz, 2H), 6.52 (d, J=8.7 Hz, 1H), 6.36 (s, 2H), 5.45 (s, 2H).

LCMS (ES): Found 414.0 [M+H]⁺.

Example SS 4-({[5-(2-Aminopyridin-4-yl)pyridin-2-yl](pyrazin-2-yl)amino}methyl)-N-hydroxybenzamide

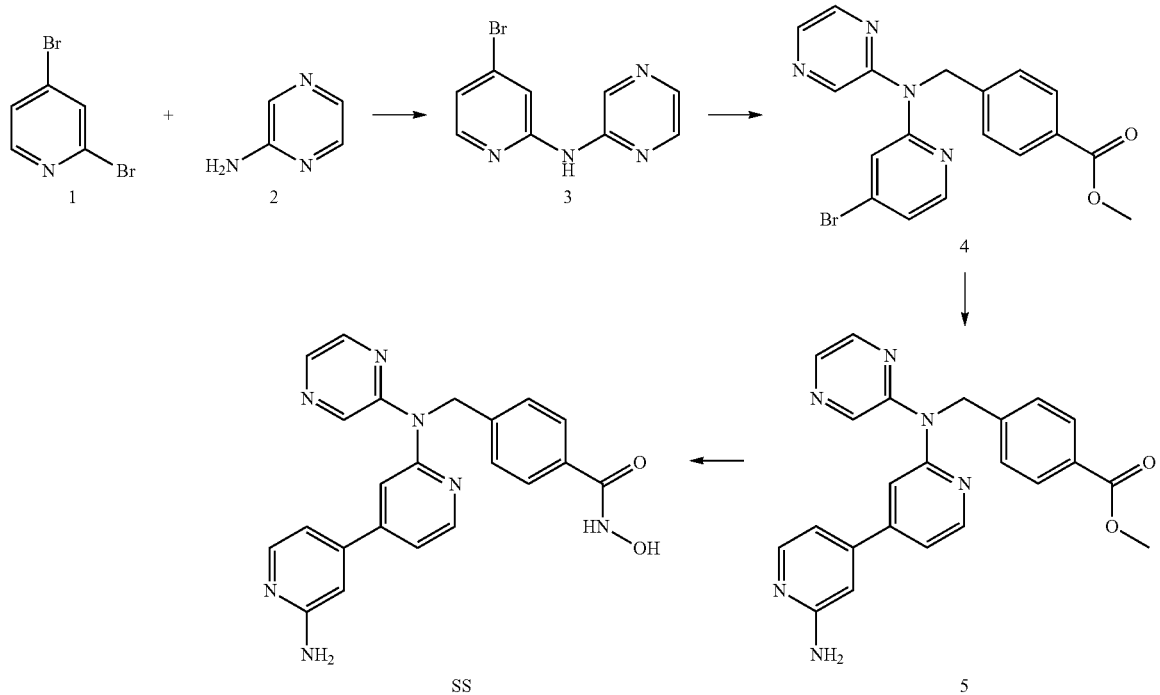

To a suspension of (4) (200 mg, 0.50 mmol), 4-(4,4,5,5-tetramethyl-1,3,2-dioxaborolan-2-yl)pyridin-2-amine (132.3 mg, 0.6 mmol) and $Cs_2CO_3$ (326 mg, 1.0 mmol) in DMF (4 mL) and $H_2O$ (1 mL) was added $Pd(PPh_3)_4$ (58 mg, 0.05 mmol). The mixture was flushed with $N_2$(g) then it was heated up to 90° C. for 2 h. Once cooled down, $H_2O$ (20 mL) was added and a precipitate was left to settle at rt for 3 h. After filtration, washings with $H_2O$ (2 mL) and drying, a pale orange solid was obtained, which was purified by flash column chromatography with heptane/EtOAc (4:1-0:1) then EtOAc/MeOH (1:0-7:3) to give (5) (82 mg, 40%) as a yellow solid.

1H NMR (500 MHz, Methanol-$d_4$), $\delta_H$ ppm: 8.60 (s, 1H), 8.41 (d, J=5.2 Hz, 1H), 8.29 (d, J=1.3 Hz, 1H), 8.06 (d, J=2.5 Hz, 1H), 7.97 (d, J=5.4 Hz, 1H), 7.93 (d, J=8.3 Hz, 2H), 7.53 (s, 1H), 7.49 (d, J=8.1 Hz, 2H), 7.34 (d, J=5.2 Hz, 1H), 6.81-6.84 (m, 1H), 6.81 (s, 1H), 5.58 (s, 2H), 3.86 (s, 3H).

LCMS (ES): Found 413.0 [M+H]$^+$.

A solution of (5) (82 mg, 0.20 mmol) in 0.85M $NH_2OH$ in MeOH (5 mL) was stirred at rt overnight. The volatiles were then removed in vacuo and the residue was purified by reverse prep HPLC to give Example SS (19 mg, 8%) as white solid.

1H NMR (500 MHz, Methanol-$d_4$), $\delta_H$ ppm: 8.59 (d, J=1.4 Hz, 1H), 8.39 (d, J=5.2 Hz, 1H), 8.29 (dd, J=2.7, 1.5 Hz, 1H), 8.05 (d, J=2.7 Hz, 1H), 7.97 (d, J=5.5 Hz, 1H), 7.66 (d, J=8.3 Hz, 2H), 7.49 (s, 1H), 7.45 (d, J=8.2 Hz, 2H), 7.32 (dd, J=5.2, 1.2 Hz, 1H), 6.82 (dd, J=5.5, 1.3 Hz, 1H), 6.78 (s, 1H), 5.55 (s, 2H).

LCMS (ES): Found 414.0 [M+H]$^+$.

Example TT

N-hydroxy-4-[({5-[2-(methylamino)pyridin-4-yl]pyridin-2-yl}(pyrazin-2-yl)amino)methyl]benzamide

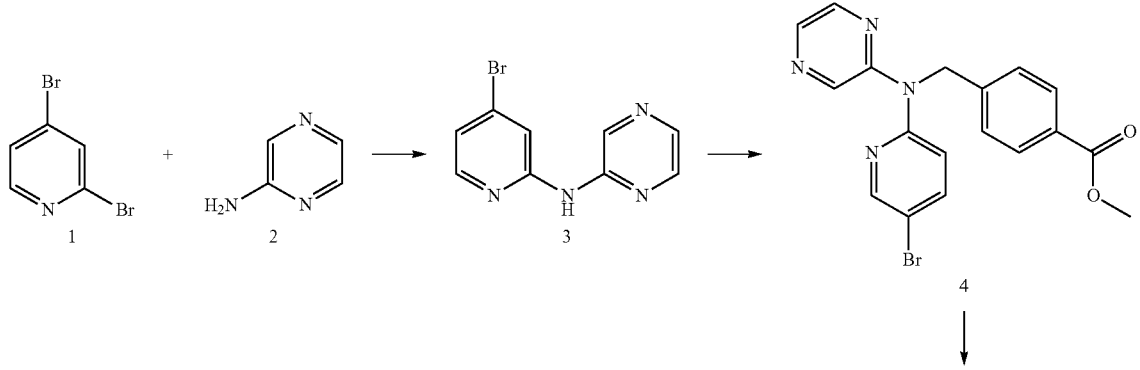

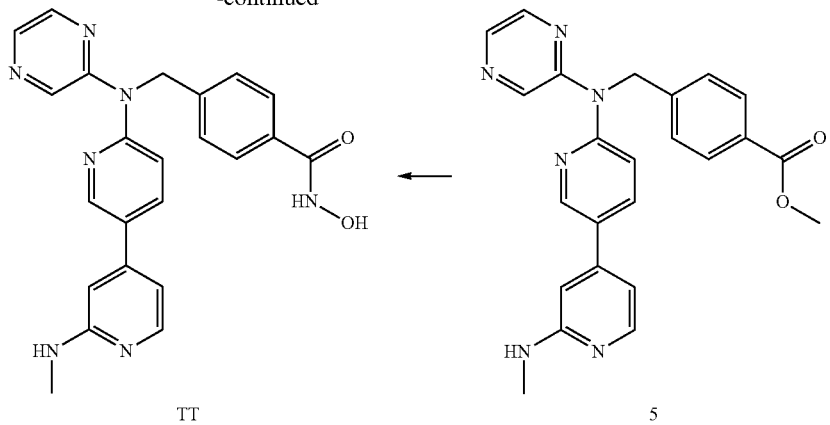

TT

5

To a suspension of (4) (120 mg, 0.3 mmol), N-methyl-4-(tetramethyl-1,3,2-dioxaborolan-2-yl)pyridin-2-amine (84 mg, 0.36 mmol) and Cs$_2$CO$_3$ (196 mg, 0.6 mmol) in DMF (2 mL) and H$_2$O (0.5 mL) was added Pd(PPh$_3$)$_4$ (58 mg, 0.05 mmol). The mixture was flushed with N$_2$(g) then it was heated up to 90° C. for 4 h. Once cooled down, H$_2$O (10 mL) was added and the reaction was stirred for 20 min.

After filtration, washings with MeCN (2 mL) and drying, a black solid was obtained, which was purified by preparative HPLC to give (5) (80 mg, 59%) as a white solid.

1H NMR (500 MHz, DMSO-d$_6$), $\delta_H$ ppm: 8.70 (d, J=1.4 Hz, 1H), 8.39 (d, J=5.2 Hz, 1H), 8.29 (dd, J=2.6, 1.5 Hz, 1H), 8.14 (d, J=2.6 Hz, 1H), 8.07 (d, J=5.3 Hz, 1H), 7.87 (d, J=8.4 Hz, 2H), 7.54-7.56 (m, 1H), 7.50 (d, J=8.3 Hz, 2H), 7.32 (dd, J=5.2, 1.4 Hz, 1H), 6.77 (dd, J=5.3, 1.5 Hz, 1H), 6.65-6.67 (m, 1H), 6.61 (d, J=5.2 Hz, 1H), 5.56 (s, 2H), 3.80 (s, 3H), 2.80 (d, J=4.9 Hz, 3H).

LCMS (ES): Found 427.5 [M+H]$^+$.

To a solution of (5) (80 mg, 0.20 mmol) in MeOH/THF (1:1, 2 mL) was added hydroxylamine (50% w/w in H$_2$O; 0.11 mL, 3.75 mmol) followed by 6N NaOH (634, 0.38 mmol). The mixture was stirred at rt for 3 h. Then, 1M KHSO$_4$ (2 mL) was added followed by H$_2$O (6 mL). It was extracted with IPA/Chloroform (1:2, 3×20 mL). The combined organic extracts were washed with brine, dried with MgSO$_4$, filtered and concentrated in vacuo. Purification by preparative HPLC yielded Example TT (21 mg, 25%) as a pale orange solid.

1H NMR (500 MHz, Methanol-d$_4$), $\delta_H$ ppm: 11.08 (br.s., 1H), 8.69 (dd, J=6.3, 1.4 Hz, 1H), 8.39 (dd, J=5.0, 1.4 Hz), 8.28-8.32 (m, 1H), 8.13 (dd, J=6.0, 2.6 Hz, 1H), 8.07 (dd, J=5.2, 3.3 Hz, 1H), 7.63-7.67 (m, 1H), 7.58 (d, J=8.4 Hz, 1H), 7.53 (m, 1H), 7.42 (d, J=8.4 Hz, 1H), 7.36 (d, J=8.4 Hz, 1H), 7.31 (ddd, J=8.5, 5.3, 1.4, 1H), 6.65 (ddd, J=8.5, 5.4, 1.5 Hz), 6.66 (d, J=9.1 Hz, 1H), 6.58-6.63 (m, 1H), 5.51 (m, 1H), 2.80 (dd, J=4.8, 2.9 Hz, 3H).

LCMS (ES): Found 428.2 [M+H]$^+$.

Example UU

N-hydroxy-4-{[(pyrazin-2-yl)[5-(pyridin-4-yl)pyridin-2-yl]amino]methyl}benzamide

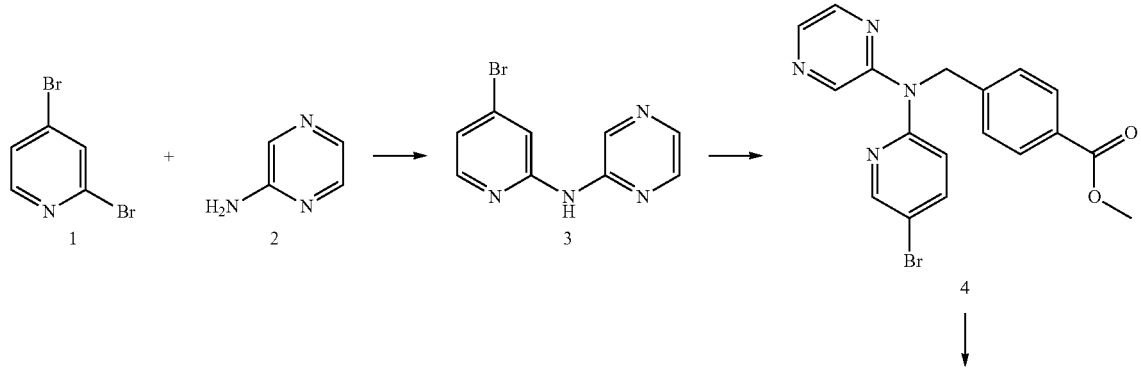

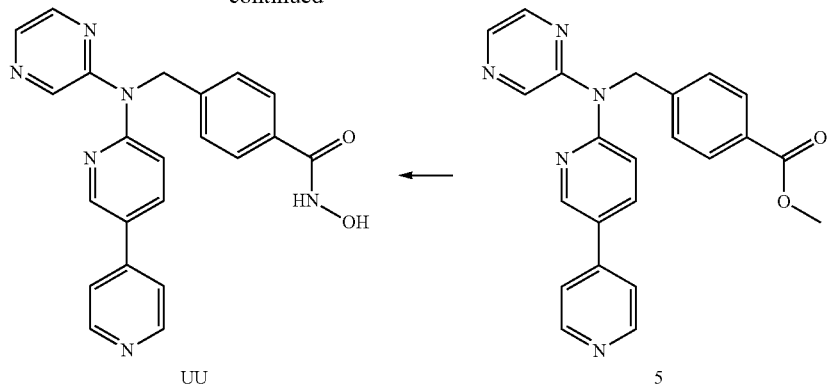

To a suspension of (4) (120 mg, 0.3 mmol), (pyridin-4-yl)boronic acid (49 mg, 0.36 mmol) and Cs$_2$CO$_3$ (196 mg, 0.6 mmol) in DMF (2 mL) and H$_2$O (0.5 mL) was added Pd(PPh$_3$)$_4$ (35 mg, 0.03 mmol). The mixture was flushed with N$_2$(g) then it was heated up to 90° C. for 4 h. Once cooled down, H$_2$O (10 mL) was added and the reaction was stirred for 20 min.

After filtration, a gum was obtained, which was purified by preparative HPLC then SCX column to give (5) (82 mg, 65%) as a colourless oil.

LCMS (ES): Found 398.5 [M+H]$^+$.

To a solution of (5) (82 mg, 0.21 mmol) in MeOH/THF (1:1, 2 mL) was added hydroxylamine (50% w/w in H$_2$O; 0.15 mL, 0.42 mmol) followed by 6N NaOH (804, 0.42 mmol). The mixture was stirred at rt for 2 h.

The volatiles were then removed in vacuo and the residue was purified by reverse prep HPLC to give Example UU (39 mg, 48%) as white solid.

1H NMR (500 MHz, DMSO-d$_6$), δ$_H$ ppm: 11.05 (br. s., 1H), 8.95 (br. s., 1H), 8.68-8.71 (m, 3H), 8.44 (d, J=5.2 Hz, 1H), 8.28-8.31 (m, 1H), 8.14 (d, J=2.6 Hz, 1H), 7.72-7.78 (m, 3H), 7.64 (d, J=8.2 Hz, 2H), 7.47 (dd, J=5.2, 1.4 Hz, 1H), 7.42 (d, J=8.0 Hz, 2H), 5.55 (s, 2H).

LCMS (ES): Found 399.4 [M+H]$^+$.

Biochemical Assay and Data
1) Assay
i. Biochemical Assay Description

Activity against all zinc-dependent HDACs 1 to 11 was assessed by using an acetylated AMC-labeled peptide substrate. The substrate RHKKAc was used for all class I and IIb HDACs; for HDAC8, the substrate used was RHKAcKAc. Activity against the class IIa HDACs (HDAC4, 5, 7, 9) was determined using a class IIa-specific substrate, Acetyl-Lys(trifluoroacetyl)-AMC (Lahm et al, 2007, PNAS, 104, 17335-17340). All assays were based on the AMC-labeled substrate and developer combination.

The protocol involved a two-step reaction: first, the substrate with the acetylated lysine side chain is incubated with a sample containing HDAC activity, to produce the deacetylated products, which are then digested in the second step by the addition of developer to produce the fluorescent signal proportional to the amount of deacetylated substrates.

ii. Enzymes

Human HDAC1 (GenBank Accession No. NM_004964), full length with C-terminal His-tag and C-terminal FLAG-tag, MW=56 kDa, expressed in baculovirus expression system.

Human HDAC2 (GenBank Accession No. NM_001527), full length with C-terminal His-tag, MW=56 kDa, expressed inbaculovirus expression system.

Complex of human HDAC3 (GenBank Accession No. NM_003883), full length with C-terminal His tag, MW=49.7 kDa, and human NCOR2 (amino acid 395-489) (GenBank Accession No. NM_006312), N-terminal GST tag, MW=37.6 kDa, co-expressed in baculovirus expression system.

Human HDAC4 (GenBank Accession No. NM_006037), amino acids 627-1085 with N-terminal GST tag, MW=75.2 kDa, expressed in baculovirus expression system.

Human HDAC5 (GenBank Accession No. NM_005474), full length with N-terminal GST tag, MW=150 kDa, expressed in baculovirus expression system.

Recombinant human HDAC6 (GenBank Accession No. BC069243), full length, MW=180 kDa, was expressed by baculovirus in Sf9 insect cells using an N-terminal GST tag.

Human HDAC7 (GenBank Accession No. AY302468), (a.a. 518-end) with N-terminal GST tag, MW=78 kDa, expressed in baculovirus expression system.

Human HDAC8 (GenBank Accession No. NM_018486), full length with C-terminal His tag, MW=46.4 kDa, expressed in a baculovirus expression system.

Human HDAC9 (GenBank Accession No. NM_178423), amino acids 604-1066 with C-terminal His tag, MW=50.7 kDa, expressed in baculovirus expression system.

Human HDAC10 (a.a. 1-481), GenBank Accession No. NM_032019 with N-terminal GST tag and C-terminal His tag, MW=78 kDa, expressed in baculovirus expression system.

Human HDAC11 (full length) (GenBank Accession No. NM_024827) with N-terminal GST tag, MW=66 kDa, expressed in baculovirus expression system.

iii. Reaction Conditions

Assay Buffer: 50 mM Tris-HCl, pH8.0, 137 mM NaCl, 2.7 mM KCl, 1 mM MgCl$_2$. Before use, 1 mg/mL BSA and DMSO are added.

HDAC1: 2.68 nM HDAC1 and 50 mM HDAC substrate are in the reaction buffer with 1% DMSO final. Incubate for 2 hours at 30° C.

HDAC2: 3.33 nM HDAC2 and 50 mM HDAC substrate are in the reaction buffer with 1% DMSO final. Incubate for 2 hours at 30° C.

HDAC3: 1.13 nM HDAC3 and 50 mM HDAC substrate are in the reaction buffer with 1% DMSO final. Incubate for 2 hours at 30° C.

HDAC6: 0.56 nM HDAC6 and 50 mM HDAC substrate are in the reaction buffer with 1% DMSO final. Incubate for 2 hours at 30° C.

HDAC8: 46.4 nM HDAC8 and 50 mM HDAC8 substrate are in the reaction buffer with 1% DMSO final. Incubate for 2 hours at 30° C.

HDAC10: 96.15 nM HDAC10 and 50 mM HDAC substrate are in the reaction buffer with 1% DMSO final. Incubate for 2 hours at 30° C.

HDAC11: 227.27 nM HDAC11 and 50 mM HDAC substrate are in the reaction buffer with 1% DMSO final. Incubate for 2 hours at 30° C.

For class IIa HDACs, assay buffer is the same.
Other reaction conditions are as follows:

HDAC4: 0.03 nM HDAC4 and 50 mM Class IIa HDAC substrate are in the reaction buffer with 1% DMSO final. Incubate for 30 minutes at room temperature.

HDAC5: 0.67 nM HDAC5 and 50 mM Class IIa HDAC substrate are in the reaction buffer with 1% DMSO final. Incubate for 30 minutes at room temperature.

HDAC7: 0.26 nM HDAC7 and 50 mM Class IIa HDAC substrate are in the reaction buffer with 1% DMSO final. Incubate for 30 minutes at room temperature.

HDAC9: 2.37 nM HDAC9 and 50 mM Class IIa HDAC substrate are in the reaction buffer with 1% DMSO final. Incubate for 30 minutes at room temperature.

Control Inhibitor: Trichostatin A (TSA)
Fluorescent Deacetylated Standard: Biomol, Cat#KI-142;
For Standard Control, compound is added at assay concentration to 2.5 uM
Fluorescent Deacetylated Standard; 10 doses in 6 uL
For Fluorescence Background Control, compound is added at assay concentrations to 50 mM HDAC substrate; 10 doses in 6 uL.
Fluorescence background signal is then subtracted from compound data signal.
% Conversion must be between 5% and 15% to obtain optimum result.

iv. Assay Procedure
Stage 1: Deacetylation of substrate by incubation of HDAC enzymes with compounds
Stage 2: Development by addition of Developer to digest the deacetylated substrate, and generate the fluorescent color; Detection: 360/460 Ex/Em 2) Inhibition of HDAC Enzymes

| Example | IC$_{50}$ (nM) HDAC 1 | IC$_{50}$ (nM) HDAC 6 |
|---|---|---|
| A | **** | * |
| B | **** | * |
| C | *** | * |
| D | *** | * |
| E | *** | * |
| F | **** | * |
| G | **** | * |
| H | **** | * |
| I | *** | * |
| J | **** | * |
| K | **** | * |
| L | **** | * |
| M | **** | * |
| N | **** | * |
| O | **** | * |
| P | **** | * |
| Q | *** | * |
| R | **** | * |
| S | **** | *** |

-continued

| Example | IC$_{50}$ (nM) HDAC 1 | IC$_{50}$ (nM) HDAC 6 |
|---|---|---|
| T | **** | *** |
| U | *** | * |
| V | **** | * |
| W | **** | * |
| X | **** | * |
| Y | **** | * |
| Z | **** | * |
| AA | *** | * |
| BB | *** | * |
| CC | **** | ** |
| DD | *** | * |
| EE | *** | * |
| FF | **** | * |
| GG | *** | * |
| HH | *** | * |
| II | *** | * |
| JJ | *** | * |
| KK | *** | * |
| LL | **** | * |
| MM | **** | * |
| NN | **** | * |
| OO | *** | * |
| PP | *** | * |
| RR | *** | * |
| SS | *** | * |

Key:
**** ≥10 uM
*** ≤10 uM ≥ 1 uM
** ≤1 uM ≥ 500 nM
* ≤500 nM

The invention claimed is:
1. A compound of the formula

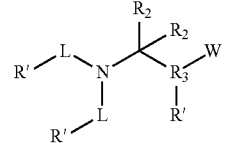

or a pharmaceutically acceptable salt thereof, wherein:
each R' is independently H or QR$_1$;
each Q is independently selected from the group consisting of: a bond, CO, CO$_2$, NH, S, SO, SO$_2$ and O;
each R$_1$ is independently selected from the group consisting of: H, C$_1$-C$_{10}$ alkyl, C$_2$-C$_{10}$ alkenyl, C$_2$-C$_{10}$ alkynyl, aryl, heteroaryl, C$_3$-C$_{10}$ cycloalkyl, halogen, C$_1$-C$_{10}$ alkylaryl, C$_1$-C$_{10}$ alkyl heteroaryl and C$_1$-C$_{10}$ heterocycloalkyl;
each L is a 5 to 10-membered nitrogen-containing heteroaryl, wherein at least one L is pyrazinyl;
W is

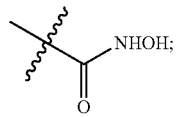

each R$_2$ is independently hydrogen or C$_1$ to C$_6$ alkyl;
R$_3$ is an aryl or heteroaryl;
each aryl or heteroaryl may be substituted by up to three substituents selected from the group consisting of C$_1$-C$_6$ alkyl, hydroxy, C$_1$-C$_3$ hydroxyalkyl, C$_1$-C$_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl) amino $C_1$-$C_3$ alkyl, bis($C_1$-$C_3$ alkyl) amino $C_1$-$C_3$ alkyl, $C_1$-$C_3$ alkyl sulfonylamino, halo, nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl and bis $C_1$-$C_3$-alkyl aminosulfonyl; and each alkyl, alkenyl or alkynyl may be substituted with a substituent selected from the group consisting of halogen, $NH_2$, $NO_2$ and hydroxyl.

2. The compound of claim 1, wherein in both L groups, the atom that is directly bonded to the N is a carbon, and at least one nitrogen atom is directly bonded to said carbon.

3. The compound of claim 1, wherein $R_3$ is phenylene or phenylene substituted with a halogen.

4. The compound of claim 1, wherein at least one of $R_2$ is H.

5. The compound of claim 1, wherein R' that is attached to L is independently selected from the group consisting of H, $C_1$-$C_{10}$ alkyl, O—($C_1$-$C_{10}$ alkyl), halogen, $C_1$-$C_{10}$ heterocycloalkyl, aryl, trifluoromethyl and heteroaryl.

6. The compound of claim 1, wherein at least one of R' is selected from the group consisting of H, halogen, $CF_3$, $C_1$-$C_6$ alkyl, aryl optionally substituted with halogen, heteroaryl optionally substituted with halogen, and heterocycloalkyl.

7. The compound of claim 1, wherein at least one of the R' that is attached to L is heterocycloalkyl.

8. The compound according to claim 7, wherein R' attached to $R_3$ is hydrogen or halogen.

9. The compound according to claim 7, wherein at least one of R' is $C_1$-$C_6$ alkyl optionally substituted with a substituent selected from the group consisting of halogen, $NH_2$, $NO_2$ and hydroxyl.

10. The compound according to claim 9, wherein at least one of R' is $C_1$-$C_6$ alkyl optionally substituted with halogen.

11. A pharmaceutical composition comprising a compound of claim 1 and a pharmaceutically acceptable carrier.

12. A compound selected from the group consisting of: N-Hydroxy-4-((pyrazin-2-yl(pyridin-2-yl)amino)methyl) benzamide; 4-(((5-Fluoropyridin-2-yl)(pyrazin-2-yl)amino) methyl)-N-hydroxybenzamide; 4-(((4-(4-Fluorophenyl) pyridin-2-yl)(pyrazin-2-yl)amino)methyl)-N-hydroxybenzamide; N-Hydroxy-4-{[(pyrazin-2-yl)(pyrimidin-4-yl)amino]methyl}benzamide; 3-Fluoro-N-hydroxy-4-{[(pyrazin-2-yl)(pyrimidin-4-yl)amino]methyl}benzamide; N-Hydroxy-6-{[(pyrazin-2-yl)(pyrimidin-4-yl)amino]methyl}pyridine-3-carboxamide; 4-{[Bis(pyrazin-2-yl)amino]methyl}-N-hydroxybenzamide; 4-{[Bis(pyrazin-2-yl)amino]methyl}-3-fluoro-N-hydroxybenzamide; 6-{[Bis(pyrazin-2-yl)amino]methyl}-N-hydroxypyridine-3-carboxamide; N-Hydroxy-4-{[(3-methoxypyridin-2-yl)(pyrazin-2-yl)amino]methyl}benzamide; 3-Fluoro-N-hydroxy-4-{[(3-methoxypyridin-2-yl)(pyrazin-2-yl)amino]methyl}benzamide; N-Hydroxy-6-{[(3-methoxypyridin-2-yl)(pyrazin-2-yl)amino]methyl}pyridine-3-carboxamide; N-Hydroxy-4-{[(pyrazin-2-yl)(pyridazin-3-yl)amino]methyl}benzamide; 3-Fluoro-N-hydroxy-4-{[(pyrazin-2-yl)(pyridazin-3-yl)amino]methyl}benzamide; N-Hydroxy-4-{[(3-methyl-1,2,4-thiadiazol-5-yl)(pyrazin-2-yl)amino]methyl}benzamide; N-Hydroxy-4-{[(4-methoxypyridin-2-yl)(pyrazin-2-yl)amino]methyl}benzamide; N-Hydroxy-4-{[(pyrazin-2-yl) [6-(trifluoromethyl)pyrazin-2-yl]amino]methyl}benzamide; 4-({[5-(6-Aminopyridin-3-yl)pyridin-2-yl](pyrazin-2-yl)amino}methyl)-N-hydroxybenzamide; 4-({[5-(2-Aminopyridin-4-yl)pyridin-2-yl](pyrazin-2-yl) amino}methyl)-N-hydroxybenzamide; N-hydroxy-4-[({5-[2-(methylamino)pyridin-4-yl]pyridin-2-yl}(pyrazin-2-yl) amino)methyl]benzamide; N-hydroxy-4-{[(pyrazin-2-yl)[5-(pyridin-4-yl)pyridin-2-yl]amino]methyl}benzamide; and pharmaceutically acceptable salts thereof.

* * * * *